United States Patent
Johnston et al.

(10) Patent No.: US 9,863,938 B2
(45) Date of Patent: Jan. 9, 2018

(54) SYNTHETIC ANTIBODIES

(71) Applicants: Stephen A Johnston, Tempe, AZ (US); Neal Woodbury, Tempe, AZ (US); John C Chaput, Phoenix, AZ (US); Christopher W Diehnelt, Chandler, AZ (US); Hao Yan, Chandler, AZ (US)

(72) Inventors: Stephen A Johnston, Tempe, AZ (US); Neal Woodbury, Tempe, AZ (US); John C Chaput, Phoenix, AZ (US); Christopher W Diehnelt, Chandler, AZ (US); Hao Yan, Chandler, AZ (US)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 887 days.

(21) Appl. No.: 14/198,316

(22) Filed: Mar. 5, 2014

(65) Prior Publication Data
US 2014/0221253 A1  Aug. 7, 2014

Related U.S. Application Data

(63) Continuation of application No. 12/445,923, filed as application No. PCT/US2007/081536 on Oct. 16, 2007, now abandoned.

(60) Provisional application No. 60/975,442, filed on Sep. 26, 2007, provisional application No. 60/852,040, filed on Oct. 16, 2006.

(51) Int. Cl.
*C40B 40/10* (2006.01)
*G01N 33/543* (2006.01)
*C07K 16/00* (2006.01)
*C07K 16/14* (2006.01)
*C07K 16/28* (2006.01)

(52) U.S. Cl.
CPC ....... *G01N 33/54306* (2013.01); *C07K 16/00* (2013.01); *C07K 16/14* (2013.01); *C07K 16/2881* (2013.01); *C07K 2317/31* (2013.01); *C40B 40/10* (2013.01)

(58) Field of Classification Search
None
See application file for complete search history.

(56) References Cited

U.S. PATENT DOCUMENTS

| | | |
|---|---|---|
| 5,196,510 A | 3/1993 | Rodwell et al. |
| 5,733,743 A | 3/1998 | Johnson et al. |
| 6,072,044 A | 6/2000 | Seeman et al. |
| 6,087,103 A | 7/2000 | Burmer |
| 6,255,469 B1 | 7/2001 | Seeman et al. |
| 6,537,749 B2 | 3/2003 | Kuimelis et al. |

(Continued)

FOREIGN PATENT DOCUMENTS

| WO | WO2005001121 A1 | 1/2005 |
|---|---|---|
| WO | WO2006124644 A2 | 11/2006 |

OTHER PUBLICATIONS

U.S. Appl. No. 60/438,805, filed Jan. 9, 2003, Kodadek.
(Continued)

*Primary Examiner* — Christian Boesen
(74) *Attorney, Agent, or Firm* — George A. Leone; Citadel Patent Law

(57) ABSTRACT

Methods for synthetic antibodies, methods for making synthetic antibodies, methods for identifying ligands, and related methods and reagents.

5 Claims, 38 Drawing Sheets

(56) References Cited

U.S. PATENT DOCUMENTS

| | | |
|---|---|---|
| 6,818,418 B1 | 11/2004 | Lipovsek et al. |
| 7,034,941 B2 | 4/2006 | Chen et al. |
| 2003/0082630 A1 | 5/2003 | Kolkman |
| 2003/0157561 A1 | 8/2003 | Kolkman |
| 2004/0161798 A1 | 8/2004 | Kodadek |
| 2004/0175756 A1 | 9/2004 | Kolkman |
| 2005/0048512 A1 | 3/2005 | Kolkman |
| 2005/0053973 A1 | 3/2005 | Kolkman |
| 2005/0089932 A1 | 4/2005 | Kolkman |
| 2005/0164301 A1 | 7/2005 | Kolkman |
| 2005/0221384 A1 | 10/2005 | Kolkman |
| 2005/0244863 A1 | 11/2005 | Kalim |
| 2006/0223114 A1 | 10/2006 | Stemmer |
| 2006/0234299 A1 | 10/2006 | Stemmer |
| 2006/0286603 A1 | 12/2006 | Kolkman |
| 2007/0003954 A1 | 1/2007 | Kodadek |

OTHER PUBLICATIONS

U.S. Appl. No. 60/680,200, filed May 12, 2005, Kodadek.

Baird, Cheryl (Principal Investigator). "Single-Chain Antibody Library", Systems Biology at Pacific Northwest National Laboratory, last update: Aug. 2009, downloaded from http://www.sysbio.org/dataresources/singlechain.stm.

Eck et al., "Spatial Constraints on the recognition of phosphoproteins by the tandem SH2 domains of the phosphatase SH-PTP2", Nature 379: 277-280 (1996).

Gillette et al., "Physical and functional association of RNA polymerase II and the proteasome", Proc. Natl. Acad. Sci. 101 (16): 5904-5909 (2004).

Maly et al., "Combinatorial target-guided ligand assembly: Identification of potent subtype-selective c-Src inhibitors", PNAS 97(6): 2419-2424 (2004).

McGuire et al., "In Vitro Selection of a Peptide with High Selectivity for Cardiomyocytes In vivo", J Mol Biol 342: 171-182 (2004).

Naffin et al., "Immobilized Peptides as High-Affinity Capture Agents for Self-Associating Proteins", Chem Biol 10: 251-259 (2003).

Oyama et al., "Isolation of lung tumor specific peptides from a random peptide library: generation of diagnostic and cell-targeting reagents", Cancer Letters 202:219-230 (2003).

Pluskey et al.,"Potent Stimulation of SH-PTP2 Phosphatase Activity by Simultaneous Occupancy of Both SH2 Domains", J Biol Chme 270(7): 2897-2900 (1995).

Profit et al., "Bivalent Inhibitors of Protein Tyrosine Kinases", JAm Chem Soc 121: 280-283 (1999).

Reddy et al., Transformation of Low-Affinity Lead Compounds into High-Affinity Protein Capture Agents, Chem Biol 11: 1127-1137 (2004).

Samli et al., "Peptide-Mediated Targeting of the Islets of Langerhans" Diabetes 54: 2103-2108 (2005).

Shuker et al., "Discovering High-Affinity Ligands for Proteins: SAR by NMR", Science 274: 1531-1534 (1996).

Stemke-Hale et al., "Screening the whole genome of a pathogen in vivo for individual protective antigens", Vaccine 23: 3016-3025 (2005).

Troitskaya et al., "Peptides as modulators of enzymes and regulatory proteins", Methods 32: 406-415 (2004).

PCT/US06/018507 (Published as WO06/124644, International Search Reports dated Jan. 12, 2007.

PCT/US07/081536, International Search Report dated Apr. 15, 2008.

U.S. Appl. No. 10/754,457, Response to Office Action filed Feb. 12, 2008.

U.S. Appl. No. 11/433,069, Response to Restriction Requirement filed Jan. 29, 2008.

Le et al. (Oct. 29, 2004), Nano Letters vol. 4 pp. 2343 to 2347.

Le et al. (Oct. 29, 2004), Nano Letters vol. 4 pp. 2343 to 2347 supporting Information pp. 1 to 5.

U.S. Appl. No. 12/445,923, Notice of Election/Restriction dated Nov. 13, 2012.

U.S. Appl. No. 12/445,923, Response to Restriction filed Dec. 13, 2012.

U.S. Appl. No. 12/445,923, Non-Final Office Action dated Sep. 6, 2013.

Bivalent Candidate Library

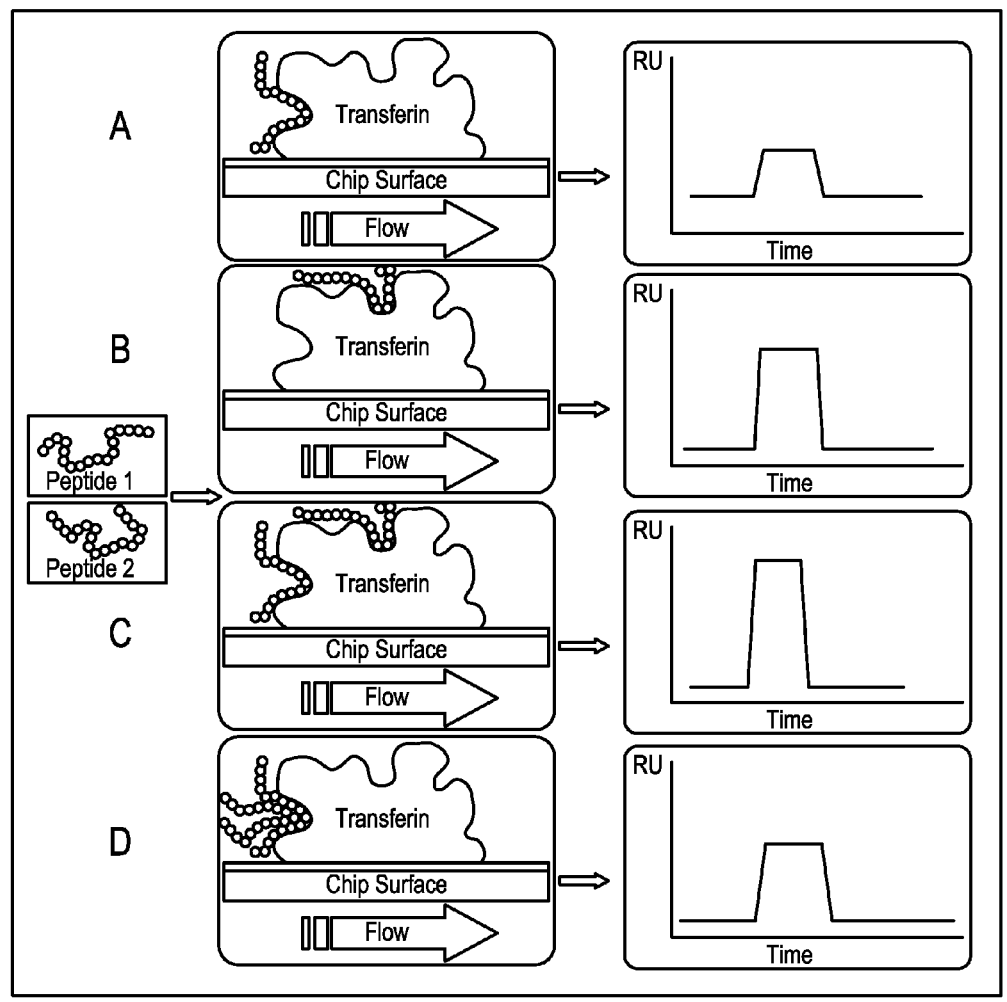
FIGS. 12A - D

| Peptide Pair | Response |
|---|---|
| 19 + 20 | ◐ |
| 19 + 21 | ● |
| 19 + 22 | ● |
| 19 + 23 | ● |
| 19 + 24 | ◐ |
| 19 + 25 | ◐ |
| 19 + 26 | ○ |
| 20 + 21 | ● |
| 20 + 22 | ● |
| 20 + 23 | ○ |
| 20 + 24 | ● |
| 20 + 25 | ◐ |
| 20 + 26 | ● |
| 21 + 22 | ● |
| 21 + 23 | ● |
| 21 + 24 | ◐ |
| 21 + 25 | ● |
| 21 + 26 | ◐ |
| 22 + 23 | ○ |
| 22 + 24 | ○ |
| 22 + 25 | ○ |
| 22 + 26 | ● |
| 23 + 24 | ● |
| 23 + 26 | ● |
| 24 + 25 | ● |
| 24 + 26 | ● |
| 25 + 26 | ◐ |

● Pairs of Peptides that bind to different site
◐ Pairs of Peptides whose binding sites overlap
○ Pairs of Peptides That compete for same binding site

Figure 13

```
SEQUENCE LISTING

<160> NUMBER OF SEQ ID NOS: 24

<210> SEQ ID NO 1
<211> LENGTH: 20
<212> TYPE: PRT
<213> ORGANISM: Artificial sequence
<220> FEATURE:
<223> OTHER INFORMATION: Synthetic peptide

<400> SEQUENCE: 1

Lys Glu Asp Asn Pro Gly Tyr Ser Ser Glu Gln Asp Tyr Asn Lys Leu
1               5                   10                  15

Asp Gly Ser Cys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Gly Gln Thr Gln Phe Ala Met His Arg Phe Gln Gln Trp Tyr Lys Ile
1               5                   10                  15

Lys Gly Ser Cys
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3
```

Gln Tyr His His Phe Met Asn Leu Lys Arg Gln Gly Arg Ala Gln Ala
1               5                   10                  15

Tyr Gly Ser Cys
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

His Ala Tyr Lys Gly Pro Gly Asp Met Arg Arg Phe Asn His Ser Gly
1               5                   10                  15

Met Gly Ser Cys
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Phe Arg Gly Trp Ala His Ile Phe Phe Gly Pro His Val Ile Tyr Arg
1               5                   10                  15

Gly Gly Ser Cys
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Ser Val Lys Pro Trp Arg Pro Leu Leu Thr Gly Asn Arg Trp Leu Asn
1               5                   10                  15

Ser Gly Ser Cys
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Ala Pro Tyr Ala Pro Gln Gln Ile His Tyr Trp Ser Thr Leu Gly Phe
1               5                   10                  15

Lys Gly Ser Cys
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 8

Ala His Lys Val Val Pro Gln Arg Gln Ile Arg His Ala Tyr Asn Arg
1               5                   10                  15

Tyr Gly Ser Cys
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Leu Asp Pro Leu Phe Asn Thr Ser Ile Met Val Asn Trp His Arg Trp
1               5                   10                  15

Met Gly Ser Cys
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide

<400> SEQUENCE: 10

Arg Phe Gln Leu Thr Gln His Tyr Ala Gln Phe Trp Gly His Tyr Thr
1               5                   10                  15

Trp Gly Ser Cys
            20

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Gly Thr Glu Lys Gly Thr Ser Gly Trp Leu Lys Thr Gly Ser Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Glu Gly Glu Trp Thr Glu Gly Lys Leu Ser Leu Arg Gly Ser Cys
1               5                   10                  15

<210> SEQ ID NO 13
<211> LENGTH: 51
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(7)
<223> OTHER INFORMATION: Amine-modified cytosine

<400> SEQUENCE: 13
``` ccccccccccg aaacaaccgc gagaggcacg cgcgtagccg tcaccggcta t         51

<210> SEQ ID NO 14
<211> LENGTH: 38
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (20)..(26)
<223> OTHER INFORMATION: amine-modified cytosine

<400> SEQUENCE: 14
gctacgcgcg tgcctctcgc cccccggtt gtttcggg                          38

<210> SEQ ID NO 15
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (30)..(32)
<223> OTHER INFORMATION: Thiol modifier

<400> SEQUENCE: 15
tagccggtgt gaagtttctg ctagtaatgc cc                               32

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Gln Tyr His His Phe Met Asn Leu Lys Arg Gln Gly Arg Ala Gln Ala
1               5                   10                  15

Tyr Gly Ser Gly
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

His Ala Tyr Lys Gly Pro Gly Asp Met Arg Arg Phe Asn His Ser Gly
1               5                   10                  15

Met Gly Ser Gly
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide

<400> SEQUENCE: 18

Phe Arg Gly Trp Ala His Ile Phe Phe Gly Pro His Val Ile Tyr Arg
1               5                   10                  15

Gly Gly Ser Gly
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide

<400> SEQUENCE: 19

Ala His Lys Val Val Pro Gln Arg Gln Ile Arg His Ala Tyr Asn Arg
1               5                   10                  15

Tyr Gly Ser Gly
            20

<210> SEQ ID NO 20
<211> LENGTH: 29
<212> TYPE: DNA
<213> ORGANISM: Artificial Sequence
<220> FEATURE:
<223> OTHER INFORMATION: Synthetic DNA

<400> SEQUENCE: 20
agtccgtggt agggcaggtt ggggtgact                                          29

<210> SEQ ID NO 21
<211> LENGTH: 15
<212> TYPE: DNA
<213> ORGANISM: Artificial Sequence
<220> FEATURE:
<223> OTHER INFORMATION: Synthetic DNA

<400> SEQUENCE: 21
ggttggtgtg gttgg                                                         15

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Ser Val Lys Pro Trp Arg Pro Leu Ile Thr Gly Asn Arg Trp Leu Asn
1               5                   10                  15

Ser Gly Ser Gly
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Phe Arg Gly Trp Ala His Ile Phe Phe Gly Pro His Val Ile Tyr Arg
1               5                   10                  15

Gly Lys Ser Gly
            20

<210> SEQ ID NO 24
<211> LENGTH: 28

```
<212> TYPE: PRT
<213> ORGANISM: Artificial Sequence
<220> FEATURE:
<223> OTHER INFORMATION: Synthetic Peptide

<400> SEQUENCE: 24

His Asn Leu Tyr Ser Pro Arg Gly Leu Tyr Leu Tyr Ser Leu Tyr Ser
1               5                   10                  15

Pro Arg Gly Leu Tyr Leu Tyr Ser Ala Leu Ala His
            20                  25
```

SYNTHETIC ANTIBODIES

CROSS REFERENCE

This application is a continuation of U.S. patent application Ser. No. 12/445,923 filed Nov. 23, 2010 a national stage entry of PCT Patent Application PCT/US07/81536 filed Oct. 16, 2007, U.S. Provisional Patent Application Ser. Nos. 60/852,040 filed Oct. 16, 2006 and 60/975,442 filed Sep. 26, 2007, all of which are incorporated by reference herein in their entirety.

STATEMENT OF GOVERNMENT INTEREST

This application was supported in part by U.S. government funding under NIAID grant number 5 U54 A1057156 and NCI grant number 5 U54 CA112952, and thus the U.S. government has certain rights in the invention.

BACKGROUND OF THE INVENTION

The basic use of antibodies or ligands is that they can distinguish one component from others in a complex mixture. The level of distinction required varies by use. The fundamental problem in antibody (ligand) development is to find some entity that can structurally complement a region or regions on the surface of the target, and that complementation is higher to a necessary degree above that of other components in the mixture.

Traditional antibodies are produced by injection of a protein or genes encoding proteins into an animal, usually multiple times over 1-4 months. Polyclonal antibodies are directly used from the serum. They can be affinity purified if a sufficient amount of the target protein is available. Using hybridoma technology, individual clones producing one element of the polyclonal population can be identified and the antibody propagated indefinitely. This procedure is generally erratic in the quality of the product, slow, low through put, suffers from contaminants and is expensive. It also requires killing animals. The most advanced form of this approach uses genetic immunization[1]. For each antibody the gene corresponding to the protein sequence is chemically synthesized and injected into the animal's skin with a gene gun. In parallel a small amount of protein is in vitro transcribed/translated using the same gene fragment. This protein is attached to beads for a direct assessment of reactivity. This system avoids the necessity of protein production for immunization, contaminants and is relatively high through-put. The quality of the antibodies is generally higher. However, this system still requires labor intensive animal handling[2]. To produce replenishable antibody, this system must be coupled to traditional monoclonal production[3].

Alternatives to direct production of antibodies in animals generally involve recurrent selection processes which are expensive, but more importantly not adaptable to high throughput methods. Antibodies used clinically have affinities (Kd) for their targets of $10^{-12}$ to $5 \times 10^{-8}$ M/I. This affinity is generated biologically by selecting mutations in the variable region of the antibody. The variable region is basically a flexible peptide held at the N and C-termini. By selecting from the ~$10^7$ variants in any individual and mutationally improving the sequence, antibody maturation can produce a good binder to almost any target. The common approach to replicating this process is to create a very large library ($10^9$-$10^{14}$ members) of molecules with variable nucleic acids or polypeptides and panning against the target to find the one or few best binders. A selection process is applied where strong binders out compete weaker binders.

This basic approach of panning large libraries is the most commonly used to find antibody-like elements. However, such panning has severe limitations. First, since one is looking for a very good match in interaction using a relatively short peptide or nucleic acid one has to generate and search large libraries. This is both time consuming and does not lend it self to high through put. In most cases, recurrent selection (panning) must be used to find the perfect match so only the best binding area on a target is found. It is difficult to find binders to multiple areas on the target. Other approaches have utilized meticulous application of chemistry and structural determinations to produce a molecule in which two small organic molecules were bound by a short rigid linker. However, this approach demands exquisite chemistry and structural biology, and the small molecules must be perfectly positioned for binding, thus putting severe restrictions on the nature of the linker. Furthermore, the nature of the binding elements, small organic molecules, is inherently limiting. It has proven very difficult to find a second site on a given protein that will sufficiently bind a small organic molecule. On reflection this makes perfect sense. Since the protein concentration in a cell is 60-100 mg/ml most exposed surfaces of a protein must be nonbinding or all proteins would agglomerate. Therefore, small molecules will generally only bind in deep pockets on the protein.

Thus, new methods for ligand discovery and resulting ligands for use in constructing, for example, synthetic antibodies are needed in the art.

SUMMARY OF THE INVENTION

In a first aspect, the present invention provides methods for identifying affinity elements to a target of interest, comprising (a) contacting a substrate surface comprising an array of between $10^2$ and $10^7$ different test compounds of known composition with a target of interest under conditions suitable for moderate affinity binding of the target to target affinity elements if present on the substrate, wherein the target is not an Fv portion of an antibody, and wherein the different test compounds are not derived from the target; and (b) identifying test compounds that bind to the target with at least moderate affinity, wherein such compounds comprise target affinity elements. In one embodiment of the methods of this first aspect of the invention, the substrate surface is addressable. In another embodiment, the methods further comprise identifying test compounds that do not bind to the target with at least moderate affinity. In a further embodiment, the test compounds have a molecular weight of between 1000 Daltons and 10,000 Daltons. In a further embodiment, the test compounds are polypeptides. In another embodiment, the methods further comprise contacting the same substrate surface or a separate substrate surface with competitor, and determining a ratio of test compound binding to target versus test compound binding to competitor. In a further embodiment, the methods further comprise identifying combinations of target affinity elements that bind to different sites on the same target. The methods may further comprise determining an appropriate spacing between the target affinity elements in an affinity element combination to increases a binding affinity and/or specificity for the target of the affinity element combination relative to a binding affinity and/or specificity of the target affinity elements alone for the target. In a further embodiment, the methods comprise linking a combination of affinity elements, wherein the linker provides a spacing of between about 0.5 nm and about 30 nm between a first affinity element and a second affinity element. The methods may further comprise optimizing binding affinity of one or both of the first affinity element and the second affinity element to the target. In a further embodiment, the first aspect provides synthetic antibodies made by the methods of the first aspect of the invention.

In a second aspect, the present invention provides synthetic antibodies comprising:

(a) a first affinity element that can bind a first target;

(b) a second affinity element that can bind the first target, and which can bind to the first target in the presence of the first affinity element bound to the first target; and (c) a linker connecting the first affinity element and the second affinity element, wherein one or both of the first affinity element and the second affinity element have a molecular weight of at least 1000 Daltons;

wherein at least one of the first affinity element and the second affinity element are not derived from the first target;

wherein the synthetic antibody has an increased binding affinity and/or specificity for the first target relative to a binding affinity and/or specificity of the first affinity element for the first target and relative to a binding affinity and/or specificity of the second affinity element for the target; and wherein the first target is not the Fv of an antibody. In a further embodiment, both the first affinity element and the second affinity element have a molecular weight of between about 1000 Daltons and 10,000 Daltons. In another embodiment, the linker provides a spacing of between about 0.5 nm and about 30 nm between the first affinity element and the second affinity element. In a further embodiment, neither the first affinity element nor the second affinity element are derived from an Fv region of an antibody. In another embodiment, neither the first affinity element nor the second affinity element are derived from the first target. In a still further embodiment, the first affinity element and the second affinity element comprise polypeptides or nucleic acids. In a further embodiment, the synthetic antibodies further comprise third or further affinity elements connected to the first affinity element and the second affinity element. In a further embodiment, the synthetic antibodies are bound to a substrate.

In another embodiment, the present invention provides a substrate comprising:

(a) a surface; and (b) a plurality of synthetic antibodies according to the second aspect of the invention attached to the surface.

In a third aspect, the present invention provides methods for making a synthetic antibody, comprising connecting at least a first affinity element and a second affinity element for a given target via a linker;

wherein one or both of the first affinity element and the second affinity element have a molecular weight of at least 1000 Daltons;

wherein at least one of the first affinity element and the second affinity element are not derived from the first target;

wherein the synthetic antibody has an increased binding affinity and/or specificity for the first target relative to a binding affinity and/or specificity of the first affinity element for the first target and relative to a binding affinity and/or specificity of the second affinity element for the target; and wherein the first target is not the Fv of an antibody. In one embodiment, both the first affinity element and the second affinity element have a molecular weight of between 1000 Daltons and 10,000 Daltons. In another embodiment, the linker provides a spacing of between about 0.5 nm and about 30 nm between the first affinity element and the second affinity element. In further embodiments, one or both of the first and second affinity elements comprise a polypeptide or a nucleic acid.

In a further aspect, the present invention provides methods for ligand identification, comprising:

(a) contacting a substrate surface comprising a target array with one or more potential ligands, wherein the contacting is done under conditions suitable for moderate to high affinity binding of the one or more ligands to suitable targets present on the substrate; and (b) identifying targets that bind to one or more of the ligands with at least moderate affinity. In one embodiment, the one or more potential ligands are selected from the group consisting of antibodies and synthetic antibodies according to the second aspect of the invention. In a further embodiment, the array of targets is mounted in a flow chamber, wherein (i) a first buffer comprising the one or more potential ligands is flowed over the addressable array, (ii) wherein identifying targets that bind to one or more of the ligands with at least moderate affinity comprises analyzing real-time affinity data gathered by an array reader;

(iii) the first buffer flow over the addressable array is stopped after at least moderate binding to the array is detected;

(iv) repeating steps (i)-(iii) a desired number of times using a further buffer comprising one or more further potential ligands.

In another aspect, the present invention provides methods for identifying a synthetic antibody profile for a test sample of interest, comprising contacting a substrate comprising a plurality of synthetic antibodies according to the present invention with a test sample and comparing synthetic antibody binding to the test sample with synthetic antibody binding to a control sample, wherein synthetic antibodies that differentially bind to targets in the test sample relative to the control sample comprise a synthetic antibody profile for the test sample.

In a still further aspect, the present invention provides compositions, comprising:

(a) a first affinity element bound to a template nucleic acid strand;

(b) a second affinity element bound to a complementary nucleic acid strand, wherein the first affinity element and the second affinity element non-competitively bind to a common target;

wherein the template nucleic acid strand and the complementary nucleic acid strand are annealed via base pairing to form an assembly;

wherein the first affinity element and the second affinity element are separated in the assembly; and wherein either the template nucleic acid strand, the complementary nucleic acid strand, or both, are bound to a surface of a substrate.

DESCRIPTION OF THE FIGURES

FIG. 12. Expected SPR signal upon (a) interaction of a first ligand alone with an immobilized target; (b) interaction of a second ligand alone with an immobilized target; (c) interaction of a first and second ligand with an immobilized target where the ligands do not compete or interfere; (d) binding of two ligands that do not bind distinct sites on the target, but instead compete for the same binding site.

FIG. 13. Results of evaluation for binding to distinct target sites, of a number of pairs of the polypeptides that were identified as described in Example 2 (see Table 1).

DETAILED DESCRIPTION OF THE INVENTION

Figure 1:
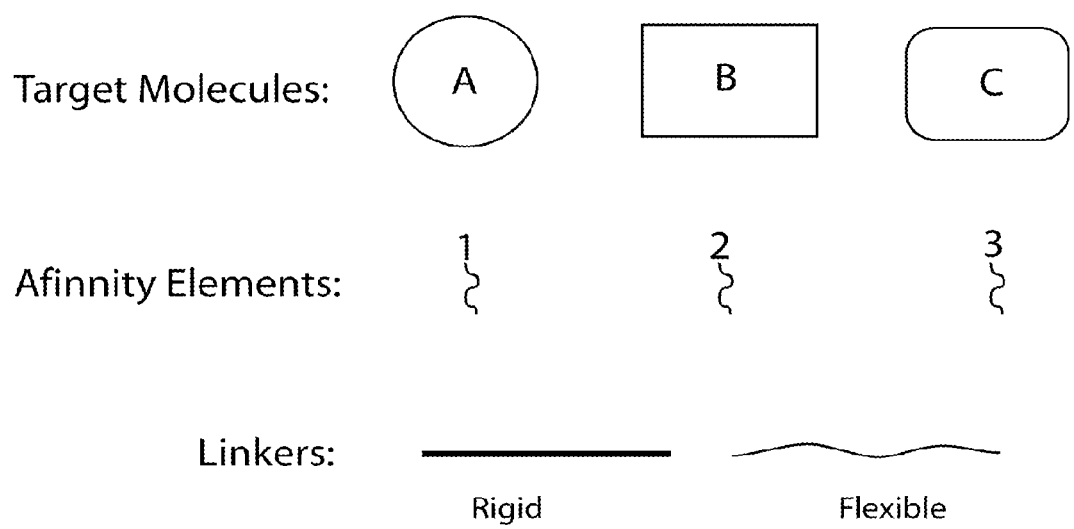
FIG. 1. Legend for conceptual drawings of synbody variations shown FIGS. 2-8.
Figure 2:
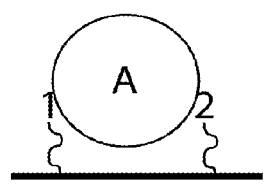
FIG. 2. Schematic of simple synbody.
Figure 3A:
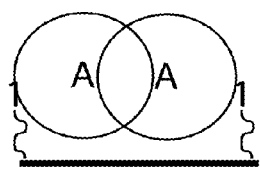
FIG. 3. Schematic of synbodies specific for (a) homodimers and (b) heterodimers.
Figure 3B:
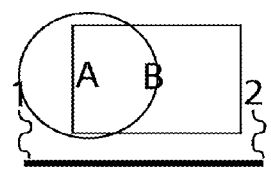

In a first aspect, the present invention provides methods for identifying affinity elements to a target of interest, comprising (a) contacting a substrate surface comprising an array of between $10^2$ and $10^7$ different test compounds of known composition with a target of interest under conditions suitable for moderate affinity binding of the target to target affinity elements if present on the substrate, wherein the target is not an Fv portion of an antibody, and wherein the different test compounds are not derived from the target; and (b) identifying test compounds that bind to the target with at least moderate affinity, wherein such compounds comprise target affinity elements.

The inventors have discovered that screening for affinity elements to a target of interest using an array of different test compounds of known composition permits a large amount of chemical/structural space to be adequately sampled using only a small fraction of the space. The resulting methods provide a rapid and high throughput method for identifying affinity elements to targets of interest. While not being bound by any specific hypothesis, the inventors propose that the tremendously large number of possible arrangements for a target of a given size actually form a very limited number of structural forms or combinations of patches of smaller sequences, providing the ability to identify affinity elements to a target of interest by screening a target of interest against a much smaller array of test compounds (ie: potential affinity elements) than previously considered possible. Since the composition of each test compound on the substrate surface is known, the method is a screen for affinity elements, not a selection. Screenable libraries as used in the methods of the present invention are much smaller ($\sim 10^2$ to $10^7$) than selectable libraries ($10^9$-$10^{14}$). Thus, the process of affinity element discovery is limited only by the rate at which individual targets can be screened on test compound-containing substrate surfaces. In this sense it is distinct from current selection techniques, in which recurrent selections using unknown sequences are required. Exemplary substrate surfaces are described below.

In one embodiment, the substrate surface comprises an addressable test compound array. "Addressable" means that test compounds on the substrate surface are present at a specific location on the substrate, and thus detection of binding events serves to identify which test compound has bound target.

The "different test compounds of known composition" are of known structure and/or composition. Thus, for example, if the test compounds comprise or consist of nucleic acids or polypeptides, their nucleic acid or amino acid sequence is known, while further structural information may also be known (although this is not required). Furthermore, the test compounds are not all related based on minor variations of a core sequence or structure. Thus, when the test compounds comprise nucleic acids or polypeptides, the nucleic acid or polypeptide sequences are known, but the test compounds are not simply a series of mutants/fragments of a known sequence, nor a series of epitopes/possible epitopes from a given antigen. The different test compounds may include variants of a given test compound (such as polypeptide isoforms), but at least 10% of the test compounds on the array are structurally and/or compositionally unrelated. In various embodiments, 20%, 30%, 40%, 50%, 60%, 70%, 80%, 90%, 95%, 98%, or more of the test compounds on the array are structurally and/or compositionally unrelated.

The different test compounds can comprise or consist of any class of compounds capable of binding to a target of interest, but the different test compounds are not derived from the target. As used herein, "not derived from" means that the test compounds are not fragments of the target to be screened. In this embodiment, for example, if the target is a nucleic acid, the different test compounds do not consist of a polynucleotide found within the target (on its sense or antisense strand). Similarly, if the target is a protein, the test compounds do not individually consist of a polypeptide found within the target, or an "antisense" version thereof (ie: polypeptides which are encoded on the opposite strands of the DNA encoding the protein target in a given reading frame, which can have an affinity to bind each other based on hydropathic complementary of the polypeptides).

It will be understood by those of skill in the art that the arrays may further comprise control compounds, and that such control compounds may be of any type suitable to serve as appropriate controls for target binding, including but not limited to antibodies, Fv regions of antibodies, variable regions of an antibody, or antigen binding regions of an antibody, and control compounds derived from the target. In various embodiments, up to 25% of the compounds on the substrate surface may be control compounds; in various further embodiments, 20%, 15%, 10%, 5%, 4%, 3%, 2%, 1%, 0.5%, 0.1% or less of the compounds on the substrate surface are control compounds.

In another embodiment, the different test compounds on the array are not antibodies, Fv regions of antibodies, variable regions of an antibody, or antigen binding regions of an antibody.

Classes of test compounds suitable for use in the present invention include, but are not limited to, nucleic acids, polypeptides, peptoids, polysaccharides, organic compounds, inorganic compounds, polymers, lipids, and combinations thereof. The test compounds can be natural or synthetic. The test compounds can comprise or consist of linear or branched heteropolymeric compounds based on any of a number of linkages or combinations of linkages (e.g., amide, ester, ether, thiol, radical additions, metal coordination, etc.), dendritic structures, circular structures, cavity structures or other structures with multiple nearby sites of attachment that serve as scaffolds upon which specific additions are made. In various preferred embodiments, all or a plurality of the test compounds are non-naturally occurring. In other embodiments, the test compounds are selected from the group consisting of nucleic acids and polypeptides. In one specific embodiment, if the different test compounds consist of nucleic acids, then the target is not a nucleic acid. In another embodiment, the different test compounds are not nucleic acids. In a further embodiment, the test target is not a nucleic acid.

In a further embodiment, the different test compounds on the substrate are of the same class of compounds (ie: all polypeptides; all nucleic acids, all polysaccharides, etc.) In other embodiments, the test compounds comprise different classes of compounds in any ratio desired. These test compounds can be spotted on the substrate or synthesized in situ, using standard methods in the art. The test compounds can be spotted or synthesized in situ in combinations in order to detect useful interactions, such as cooperative binding.

The substrates may further comprise control compounds or elements as discussed above, as well as identifying features (RFID tags, etc.) as suitable for any given purpose.

In one embodiment, the different test compounds are chosen at random using any technique for making random selections. In a further embodiment, an algorithmic approach for selecting different test compounds is used.

In a further embodiment, all or a plurality of the test compounds on the array do not naturally occur in an organism from which the target is derived, where the target is a biological molecule. In another embodiment, where the test compounds comprise polypeptides, all or a plurality of the polypeptide test compounds are not found in the SWIS-SPROT database (web site ebi.ac.uk/swissprot/), either as a full length polypeptide or as a fragment of a polypeptide found in the SWISSPROT database. In other words, the test compounds are not derived from naturally occurring proteins. In another embodiment, where the test compounds comprise nucleic acids, all or a plurality of the nucleic acid test compounds are not found in the GENBANK database (web site ncbi.nlm.nih.gov/Genbank/), either as a full length nucleic acid or as a fragment of a nucleic acid found in the GENBANK database. There are at least two reasons to use such "non-naturally occurring" test compounds. First, there is little known about what potential binding space would be occupied by a particular collection of elements. Arguments could be made for or against many alternatives. Second, life space (ie: naturally occurring compounds) has been selected to meet many requirements beyond simply binding, and the binding is in very specific conditions in life. Thus, naturally occurring compounds suffer from constraints over many degrees of freedom and these constraints would handicap a search for affinity elements to a large number or targets. An unanticipated benefit of using non-naturally occurring different test compounds (as discussed below) is that, overall, at least in the case of polypeptides, the resulting test compounds tend to be more soluble and well behaved in solution than a similarly sized set of compounds derived from life space compounds, which provides advantages in binding assays, such as in the array-based formats disclosed herein. In various further embodiments, at least 10%, 20%, 30%, 40%, 50%, 60%, 70%, 80%, 90%, 95%, 98% or more of the test compounds on the array do not naturally occur in an organism from which the target is derived, where the target is a biological molecule. Similar various further embodiments are contemplated for the specific nucleic acid and polypeptide embodiments disclosed above.

In a further embodiment, the test compounds have a molecular weight of between about (ie: +/−5%) 1000 Daltons (D) and 10,000 D. As discussed below, test compounds within this molecular weight class are of particular utility in preparing synthetic antibodies (also referred to herein as "synbodies") according to the present invention. In one embodiment, polypeptide test compounds for use in the methods of this aspect of the invention are between about 1000 Daltons and 4000 Daltons (up to approximately 30 amino acid residues); in various further embodiments between 1100D-4000D; 1200D-4000D; 1300D-4000D; 1400D-4000D; 1500D-4000D; 1000D-3500D; 1100D-3500D; 1200D-3500D; 1300D-3500D; 1400D-3500D; 1500D-3500D; 1000D-2000D; 1100D-3000D; 1200D-3000D; 1300D-3000D; 1400D-3000D; and 1500D-3000D. In another embodiment, nucleic acid aptamers of up to 10,000 Daltons are used (ie: approximately 30 bases).

As used herein, "at least moderate affinity binding" of the target to target affinity elements generally means a binding affinity of at least about (ie: +/−5%) 500 µM. In various further embodiments, "at least moderate binding affinity" for the target means at least about 250 µM, 150 µM; 100 µM, 50 µM, or 1 µM. In various further embodiments, the target affinity elements possess binding affinity for the target of between about (ie: +/−5%) 1 µM and 500 µM. In various further embodiments, moderate affinity binding of the target to target affinity elements generally means a binding affinity of between about 1 µM-250 µM; 1 µM-150 µM; 10 µM-500 µM; 25 µM-500 µM; 50 µM-500 µM; 100 µM-500 µM; 10 µM-250 µM; 50 µM-250 µM; and 100 µM-250 µM.

As used herein, "binding" of test compounds to a target refers to selective binding in a complex mixture (ie: above background), and does not require that the binding be specific for a given target, as traditional antibodies often cross-react. The extent of acceptable target cross-reactivity for a given affinity element depends on how it is to be used and can be determined by those of skill in the art based on the teachings herein. For example, methods to modify the affinity and selectivity of the synthetic antibodies produced using the binders identified in the methods of the invention are described below. Such binding can be of any type, including but not limited to covalent binding, hydrophobic interactions, van der Waals interactions, the combined effect of weak non-covalent interactions, etc.

Specific conditions suitable for moderate affinity binding of the target to the test compounds will depend on the type of target and test compounds (ie: polypeptide, nucleic acid, etc.), as well as the specific structure of each (ie: length, sequence, etc.). Determination of suitable conditions for moderate affinity binding of a specific target to a specific collection of test compounds is well within the level of skill in the art based on the teachings herein. In various non-limiting embodiments, conditions such as those described in the examples that follow can be used.

For example, the screen can be done under non-biological conditions, such as non-aqueous conditions. This is in contrast to prior methods of selection mentioned above that use a living system in some phase. Most antibodies do not function when applied to the surface of arrays. In contrast, the binding agents developed here are screened to function on surfaces.

The binding can be detected by many other methods, including but not limited to direct labeling of the target, secondary antibody labeling of the target or directly determined by SPR electrochemical detection, micromechanical detection (e.g., frequency shifts in resonant oscillators), electronic detection (changes in conductance or capacitance), mass spectrometry or other methods. The target can also be pre-incubated with another control compound (ie, protein, drug or antibody, etc.) to block the binding of particular classes of affinity targets in order to focus the search. The binding can be done in the presence of competitive inhibitors (including but not limited to $E.\ coli$ extract or serum) to accentuate specificity.

In another embodiment, the methods comprise identifying affinity elements for more than one target at a time. The methods of the invention are easily amenable to multiplexing. In one embodiment, each target is labeled with a different signaling label, including but not limited to fluorophores, quantum dots, and radioactive labels. Such multiplexing can be accomplished up to the resolution capability of the labels. Targets that bound two or more affinity elements would produce summed signals. Other techniques for multiplexing of the assays can be used based on the teachings herein.

In various embodiments, the substrate surface comprises an array of between 100 and 100,000,000 different test compounds. Such arrays may further comprise control compounds or elements as discussed above. In various other embodiments, the substrate surface comprises between 100-10,000,000; 100-2,000,000; 100-5,000,000; 100-1,000,000; 100-500,000; 100-100,000; 100-75,000; 100-50,000; 100-25,000; 100-10,000; 100-5,000, 100-4,000, 250-1,000,000, 250-500,000, 250-100,000, 250-75,000; 250-50,000; 250-25,000; 250-10,000; 250-5,000, 250-4,000; 500-1,000,000; 500-500,000, 500-100,000, 500-75,000; 500-50,000; 500-25,000; 500-10,000; 500-5,000, 500-4,000; 1,000-1,000,000; 1,000-500,000; 1,000-100,000, 1,000-75,000; 1,000-50,000; 1,000-25,000; 1,000-10,000; 1,000-8,000, 1,000-5,000 and 1,000-5,000 different test compounds.

As used herein "nucleic acids" are any and all forms of alternative nucleic acid containing modified bases, sugars, and backbones. These include, but are not limited to DNA, RNA, aptamers, peptide nucleic acids ("PNA"), 2'-5' DNA (a synthetic material with a shortened backbone that has a base-spacing that matches the A conformation of DNA; 2'-5'

DNA will not normally hybridize with DNA in the B form, but it will hybridize readily with RNA), locked nucleic acids ("LNA"), Nucleic acid analogues include known analogues of natural nucleotides which have similar or improved binding properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press).

The term "polypeptide" is used in its broadest sense to refer to a sequence of subunit amino acids, amino acid analogs, or peptidomimetics. The subunits are linked by peptide bonds, except as noted. The polypeptides may be naturally occurring, processed forms of naturally occurring polypeptides (such as by enzymatic digestion), chemically synthesized or recombinantly expressed. Preferably, the polypeptides for use in the methods of the present invention are chemically synthesized using standard techniques. The polypeptides may comprise D-amino acids (which are resistant to L-amino acid-specific proteases), a combination of D- and L-amino acids, β amino acids, and various other "designer" amino acids (e.g., β-methyl amino acids, Cα-methyl amino acids, and Nα-methyl amino acids, etc.) to convey special properties. Synthetic amino acids include ornithine for lysine, and norleucine for leucine or isoleucine. In addition, the polypeptides can have peptidomimetic bonds, such as ester bonds, to prepare polypeptides with novel properties. For example, a polypeptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. The affinity elements can also be peptoids (N-substituted glycines), in which the sidechains are appended to nitrogen atoms along the molecule's backbone, rather than to the α-carbons, as in amino acids.

The term "polysaccharide" means any polymer (homopolymer or heteropolymer) made of subunit monosaccharides, oligimers or modified monosaccharides. The linkages between sugars can include but are not limited to acetal linkages (glycosidic bonds), ester linkages (including phophodiester linkages), amide linkages, ether linkages, etc. The lipids can be any nonpolar-comprising hydrocarbon-based molecule, including amphipathic, amphiphilic, aliphatic, straight chain, branched, aromatic, saturated, or unsaturated lipids. Specific lipid types that can be used as affinity elements here include, but are not limited to phospholipids, fatty acids, glycerides (mono-, di-, tri-, etc.), sphingolipids, and waxes. Similarly, any other suitable organic compounds, inorganic compounds, therapeutic agents, and polymers can be used as affinity elements according to the present invention.

The target can be any structure that an affinity element can bind to other than an Fv portion of an antibody (ie: the antigen binding portion of an antibody), including but not limited to nucleic acids, polypeptides, peptoids, polysaccharides, organic compounds, inorganic compounds, metabolites, sugar oligomers, sugar polymers, other synthetic polymers (plastics, fibers, etc.), polypeptide complexes, polypeptide aggregates, polypeptide/nucleic acid complexes, lipids, glycoproteins, lipoproteins, polypeptide/carbohydrate structures (such as peptdidogycans), chromatin structures, membrane fragments, cells, tissues, organs, organelles, inorganic surfaces, electrodes, semiconductor substrates including but not limited to silicon-based substrates, dyes, nanoparticles, nanotubes, nanowires, quantum dots, and medical devices. The target can be a single such structure, or a multimer of the same or different such structure (ie: homodimers, heterodimer, etc.), as discussed in more detail below. As is also discussed in more detail below, when additional affinity elements are used, the target(s) for the further affinity elements can be the same as the target for the first and/or second affinity elements, or different. In one embodiment, the target is not an antibody, an antibody bearing cell, or an antibody-binding cell surface receptor (or portion thereof suitable for antibody binding). In another embodiment, the target does not comprise a nucleic acid. In a further embodiment, the target comprises a polypeptide.

Any suitable substrate surface can be used in the methods of the invention, including but not limited to surfaces provided by microarrays, beads, columns, optical fibers, wipes, nitrocellulose, nylon, glass, quartz, mica, diazotized membranes (paper or nylon), silicones, polyformaldehyde, cellulose, cellulose acetate, paper, ceramics, metals, metalloids, semiconductive materials, quantum dots, coated beads, other chromatographic materials, magnetic particles; plastics and other organic polymers such as polyethylene, polypropylene, and polystyrene; conducting polymers such as polypyrole and polyindole; micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, and other fibrous or stranded polymers. In one exemplary embodiment, the substrate comprises a substrate suitable for use in a "dipstick" device, such as one or more of the substrates disclosed above.

In one non-limiting embodiment of the methods of this first aspect of the invention, the target is detectably labeled (as discussed above) such as, in the case of peptides or proteins, a tag that can be bound by a labeled antibody. This target is then applied to a spotted array on a slide containing between 5,000 and 1,000,000 test polypeptides of 20 amino acids long. In this example, the polypeptides can be attached to the surface through the C-terminus. The sequence of the polypeptides was generated randomly from 19 amino acids, excluding cysteine. When running this type of experiment, typically 0.1% to 10% of polypeptides show some binding to the target. The binding reaction can include, for example, an excess of *E. coli* proteins (such as a 100 fold excess) as non-specific competitor labeled with another dye so that the specificity ratio for each polypeptide binding target can be determined. The polypeptides with the highest specificity and binding can be picked. The identity of the polypeptide on each spot is known, and thus they can be readily identified for further use, either through use of stocks of the selected polypeptides or resynthesis of the polypeptides.

Thus, in another embodiment, the methods further comprise contacting the same substrate surface or a separate substrate surface with competitor, and determining a ratio of test compound binding to target versus test compound binding to competitor. This enables identification of test compounds that not only have high affinity for the target but also relatively low affinity for competitor. In one embodiment, the target is a polypeptide and the competitor comprises a cell lysate or protein extract, including but not limited to a bacterial cell lysate or protein extract. In another embodiment, the competitor is differentially labeled from the target for ease of detection and binding ratio determination. In further embodiments, the target/competitor screen is conducted on two or more separate substrate surfaces (for example, *E coli* lysate as the competitor on one, salmon sperm on another, abundant serum proteins on another), and binding ratios compared across the different competitors (such as in a matrix format) to identify probes that are reasonably specific. An exemplary embodiment (*E coli* lysate competition) is described in detail below.

In one embodiment, the methods further comprise (c) identifying test compounds that do not bind to the target with at least moderate affinity. Since the composition of each test compound on the substrate is known, the methods of this first aspect provide information on the binding affinity of the arrayed test compounds for each target tested. These data can be used for a variety of purposes, including but not limited to creating a database of test compounds and their binding affinity (or lack thereof) to different targets. Thus, in a further embodiment, the methods of any aspect or embodiment of the invention further comprise storing in a database the data obtained using the methods of the invention. Such data includes, but is not limited to, affinity element binding affinity (including quantitative measurements of dissociation constants, binding free energy changes, binding enthalpy changes and binding entropy changes), specificity, and structure/sequence, and non-affinity element (ie: non-binder) structure/sequence. Data from these analyses can be used to create a database that allows predicting which affinity elements bind different structures. Polypeptides in different groups tend to bind different surfaces of the same protein. This information can also be used to design better affinity elements for lead target analysis.

In another embodiment, the methods of the invention further comprise identifying combinations of affinity elements that bind to different sites on the same target. The affinity elements selected using the methods of the invention typically have relatively moderate affinity for the target (~uM). By linking two affinity elements that bind the same target non-competitively, the affinity and selectivity can be increased (see data below). Thus, combinations of affinity elements that bind to different target sites are first identified. Natural antibodies do this by selection of light and heavy chain variants that bind to sites on the protein with synergy. The space between light and heavy chains is largely fixed so the optimal binding site/spacing combination is selected among millions of antibody variants. The methods disclosed herein have an advantage over the natural process of antibody production by allowing essentially any spacing between sites. If the target is a dimer or a multimer, one affinity element can bind multiple sites on the target complex simultaneously (ie: affinity element binding to each of the monomers). For example, it is estimated that approximately 60% of soluble proteins are dimers or other multimers. Therefore, in many cases joining two (or more) copies of a single affinity element may provide increased affinity and/or selectivity, though affinity and/specificity may be enhanced by using two (or more) different affinity elements when the target comprises a multimer.

Any suitable technique for identifying affinity elements that bind to different sites on the same target can be used, and many such techniques are known to those of skill in the art. In some cases, particularly for homodimeric proteins, the same affinity element can be used twice to create the synthetic antibody (ie: the binding is still for different sites, one to each member of the homodimeric pair). In one non-limiting example, affinity elements that bind to different sites on the same target are identified by pre-incubating the target with a first affinity element, under conditions to promote binding of the first affinity element to the target, and then contacting the target with one or more further affinity elements, to see which further affinity elements bind to the target in the presence of first affinity element bound to the target. For example, one method to discover polypeptides binding to different sites on the same protein is to pre-incubate the protein target with one polypeptide affinity element and observe which polypeptides on the array still bind. By doing this in an iterative fashion one can classify all the binding polypeptides as to target sites on a protein. Another method is to combine all protein specific polypeptide affinity elements in a pairwise manner and then spot them on the array to assess binding to the original target. Two polypeptide affinity elements that bind to two different areas of the protein should have more than additive affinity. Even though the polypeptide affinity elements are not spaced at a single distance, there is a random distribution of polypeptide spacing. If the average spacing is around the optimal distance, then enhanced binding can occur. This can also be affected by the length and flexibility of the linker arm to the surface. In this way the pairs of polypeptide affinity elements that bind different sites on the target can be discovered in a high through put fashion. Data supporting both approaches to finding pairs is discussed below. The pairs of polypeptide affinity elements can be affixed to a surface as a mixture to take advantage of the cooperative binding. However, only a subset of the polypeptides would be in the optimal spacing. An alternative is to affix the pairs of polypeptides on a surface that has been derivatized with orthogonal chemistries so that the polypeptides can be distributed in a chosen spacing. Another embodiment involves binding the target to a surface plasmon chip and each polypeptide is flowed over to determine its binding to the target. Then the same is done for each pair of polypeptide affinity elements. For polypeptide affinity elements that occupy the same or overlapping sites on the target, the response will be the average of the individual polypeptide affinity elements. For those occupying different sites the response will be the sum. As predicted by our analysis of the effectiveness of screening versus selection, using this technique we readily obtain several polypeptide affinity elements binding two or more sites on the target.

The methods of the invention further comprise connecting two or more affinity elements (for example, as described in any of the synthetic antibody embodiments below) for a given target via a linker to create a synthetic antibody, wherein an affinity and/or specificity of the synthetic antibody for the target is increased relative to an affinity and/or specificity of either affinity element alone for the target, as discussed in more detail below.

The methods of the invention do not try to make one high affinity, perfect match synthetic antibody, but instead takes advantage of it being easier to find two weak binders and link them to produce a higher affinity binder. While not being bound by any specific hypothesis, the inventors believe that since most of the surfaces of proteins are not deeply pocketed, it will be beneficial to use larger molecules to sufficiently bind (near micromolar) the surface. This is difficult to do by selection in a library. Therefore we have developed efficient methods to screen for binding elements. However, screenable libraries are necessarily much smaller than selectable libraries ($10^9$-$10^{14}$). These two demands seem contradictory. We want to limit the library size but search larger molecule space. For example, the sequence space of 20 amino acid polypeptides using all possible 20 amino acids is $10^{26}$. Our surprising discovery was that these two demands can be reconciled because the structural space represented on the surface of proteins is covered by a small number of 20 amino acid polypeptides. This allows using a small number of compounds to cover enough space to give at least micromolar Kds on two or more sites per target. In addition, since this system allows arriving at the lead ligands by screening, it has the important implication that these synbodies could be produced in a high through put fashion.

In another embodiment, the method further comprises linking two affinity elements at an appropriate distance to obtain an increase in specificity and affinity. The linker can be any molecule or structure that can connect the first and second affinity elements, including but not limited to nucleic acid linkers, amino acid linkers, any polymeric linker (heteropolymers or homopolymer), PEG linkers, nucleic acid tiles, etc. In some embodiments, the linker is a polymer comprising one or more proline-glycine-proline subunits. In some embodiments the linker is a polymer comprising one or more hydroxproline subunits. A variety of polymers comprising proline and/or hydroxyproline are capable of forming helical structures having useful and potentially optimizable rigidity and elasticity properties. Such linkers can be naturally occurring compounds/structures or may be non-natural, including but not limited to nucleic acid analogues, amino acid analogues, etc. Connection between an affinity element and a linker can be of any type, including but not limited to covalent binding, hydrogen bonding, ionic bonding, base pairing, electrostatic interaction, and metal coordination depending on the type of linker and the types of affinity elements. Selection of an appropriate linker for use in the synthetic antibodies of the invention is well within the level of skill in the art based on the teachings herein. The linker can be rigid or flexible, depending on the desired characteristics of the linker, as described in more detail below.

Ideal linking can produce an affinity the product of the two individual binding constants of the affinity elements. One approach to this is to make a collection of each pair of affinity elements, such as polypeptides, that bind different sites bound at different distances on one or more linkers and then measure the affinity of each linked pair of affinity elements to the target (this is discussed in more detail below). Those binding cooperatively will have much higher affinity for the target. One could also mix the different constructions, incubate them with the target and then remove and wash the target (for example on nickel beads if the target were histidine tagged). The synthetic antibodies binding from the mixture would be the ones with the optimal spacing of the individual affinity elements. The identity of the high affinity binding synthetic antibody could be determined directly by mass spectrometry or indirectly by including an identifying tag on each construct.

In the process of carrying out this procedure we have noted an unexpected phenomenon. Combinations of some affinity elements will create a synthetic antibody that has an increase in affinity and specificity of about 10 fold. However, this increase is not distance sensitive, although polypeptide affinity elements do not show the increase if they are less than 1 nm apart from each other in the synthetic antibody. We interpret this type of response as a "caging" of the target as opposed to true cooperative binding. The increase in affinity is due we think basically to creating a high local concentration of binding sites that the target bounces between.

In one embodiment, an optimal linker distance provides a spacing of between about (+/−5%) 0.5 nm and about 30 nm between a first affinity element and a second affinity element. In various further embodiments, the spacing is between about 0.5 nm-25 nm, 0.5 nm-20 nm, 0.5 nm-15 nm, 0.5 nm-10 nm, 1 nm-30 nm, 1 nm-25 nm, 1 nm-20 nm, 1 nm-15 nm, and 1 nm-10 nm.

In another embodiment, a net charge of the resulting synthetic antibody at a pH 7 is between +2 and −2, particularly when the affinity elements comprise or consist of polypeptides. The inventors have discovered that synthetic antibodies with this characteristic tend to work better than those without this characteristic.

In another embodiment, the synthetic antibody binds to the target non-specifically. The inventors have surprisingly discovered that some synthetic antibodies developed through binding to a given target show high affinity binding (ie: nM) to other targets as well (see examples below). In this embodiment, the synthetic antibody can be used to selectively target multiple targets, or target specificity can be modified by techniques known to those of skill in the art. For some applications it may be desirable to create synbodies with even higher or otherwise altered affinity or selectivity. Thus, in a further and completely optional embodiment of the different aspects of the invention, the methods further comprise optimizing binding affinity of one or both of the first affinity element and the second affinity element for the target. Such optimization may be desired to produce even higher affinity binding or specificity synbodies or synbodies with specific affinities or selectivities in any range tailored for a particular application (e.g., reversible binding to a chromatographic material). In one embodiment, the optimization is carried out on a substrate, which is not possible with standard antibodies. Any techniques for optimizing the affinity of the synthetic antibody for the target can be used.

In one non-limiting example of a polypeptide-based synbody, one or both of the polypeptides in the synbody is subjected to array alanine scanning An array is synthesized such that each amino acid in the starting sequence is changed to alanine (or any other amino acid as suitable) one by one. The original target protein is then bound to the array. If the particular amino acid is important for binding, it will bind to the target less well when substituted with alanine (assuming it was not alanine to begin with). This procedure will identify the critical amino acids. The amino acids that need to be optimized may or may not be the ones most strongly affected by the alanine substitutions. Often the alanine substitutions in combination with structural analysis suggest other amino acids or regions of the polypeptide that could be optimized. Once the critical amino acids are identified by this method, a new set of polypeptides with substitutions of the 20 different amino acids at the alanine critical or non-critical sites can be synthesized. These sets of polypeptides can be assayed against the target to find new ones with the improved characteristics. When using larger arrays (30,000 or more) it is actually possible to use a more sophisticated initial scan if desired. For example, all possible pairs of amino acids within the 17 variable positions in the polypeptide can be replaced with all combinations of 10 amino acids (there are 27,200 such polypeptides). This allows one to recognize amino acids that are in themselves important, and also to find pairwise or compensatory interactions as well that can enhance the binding. In many cases, this pairwise approach may alleviate the need for subsequent optimization (by providing substantial local optimization in itself). In other cases, it will simply determine which amino acids should be included in the subsequent optimization rounds as described below. It will be apparent to those skilled in the art based on the teachings herein that there are many variations of this approach possible for an initial screen to locate important structure/function elements of the polypeptides. This may include varying a different number of the amino acid positions at a time (more than 2), changing the number of amino acids tested per position, including non-natural amino acids or amide linked monomers into the polypeptide, creating truncations and deletions instead of substitutions, etc.

The optimization methods may further comprise constructing an array that has a wide variety of amino acids (natural or unnatural) substituted at each critical site. For example, if there were 3 critical amino acids indicated by the alanine scanning, and 20 amino acids variants were used at each of these sites, an array would consist of 8,000 polypeptides. The target protein is then applied to this array. Binding relative to the original polypeptide is compared. The selection on these arrays can be geared towards improved affinity and or specificity. Once selected, the improved polypeptides can be reinserted into the synbody to produce higher or otherwise modified affinity, selectivity, and/or kinetics of binding. For example, it may be desirable to set the affinity at a specific value. This is particularly true for applications associated with chromatography, staining of cells and sensor systems where dynamic binding is useful, and it would thus be desirable to generate synbodies that reversibly bind a target. In fact, the key issue may be to adjust the on and off times rather than the affinity. This can be done by kinetic studies of binding and release. Such studies can be done on the arrays with the proper equipment.

Those of skill in the art will recognize, based on the teachings herein, alternative methods to optimize the synbody. For example, a phage, mRNA display or yeast/bacterial display system could be used to detect the better binders. As an example for mRNA display, a chip with 4000 oligos can be purchased that would have 16 different amino acid encoded substitutions at 3 sensitive positions. These would be primed with a T7 containing primer to make fragments that can be in vitro transcribed/translated to make the polypeptide attached to its encoding mRNA. This library can be panned against the target protein to select the improved binders.

In various embodiments, the methods further comprise connecting to the synthetic antibody further affinity elements (third affinity element, fourth affinity element, etc.) that bind to the first target or other targets. In embodiments where one or more further affinity elements bind to the same target as the first and second affinity elements, the one or more further affinity elements may be connected to the first and/or second affinity element by the linker, or may be connected to the first and/or second affinity element by a one or more further linkers (second linker, third linker, etc.), which may be a further linker or may comprise or consist of a different class of compound. Where multiple linkers are used, the spatial arrangement between affinity elements connected by different linkers can be the same or different. In various further embodiments where the further affinity elements bind to the same target as the first and second affinity elements, the linker or further linker(s) provides a spatial arrangement of the further affinity element(s) to the first and the second affinity element that increases a binding affinity and/or specificity of the synthetic antibody for the target relative to a binding affinity and/or specificity of the further affinity elements for the target.

Thus, the methods for making synbodies as disclosed herein can be used to make, for example, any of the synbody embodiments disclosed herein, including but not limited to those disclosed in FIGS. 1-8, and which are discussed in detail below).

In another embodiment, the invention provides synthetic antibodies made by the methods of this first aspect of the invention. As discussed herein, the structural complexity of the proteome surface space can be covered by ~1000-10,000 or so affinity elements (such as polypeptides or other polymers) that can bind at ~micromolar affinity, and linking them together leads to high affinity and specificity synthetic antibodies, one could make a stock of 1000 or so binders (ie: affinity elements) that could be combined in pairs and linked to quickly make a ligand to anything. Thus, the invention further comprises a pool of affinity elements isolated according to the methods of the invention. The stocks could be pre-made in at large quantities so production could be immediately initiated. Recall that an antibody diversity of ~$10^7$ per person is capable of binding to almost anything. 1000 binders would represent $10^6$ pairs and if they can be linked in 10 different ways this stock would represent $10^7$ ligands. The equivalent of antibody diversity could be stored on the shelf for rapid, inexpensive production.

In a second aspect, the present invention provides synthetic antibodies, comprising:

(a) a first affinity element that can bind a first target;

(b) a second affinity element that can bind the first target, and which can bind to the first target in the presence of the first affinity element bound to the first target; and (c) a linker connecting the first affinity element and the second affinity element, wherein one or both of the first affinity element and the second affinity element have a molecular weight of at least 1000 Daltons;

wherein at least one of the first affinity element and the second affinity element are not derived from the first target;

wherein the synthetic antibody has an increased binding affinity and/or specificity for the first target relative to a binding affinity and/or specificity of the first affinity element for the first target and relative to a binding affinity and/or specificity of the second affinity element for the target; and wherein the first target is not an Fv region of an antibody.

Synthetic antibodies according to this aspect of the invention can be obtained against any target or targets of interest, and can generally bind to the target(s) both in solution and on surfaces, thus increasing the range of applications for their use. The spatial arrangement (ie, specific spacing and/or orientation) of the affinity elements in the synbodies improves affinity for a target relative to the affinity of the individual affinity elements for the target, and thus the synthetic antibodies are suitable for a wide variety of uses, including but not limited to ex-vivo diagnostics, for example in standard ELISA-like formats or in multiplex arrays; in vivo as imaging agents or as therapeutics for specific indications; as binding agents for affinity separation techniques and reagents, including but not limited to affinity columns and affinity beads; as detectors for environmental or biological agents; and as catalysts for chemical reactions. As therapeutics, the synthetic antibodies can be used to bind a target or for mediating binding and uptake in specific cells or as "smart drugs" for drug delivery.

As used herein, an "increased binding affinity and/or specificity of the synthetic antibody" means any increase relative to the binding affinity and/or specificity of the first affinity element for the first target and relative to a binding affinity and/or specificity of the second affinity element for the target. In various embodiments, the increase is 10-fold, 100-fold, 1000-fold, or more over either individual element.

In a further embodiment, one or both of the first and second affinity elements have a molecular weight of between about 1000 Daltons and 10,000 Daltons. In one embodiment, polypeptide compounds for use in the methods of this aspect of the invention are between about 1000 Daltons and 4000 Daltons (up to approximately 30 amino acid residues). In another embodiment, nucleic acid aptamers of up to 10,000 Daltons are used (ie: approximately 30 bases).

Synbodies according to the present invention can be of any suitable size, based on the sizes of the affinity elements and linkers used.

Affinity elements (ie: compounds identified as being affinity elements for a target of interest), targets, linkers, and other terms used in this second aspect have the same meaning as described above in the first aspect of the invention. Furthermore, all embodiments disclosed in the first aspect of the invention can be used in this second aspect of the invention.

In one embodiment, at least one of the first affinity element and the second affinity element are not the Fv portion of antibodies or antigen-binding portions thereof; in a further embodiment, neither the first nor the second affinity elements are the Fv of antibodies or antigen-binding portions thereof. The first target is not the Fv of an antibody. In further embodiments, the first target is not an antibody, an antibody bearing cell, or an antibody-binding cell surface receptor (or portion thereof suitable for antibody binding)

Within a given synthetic antibody, the first and second affinity elements can be the same class of compound (ie: nucleic acids, polypeptides, etc.), or they can be different types of compounds. For example, the first affinity element can comprise or consist of a nucleic acid and the second affinity element can comprise or consist of a polypeptide. In one embodiment, one or both of the first and second affinity elements comprise or consist of polypeptides. Those of skill in the art will recognize a wide variety of affinity element combinations according to the present invention. In one embodiment, one or both of the first and second affinity elements comprises or consists of a non-naturally occurring compound, as discussed in the first aspect of the invention. In further embodiments, one or both of the first and second affinity elements does not comprise or consist of a nucleic acid.

In one embodiment, one or both of the first and second affinity elements, prior to inclusion in the synthetic antibodies of this aspect have dissociation constant for binding to the first target of between about 1 µM and 500 µM. Linkage of the first and second affinity elements provides a synthetic antibody with an increased affinity and/or specificity for the first target relative to a binding affinity and/or specificity of the first affinity element for the first target and relative to a binding affinity and/or specificity of the second affinity element for the target. Thus, the synthetic antibodies of the present invention combine two weaker binders by linking them; as discussed above, one surprising discovery herein is that the structural space represented on the surface of proteins is covered by a small number of 20 amino acid polypeptides. This allows using a small number of affinity elements to cover enough space to give ~micromolar Kds on two or more sites per target. An added advantage is that using these relatively larger molecules makes it less likely that the linker attachment will disrupt the binding of the resulting synbody to the first target.

In various embodiments, the first affinity element and the second affinity element prior to inclusion in the synthetic antibody have dissociation constant for binding to the first target of between about 1 µM-500 µM; 1 µM-150 µM; 10 µM-500 µM; 25 µM-500 µM; 50 µM-500 µM; 100 µM-500 µM; 10 µM-250 µM; 50 µM-250 µM; and 100 µM-250 µM.

In one embodiment, an optimal linker distance provides a spacing of between about 0.5 nm and about 30 nm between a first affinity element and a second affinity element. In various further embodiments, the spacing is between about 0.5 nm-25 nm, 0.5 nm-20 nm, 0.5 nm-15 nm, 0.5 nm-10 nm, 1 nm-30 nm, 1 nm-25 nm, 1 nm-20 nm, 1 nm-15 nm, and 1 nm-10 nm. Those of skill in the art can design linkers for appropriate spacing based on the teachings herein.

In another embodiment, a net charge of the synthetic antibody at a pH 7 is between +2 and −2, particularly when the affinity elements comprise or consist of polypeptides. The inventors have discovered that synthetic antibodies with this characteristic tend to work better than those without this characteristic.

While the synthetic antibodies of the invention comprise first and second affinity elements, they can comprise further such affinity elements (ie, third affinity element, fourth affinity element, etc.), as discussed in more detail below.

As discussed above, the synthetic antibody has an increased affinity and/or specificity for the first target relative to a binding affinity and/or specificity of the first affinity element for the first target and relative to a binding affinity and/or specificity of the second affinity element for the target. For example, the arrangement of the first and second affinity elements may increase affinity of the resulting synthetic antibody for a monomeric target (See, for example, FIG. 2). Alternatively, the arrangement of the first and second affinity elements may increase affinity and specificity of the synthetic antibody for a homodimeric or heterodimeric target, where the individual affinity elements would otherwise only be able to bind to a monomer (See, for example, FIG. 3).

The first and second affinity element bind to the first target, and their binding to the target is not exclusive, generally by virtue of the first and second affinity elements binding to different regions on the target. For example, where the target is a single structure, the first and second affinity elements may bind to different sites on the target (See, for example, FIG. 2). Alternatively, where the target is a homodimer, the first and second affinity elements may be identical and bind to the same location but one to each monomer in the homodimer (See, for example, FIG. 3, left panel). In a further example, where the target is a heterodimer AB, the first affinity element can bind to A and the second affinity element can bind to B (See, for example, FIG. 3, right panel). Those of skill in the art will recognize many variations based on the present disclosure. The targets for the affinity elements can be at distances not attainable by conventional antibodies. This distance can be to two different targets, as noted.

As used herein, "binding" of affinity elements to a target refers to selective binding in a complex mixture (ie: above background), and does not require that the binding be specific for a given target as traditional antibodies often cross-react. The extent of acceptable target cross-reactivity for a given synthetic antibody depends on how it is to be used and can be determined by those of skill in the art based on the teachings herein. For example, methods to modify the affinity and selectivity of the synthetic antibodies are described herein.

In various embodiments, the synthetic antibodies of the invention can comprise further affinity elements (third affinity element, fourth affinity element, etc.) that bind to the first target or other targets. The one or more further affinity elements may be connected to the first and/or second affinity element by the linker, or may be connected to the first and/or second affinity element by a one or more further linkers (second linker, third linker, etc.), which may comprise or consist of a different class of linker compound. Where multiple linkers are used, the spatial arrangement between affinity elements connected by different linkers can be the same or different. In various further embodiments the binding affinity and/or specificity of the resulting synthetic antibody for any further is increased relative to a binding affinity and/or specificity of the further affinity elements for the target.

Figures 4A, 4B:
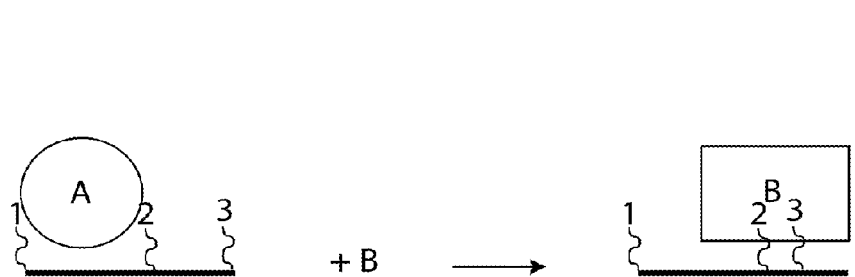
FIG. 4(a-b). Schematic of synbodies that act as chemical OR gates or switches.

Various further embodiments of synthetic antibodies according to this second aspect of the invention include, but are not limited to those provided in the Figures as follows:

FIG. 4: In this example, the synthetic antibody comprises affinity element 1 that binds to target A, affinity element 2 that binds to targets A and B, and affinity element 3 that binds to target B. The spatial arrangement of the 3 affinity elements by the linker provides that only one of targets A and B can be bound by the synthetic antibody. In one non-limiting embodiment, the $K_d$ of binding of target A is decreased by the $K_d$ of binding of B. In this particular example, the binding is competitive and a rigid linker, such as a nucleic acid linker, can be used. This synbody acts a chemical OR gate, or to control the binding of one target by the presence of another. As will be clear to those of skill in the art, this can be generalized to 3 or more targets, for example, by using additional affinity elements.

Figure 5:
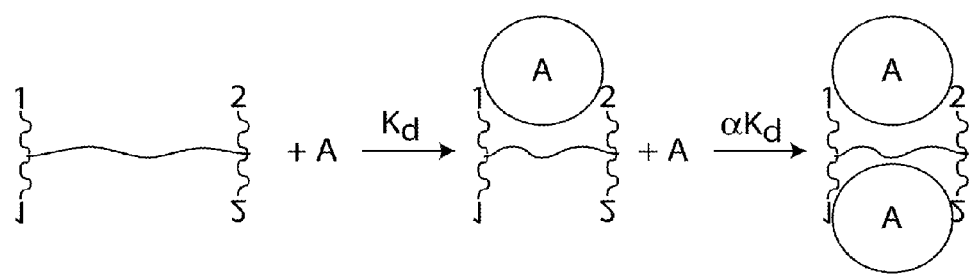
FIG. 5. Schematic of synbodies that bind multiple A molecules cooperatively (a#1, either positive or negative cooperativity).

FIG. 5: In this example, the synthetic antibody comprises affinity elements 1 and 2 that bind to target A. Further affinity elements 3 and 4 are spatially arranged by the linker to affinity elements 1 and 2 to provide cooperative binding of a second target molecule A. For example, the dissociation constant for binding of the second target molecule A is less than or greater than that of the dissociation constant for binding of the first target molecule A—thus, positive or negative cooperativity is possible though only positive cooperativity is shown in the figure. This allows one to alter the binding curve for a particular target molecule, making it super- or sub-linear at low concentrations. This can be used, for example, to generate high contrast ratio measurements between low and high concentrations of the target.

Figure 6:
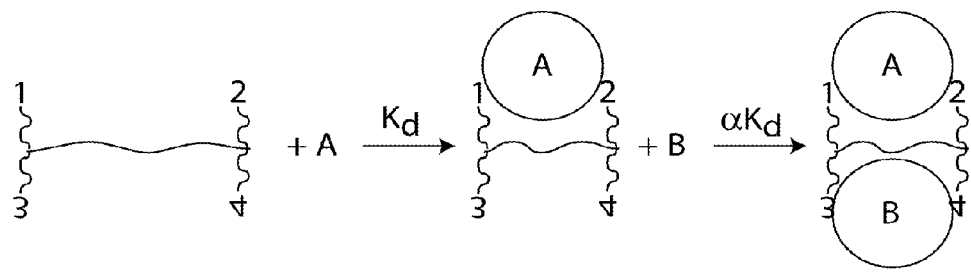
FIG. 6. Schematic of synbodies that bind multiple different molecules cooperatively (a#1, either positive or negative cooperativity).

FIG. 6: In this example, the synthetic antibody comprises affinity elements 1 and 2 that bind to target A. Further affinity elements 3 and 4 are spatially arranged by the linker to affinity elements 1 and 2 to provide cooperative binding of target molecule B. This is similar to FIG. 5 except that the cooperative binding (positive or negative) is between two different target molecules. This is another way of allowing B to influence the binding curve of A or the other way around. Unlike the case in FIG. 4, the interaction is not competitive, but is more like an allosteric affector in an enzyme system.

Figure 7:
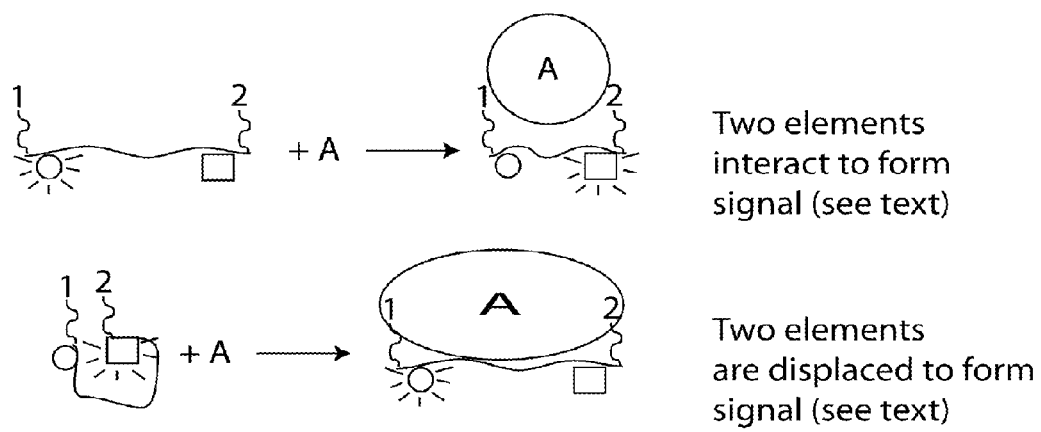
FIG. 7. Schematic of synbodies that act as signaling molecular sensors; (a) two elements interact to form signal; (b) two elements are displaced to form signal.

FIG. 7: The ability to design conformational or functional changes in the synbodies of the present invention upon binding and/or alter the environment of a sensor molecule upon binding is a unique capability of synbodies that cannot easily be designed into antibodies or individual ligand systems. In this example, the synthetic antibody comprises affinity elements 1 and 2 that bind to target A, and wherein binding of A to affinity elements 1 and 2 results in a spatial arrangement of two previously separated signaling elements (depicted as a circle and a square in the figure) that leads to a change in signal indicating presence of target A. The signaling elements can, for example, comprise or consist of two (or more) fluorophores that interact via fluorescence resonant energy transfer or one fluorophore and a quencher (acting either via energy transfer or electron transfer). Other interactions between a fluorophore and a second molecule or simply another part of the synbody can be designed that change the emission intensity, wavelength, spectral distribution, polarization or excited state dynamics of the fluorophores upon binding to the target. It is also possible for such conformational changes to alter the absorbance properties of the fluorophores. In other embodiments, the signaling elements can comprise or consist of one or two (or more) electrochemical sensor molecules that interact to change the observed midpoint potential or other aspects of the current voltage relationship of one or more of the molecules. Conformational changes of this kind can be directly observed via methods that measure the change in index of refraction (e.g., surface plasmon resonance) or change the surface properties of the material and thus the optical behavior at the interface (nonlinear methods such as second harmonic generation). In further embodiments, the signaling elements can comprise or consist of a series of donor and acceptor signaling molecules that are all too far apart for energy transfer to occur initially, but upon binding of multiple target molecules (can either be the same or different targets) become close enough together to form an energy (or electron) transfer network. This makes signal generation nonlinear and correlated with binding of multiple molecules (either the same or different).

Figure 8:
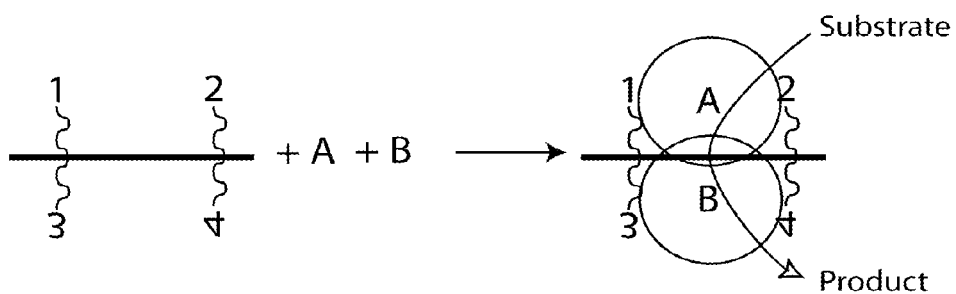
FIG. 8. Schematic of synbodies acting as actuators of enzyme activity (homo or heteromultimer).

FIG. 8: In this example, the synthetic antibody comprises affinity elements 1 and 2 that bind to target A. Further affinity elements 3 and 4 are spatially arranged by the linker to affinity elements 1 and 2 to self-assemble a complex of Targets A and B. This example demonstrates the ability of the syn bodies of the invention to organize multiple components to direct the assembly of enzymes or other functional systems from component parts. There are many variations on this theme. In this figure, two targets are brought together to form an enzyme by binding to the synbody. Variations include, but are not limited to, bringing two subunits in close contact for some function other than catalysis, or where binding decreased enzyme activity or other functional activity. This system provides a flexible template for programming enzymatic or other functional activity in the same sense that an operon serves as a template for interactions between proteins that ultimately control gene transcription. All the same kinds of binding-based control approaches seen in transcription or other enzymatic control systems can be used here. Such systems could be used to amplify a binding signal (in the same sense as an ELISA), or to control the activity of an enzyme using in a chemical, biochemical or biomedical process.

The synthetic antibodies of the invention can be present in solution, frozen, or attached to a substrate. For example, a library of synthetic antibodies can be produced, and arrayed on a suitable substrate for use in various types of detection assays. This provides a distinct advantage over conventional antibodies, most of which do not work in array based applications. Thus, in another embodiment, one or more synthetic antibodies of the invention are bound to a surface of a substrate, either directly or indirectly. The substrate can comprise an addressable array, where the identity and location of each synthetic antibody on the array is known. Examples of such suitable substrates include, but are not limited to, microarrays, beads, columns, optical fibers, wipes, nitrocellulose, nylon, glass, quartz, mica, diazotized membranes (paper or nylon), silicones, polyformaldehyde, cellulose, cellulose acetate, paper, ceramics, metals, metalloids, semiconductive materials, quantum dots, coated beads, other chromatographic materials, magnetic particles; plastics and other organic polymers such as polyethylene, polypropylene, and polystyrene; conducting polymers such as polypyrole and polyindole; micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, and other fibrous or stranded polymers. In one exemplary embodiment, the substrate comprises a substrate suitable for use in a "dipstick" device, such as one or more of the substrates disclosed above.

Thus, in a further embodiment, the second aspect of the invention provides a substrate comprising:

(a) a surface; and (b) one or more synthetic antibodies of the second aspect attached to the surface.

The substrate surface can comprise a plurality of the same synthetic antibody, or a plurality of different synthetic antibodies (where each synthetic antibody may itself also be present in multiple copies, and wherein the affinity elements in the different synthetic antibodies may be of different compounds classes (ie: some affinity elements nucleic acid-based; some polypeptide-based, etc.) When bound to a solid support, the synthetic antibodies can be directly linked to the support, or attached to the surface via known chemical means. In a further embodiment, the synthetic antibodies can be arrayed on the substrate so that each synthetic antibody (or subset of synthetic antibodies) are individually addressable on the array, as discussed herein. Thus, the substrates and/or the synthetic antibodies can be derivatized using methods known in the art to facilitate binding of the synthetic antibodies to the solid support, so long as the derivitization does not interfere with binding of the synthetic antibody to its target. The substrates may further comprise reference or control compounds or elements, as well as identifying features (RFID tags, etc.) as suitable for any given purpose.

In a third aspect, the present invention provides methods for making synthetic antibodies (according to any of the synbody embodiments disclosed herein), comprising connecting at least a first affinity element and a second affinity element for a given target via a linker;

wherein the second affinity element can bind to the target in the presence of the first affinity element bound to the target;

wherein one or both of the first affinity element and the second affinity element have a molecular weight of at least 1000 Daltons;

wherein one or both of the first affinity element and the second affinity element are not derived from the first target;

wherein the synthetic antibody has an increased binding affinity and/or specificity for the first target relative to a binding affinity and/or specificity of the first affinity element for the first target and relative to a binding affinity and/or specificity of the second affinity element for the target; and wherein the first target is not an Fv region of an antibody.

All terms and embodiments disclosed above for the first and second aspects of the invention apply to this third aspect of the invention. Connections between the affinity elements can be of any type, including but not limited to covalent binding, hydrogen bonding, ionic bonding, base pairing, electrostatic interaction, and metal coordination, depending on the type of linker and the types of affinity elements. Selection of an appropriate linker for use in the methods of making synthetic antibodies of the invention is well within level of skill in the art based on the teachings herein. In further embodiments, three, four, or more affinity elements can be physically connected by one, two, or more linkers. In each of these embodiments, the affinity elements may all be of the same compound type (nucleic acid, protein, etc.), different, or combinations thereof. In various further embodiments, the further affinity elements may bind to the same target or to one or more different targets than the target bound by the first and second affinity elements. When more than one linker is used, the linkers may all be of the same compound type (nucleic acid, protein, etc.), different, or combinations thereof.

The advantages of synthetic antibodies made by the methods disclosed herein are discussed above. In one embodiment, the methods comprise determining an appropriate spacing between the affinity elements (ie: first affinity element and second affinity element; first-second-third affinity element, etc.) in the affinity element combination. An appropriate linker distance is one that optimizes the affinity and/or specificity of the resulting synbody. Any suitable technique for determining an appropriate spacing can be used. In one non-limiting example, a predetermined set of linkers that cover increments up to 100 nm are generated, and the affinity elements are connected to each linker and the optimal distance determined using appropriate binding assays. The linker could be a derivatized PEG for example, but can be of any suitable type that can be used to determine optimal spacing, as discussed in detail above and in the examples that follow.

In another embodiment, determining optimal spacing involves systems in which in situ synthesis of linkers on a surface is used such that a series of compounds, (for example, polyalanine peptides) is made with two variably spaced lysines, differentially blocked, such that subsequent bulk attachment of the two peptides (unblocking one lysine and then the other) gives a whole range of spacings. Many other variations on this theme are possible using peptides, nucleic acids or a variety of non-natural polymers, heteropolymers, macrocycles, cavities, other scaffolds, and DNA tiling arrays.

Figure 9A:
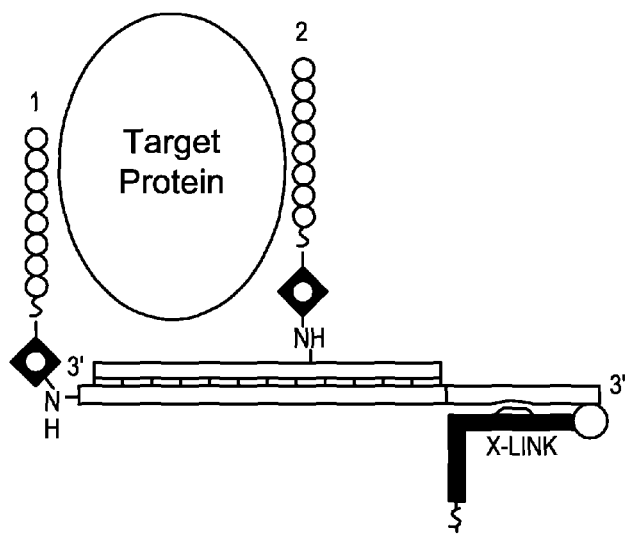
FIG. 9. (a) Representation of synthetic antibody. (b) Construction of mini-library of synbodies with different interpeptide distances. (c) One embodiment of a molecular slide rule composition.
Figure 9B:
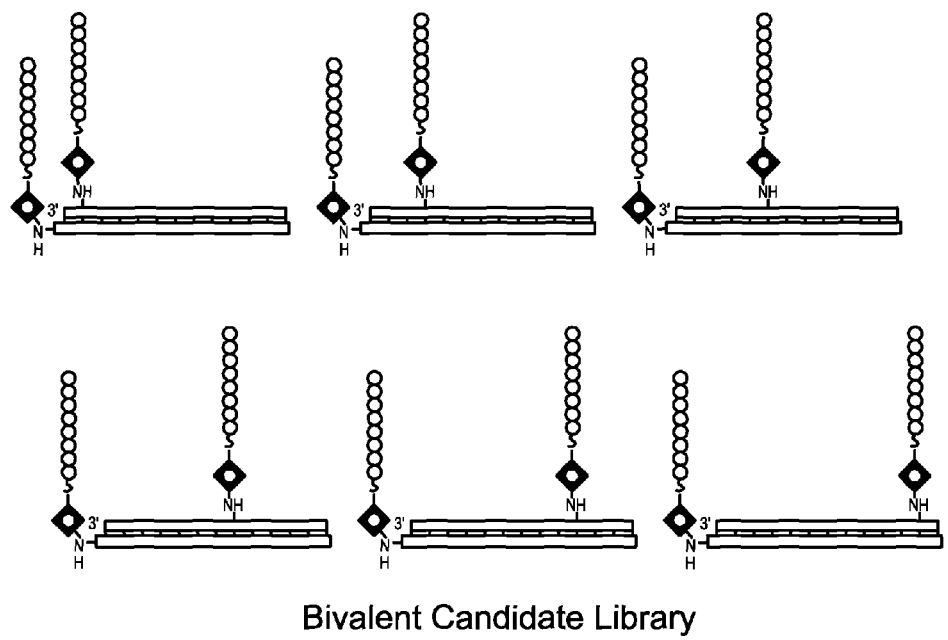
Figure 9C:
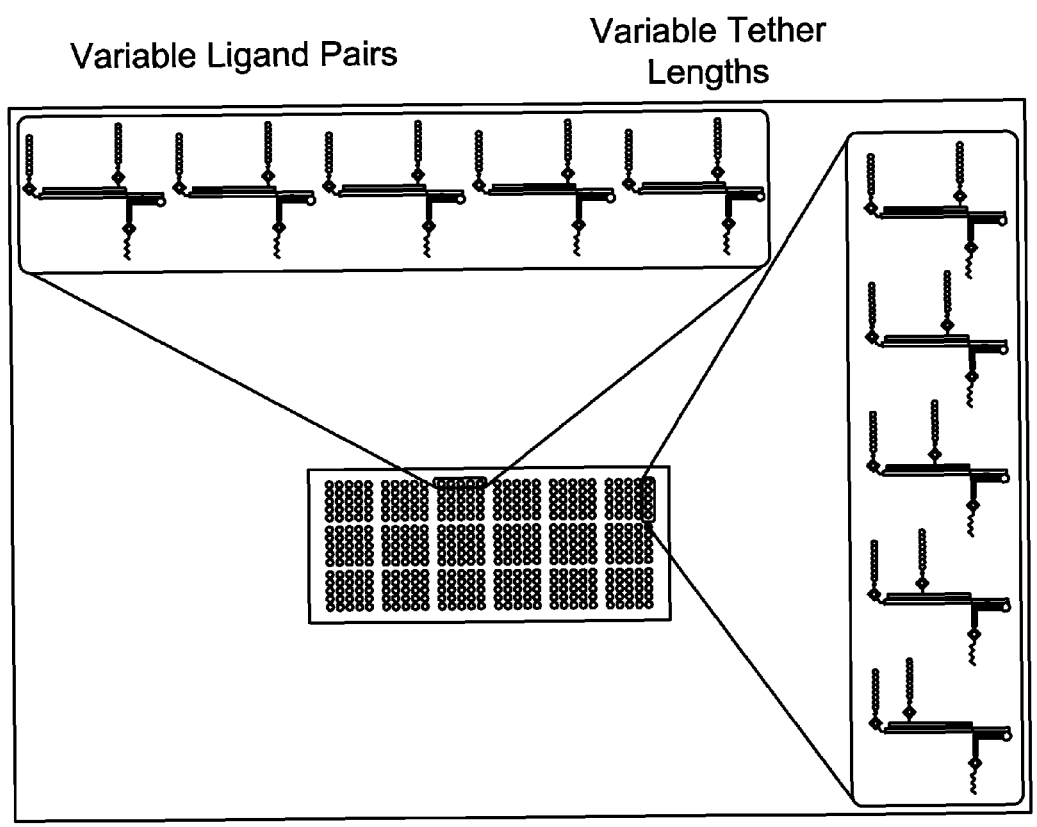

A further method involves using the flexibility of DNA to create a set of matching oligonucleotides to separate two affinity elements at set distances (FIG. 9a). The cassette aspect of this system (as discussed in more detail below) allows ready determination of which affinity elements synergize and at what distance. Detection can be accomplished by any suitable method, including but not limited to SPR electrochemical detection, micromechanical detection (e.g., frequency shifts in resonant oscillators), electronic detection (changes in conductance or capacitance), mass spectrometry or other methods, or by spotting on a slide with florescent detection of the target. An exemplary system for SPR determination is depicted in FIG. 9c. On one slide multiple combinations of polypeptides and their distances can be tested as seen in FIG. 9c. This system is cost effective, simple, available to broad affinity element repertoire, and amenable to high throughput.

Thus, in a fourth aspect, the present invention provides a composition, comprising:

(a) a first affinity element bound to a template nucleic acid strand;

(b) a second affinity element bound to a complementary nucleic acid strand, wherein the first affinity element and the second affinity element non-competitively bind to a common target;

wherein the template nucleic acid strand and the complementary nucleic acid strand are bound to form an assembly;

wherein the first affinity element and the second affinity element are separated in the assembly; and wherein either the template nucleic acid strand, the complementary nucleic acid strand, or both, are bound to a surface of a substrate.

In a further embodiment of this aspect, the composition further comprises the common target bound to the first affinity element and to the second affinity element.

These compositions (also referred to as a "molecular slide-rule") can be used, for example, in the methods of the first, third, and fifth aspects of the invention for determining an optimal spatial separation of affinity elements in a synbody for a given application.

The template nucleic acid strand and the complementary nucleic acid strand are bound to form an assembly; this binding can be of any type, including but not limited to covalent binding and base pairing. One or both of the template nucleic acid strand and the complementary nucleic acid strand are also bound to the substrate surface; this binding can be of any type as discussed above, such as covalent binding, while the template and complementary nucleic acid strands are single stranded nucleic acid; preferably DNA.

Affinity elements and substrates are as disclosed above. As used in this aspect, "separated" means that the affinity elements do not bind each other, but are positioned to permit determination of optimal spacing of the affinity elements to permit binding of the first and the second affinity elements to the target simultaneously. For example, the different versions of the composition have the affinity elements separated by repetitive turns of the DNA helix (ie: the double stranded nucleic acid in the assembly formed by the template nucleic acid strand and the complementary strand base pairing).

In a further embodiment of this fourth aspect, the invention provides an array, comprising a plurality of the compositions disclosed above bound to a substrate surface, wherein the plurality of compositions comprises one or both of:

(a) a plurality of compositions wherein the first ligand and the second ligand are the same for each composition, but wherein the separation of the first ligand from the second ligand in the assembly differs; and (b) a plurality of compositions wherein the first ligand and/or the second ligand are different for each composition.

As used in this aspect, a plurality is 2 or more; preferably 3, 4, 5, 6, 7, 8, 9, 10, or more. The compositions of option (a) are preferred for determining optimal distance between the first and second affinity elements in the synbody, while option (b) is preferred to multiplex the assay Binding of the compositions of the fourth aspect of the invention to the substrate can be by any suitable technique, such as those disclosed herein.

In this fourth aspect, the double stranded nucleic acid is used to template-direct the assembly of different affinity element pairs with programmed nanometer-scale spacing. DNA is an ideal material for developing synthetic architectures due to the fact that it is easy to engineer and self-assembles into highly reproducible structures of known morphology. In one non-limiting example, the template strand is conjugated to affinity element 1 and annealed to a complementary strand which is conjugated to affinity element 2. The system is designed such that affinity element 1 is separated from affinity element 2 by one additional base separations and the repetitive turns of a DNA helix (FIG. 9b). Each base can be used to separate the two affinity agents. For each turn of the DNA helix corresponds to separation distances of roughly 4 nm, 7.5 nm, 11 nm. Each affinity element-pair complex is spotted at independent positions on a surface and the relative or actual binding of the target to each complex is determined by any suitable technique, including but not limited to fluorescence or surface plasmon resonance (SPR).

The compositions of this fourth aspect can be attached to a surface (FIG. 9(c)) in an array format using a psoralen photocrosslinking strategy. This can be done using a psoralen-DNA 'linker' strand that is able to recognize a region of the template downstream of the variable strand. Once the linker strand is annealed to the template, exposure to UV light results in chemical cross linking of the linker strand to the DNA helix containing affinity element 1 and 2. Excess linker strand is then removed from the reaction mixture by affinity separation, and target binding activity and specificity is carried out. Screening can be achieved by traditional fluorescence-based assays whereby the synthetic antibody is attached to a glass slide or to a bead and then screened with fluorescently labeled target. Additionally, the synthetic antibody can be attached to a gold surface and screened with a label-free technique such as SPR, electrochemical detection, micromechanical detection (e.g., frequency shifts in resonant oscillators), electronic detection (changes in conductance or capacitance), mass spectrometry or other methods.

In a fifth aspect, the present invention provides methods for ligand identification, comprising:

(a) contacting a substrate surface comprising a target array with one or more potential ligands, wherein the contacting is done under conditions suitable for moderate to high affinity binding of the one or more ligands to suitable targets present on the substrate; and (b) identifying targets that bind to one or more of the ligands with at least moderate affinity.

The target array can be any array of targets of interest as disclosed herein. In various embodiments, the array may comprise 50, 100, 500, 1000, 2500, 5000, 10,000; 100,000; 1,000,000; 10,000,000 or more targets. In a further embodiment, the target array is addressably arrayed (as disclosed above for compound arrays) for ease in identifying targets that have been bound. Detection of binding can be via any method known in the art, including but not limited to those disclosed elsewhere herein.

The targets may comprise any target class as described herein. In one embodiment, the targets are protein targets. In a further embodiment, the target array comprises a range of different protein targets, for protein targets not all related based on minor variations of a core sequence. In a further embodiment, the targets are not antibodies or Fv regions of antibodies. In further embodiments, the first target is not an antibody, an antibody bearing cell, or an antibody-binding cell surface receptor (or portion thereof suitable for antibody binding)

Similarly, the potential ligands can be any suitable potential ligand as disclosed herein (ie: compounds or affinity elements). In various embodiments, the potential ligand comprises a synthetic antibody according to any aspect or embodiment of the present invention. In a further embodiment, the potential ligand may be one for which a target specificity has not previously been established.

All terms and embodiments disclosed above apply equally to this aspect of the invention. In embodiments where the synthetic antibodies of the invention are used, the one or more synthetic antibodies to be screen as potential ligands comprise a first affinity element and a second affinity element, wherein one or both of the first affinity element and the second affinity element have a molecular weight of at least about 1000 Daltons; in further such embodiments, one or both of the first and second affinity elements comprise or consist of polypeptides Alternatively, the candidates could be constructed from rational design of the ligands or even from random sequences.

For artificial antibodies the starting point is almost always the protein or other target. A library of variants (single chain antibody clones, phage display of peptides, aptamer libraries, etc.) is screened against the protein target. A single clone or consensus of sequences is isolated as the specific ligand to a specific target. In all these types of examples, the starting point is a particular target for which a ligand is isolated.

In contrast, this aspect of the invention turns this standard procedure for creating ligands on its head. We first create one, a few or a library of potential ligands. For example, we create a synbody (using, for example, the methods disclosed above) consisting of two 20 mer polypeptides of random (non-natural) sequence linked by a linker. In one non-limiting embodiment, the synbody has the two different polypeptides linked about 1 nM apart. The synbody is labeled and then reacted with an array with 8000 human proteins. A protein is identified that the synbody binds with high affinity and specificity. In this way a very good synthetic antibody is isolated for that particular protein. A unique aspect of this invention is that the usual process is reversed—a potential ligand is made and then a library of targets is screened for a target that is appropriately reactive.

This system is amenable to high throughput or even massively parallel screening. For example, a large number of potential ligands can be constructed by combining various binding elements, linkages, and spacing distances using, for example, the methods and synthetic antibodies disclosed above. These could be mixed (or prepared by combinatorial methods) and reacted with a large number of targets. The ligand on each target could be identified by any suitable technique, including but not limited to mass spectrometry, bar coding or mixed fluorescent tags. An advantage of this system is that it not only determines the affinity of the ligand for a particular target, but also the off-target reactivities to all the other proteins on the array.

This approach defies conventional wisdom, which would suggest that the space of possible target shapes is far too large for a screening strategy of this kind to produce synbodies having antibody-like affinities and specificities. While not being bound by a specific mechanism, the inventors believe (as described above) that there are a very limited number of distinct substructures on the surface of proteins. That is, unlike sequence space, the structural space represented on the surface of proteins is very limited. Proteins have a limited number of shapes on their surface. A second aspect of the hypothesis is that a small number of appropriately chosen ligands can represent the structural complements of all the shapes present on protein surfaces. For example, 5,000 20-amino acid polypeptides of non-life sequence can provide most complementary shapes. A third aspect is that if two of these shape binding elements are held at a fixed distance, the resulting synbody is likely to find, in a library of reasonable size, some protein having complementary shapes at that distance, and will bind that protein in a cooperative fashion and with high specificity.

In various further embodiments of this aspect of the invention are methods for screening the antibodies and synbodies on a protein microarray in a manner that reduces the number of (very expensive) microarrays required for screening a given number of candidates. In one non-limiting example, affinity data is read using a real-time microarray reader with the protein microarray mounted in a flow chamber. Buffer containing a single antibody or synbody in very low concentration is flowed over the microarray until binding is detected on a small number of targets; these will be the highest affinity targets for that antibody or synbody. Since the antibody or synbody has very low affinity for all but the few targets for which it is specific, and since the antibody or synbody is applied at very low concentration and the flow stopped after binding is detected, nearly all targets will remain unoccupied and even the occupied targets will be far from saturation. The process can then be repeated with a second antibody or synbody, thereby obtaining maximum benefit from the protein array.

In another embodiment, the methods of this aspect of the invention can be used to identify new targets for existing antibodies, including therapeutic, diagnostic, and research antibodies. As disclosed below, the methods provide valuable information on the specificity of such antibodies in a high throughput and low cost manner, and allow identification of antibodies specific for targets for which antibodies are currently unavailable.

In a sixth aspect, the present invention provides methods for identifying a synthetic antibody profile for a test sample of interest, comprising contacting a substrate comprising a plurality of synthetic antibodies according to the present invention with a test sample and comparing synthetic antibody binding to the test sample with synthetic antibody binding to a control sample, wherein synthetic antibodies that differentially bind to targets in the test sample relative to the control sample comprise a synthetic antibody profile for the test sample.

As used in this aspect, a plurality means 2 or more; preferably 50, 100, 250, 500, 1000, 2500, 5000, or more. The test sample can be any sample of interest, including but not limited to a patient tissue sample (such as including but not limited to blood, serum, bone marrow, saliva, sputum, throat washings, tears, urine, semen, and vaginal secretions or surgical specimen such as biopsy or tumor, or tissue removed for cytological examination), research samples (including but not limited to cell extracts, tissue extracts, organ extracts, etc.), or any other sample of interest. Such a patient sample can be from any patient class of interest. The control sample can be any suitable control, such as a similar tissue sample from a known normal, or any other standard. Thus, the methods can be used, for example, as a diagnostic, prognostic, or research tool. In one embodiment, the control sample is contacted with the same substrate as the test sample; in another embodiment, the control sample is contacted with a different but similar or identical substrate as the test sample.

In this aspect, a plurality of synthetic antibody candidates (ie: 10, 20, 50, 100, 250, 500, 1000, 2500, 5000 or more) are arrayed in an addressable fashion, for example on a printed slide. The ligands in the candidates could be from pre-selected sequences, rational design or random sequence. These arrays would then be used to screen samples of interest. For example they could be serum from normal and affected subjects. Synthetic antibodies that bound components of the serum and ones that differentially bound components between the two samples could be selected. The actual target or targets bound by each synthetic antibody could be determined directly from the array by mass spectrometry or by using the synthetic antibody as and affinity agent to purify the targets.

Any one or all of the steps of the methods of the different aspects of the invention can be automated or semi-automated, using automated synthesis methods, robotic handling of substrates, microfluidics, and automated signal detection and analysis hardware (such as fluorescence detection hardware) and software.

Thus, in another aspect, the invention provides computer readable storage media comprising a set of instructions for causing a signal detection device to execute procedures for carrying out the methods of the invention. For example, the procedures comprise the signal processing, target affinity element identification steps and databasing of the second aspect of the invention, and any/all embodiments thereof The computer readable storage medium can include, but is not limited to, magnetic disks, optical disks, organic memory, and any other volatile (e.g., Random Access Memory ("RAM")) or non-volatile (e.g., Read-Only Memory ("ROM")) mass storage system readable by a central processing unit ("CPU"). The computer readable storage medium includes cooperating or interconnected computer readable medium, which can exist exclusively on the processing system of the processing device or be distributed among multiple interconnected processing systems that may be local or remote to the processing device.

The invention further provides kits, comprising any one or more of the reagents disclosed herein. Such kits can be used, for example, for selecting affinity elements and making synbodies out of them, using the methods disclosed herein.

Example 1

In one non-limiting embodiment of this second aspect of the invention, an array of 4,000 polypeptides is spotted on a slide. Each polypeptide is 20 amino acids in length, and is spotted such that its orientation is controlled to be through the C-terminus. A large amount of sequence and chemical space can be adequately sampled using only a small fraction of the possible space. For example, in the case of this array, there are $19^{17}.5 \times 10^{21}$ possible polypeptide sequences (the first 3 amino acids are held constant, but this is not necessary and cysteine is used only at the C-terminus as attachment via a thiol), but we sampled just $4 \times 10^3$ sequences and can identify polypeptides that show moderate binding affinity and specificity to a number of proteins.

The target protein is labeled with a florescent dye and incubated with the array. Polypeptides that bind the target protein are determined. Alternatively, we have incubated unlabelled affinity tagged form of the target protein and detected binding by virtue of a secondary antibody against the tag. Each sequence of the polypeptides on each spot is already known; thus, the process is a screen for elements, not a selection. Thus, the process of ligand discovery is limited only by the rate at which individual targets can be screened on pre-printed polypeptide arrays. In this sense it is distinct from aptamer, phage or other panning methods, in which recurrent selections using unknown sequences are required, and only those elements that do bind a target are determined, while those that do not bind are not known.

Whether such a small sequence space can yield effective binders depends on how the binding space is shaped. If the slope of relative binding affinity is very steep around the optimal polypeptides, it is unlikely that one of the 4,000 polypeptides will be close to one of the optimal polypeptides. If however, the slope of the binding space is gradual, one may find polypeptides that are on the "side of the mountain." If the determination of the optimal polypeptide is by virtue of sequence similarity, it is very unlikely that in 4000 polypeptides ones with sequence similar to the optimal would be found in the $10^{21}$ possibilities (for 17 mer polypeptides).

Most experts in this field thought this process would not work—but it does. Consistent with the logic above, most of the polypeptides that bind a particular site on a protein do not resemble each other in sequence. Therefore, while not being bound by any hypothesis, we suggest the following explanation, which represents a new insight into peptide sequence space. We propose that the $10^{21}$ possible 17 mer polypeptides actually form a very limited number (~4000) of structural forms. This view has several important predictions and implications. First, the space dimension would be much smaller. Therefore, around each optimal sequence would be structurally related polypeptides on the side of the mountain that would not necessarily have any sequence similarity. Second, several proteins may bind to a specific peptide but that peptide could be varied to bind better to one or the other. In other words, the same 4000 polypeptides may be all that is needed to generate synbodies to virtually an unlimited number of targets.

Once a set of affinity agents are isolated for a given target we may use these directly or use them to create an artificial antibody. For the latter we identify two or more elements that bind different sites on the targets. To do so we can, for example, block target binding with the target polypeptides or co-spot them on slides or we can put pairs onto DNA linkers to determine pairs and spacing simultaneously (FIG. 9c). The pairs of affinity elements may be valuable in themselves.

We then create a synbody using the system for measuring as described. A first affinity element is covalently attached to a DNA template strand, and separately attaching affinity element two to different nucleotide positions on a complementary strand. We anneal the two strands of DNA and immobilize the complex to 400 different sites on a surface plasmon resonance (SPR) Flexchip. We then flow the target of interest over the surface to identify different ligand pairs and ligand pair separation distances with enhanced binding. Ligand pairs and ligand pair separation distances with the greatest binding enhancement are either used directly or reconstructed with synthetic tethers based on the distance parameter determined in the SPR analysis. We have used this process to generate a synbody to Ga180 that exhibits enhanced binding as described in detail in Example 6 below. The Ga180 synbody functions with high affinity and high specificity in solution (Elisa format) and on a solid surface (see Example 8).

Synbodies developed with the techniques disclosed above in the second, third, and/or fourth aspects of the invention function when immobilized to a surface and also function as a solution phase binding agent. The highest binding synbody candidate from one experiment was used as the detection agent in an ELISA experiment and the solution phase dissociation constant ($K_d$) was determined for the synbody, each polypeptide on the synbody and the DNA backbone (see Example 8). This data demonstrates that a large increase in binding affinity can be achieved through the use of the synergistic polypeptides with the proper distance. An additional advantage to this approach is that the synbody is discovered in a single assay and then there is enough of the synbody available to immediately use as the detection agent in a functional assay. This in effect couples discovery and production into a single step, dramatically shortening the synbody development time.

Example 2

Microarray Selection of Affinity Elements for Synbody

Figure 10A:
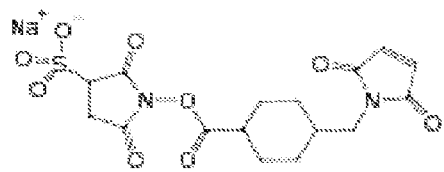
FIG. 10. (a) Structure of maleimide sulfo-SMCC (sulfo-succinimidyl 4-[N-maleimidomethyl]cyclohexane-1-carboxylate) (b) Conjugation of polypeptides to polylysine surface coating by thiol attachment of a C-terminal cysteine of the polypeptide to ϵ amine of a lysine monomer of the poly-lysine surface coating using sulfo-SMCC.
Figure 10B:
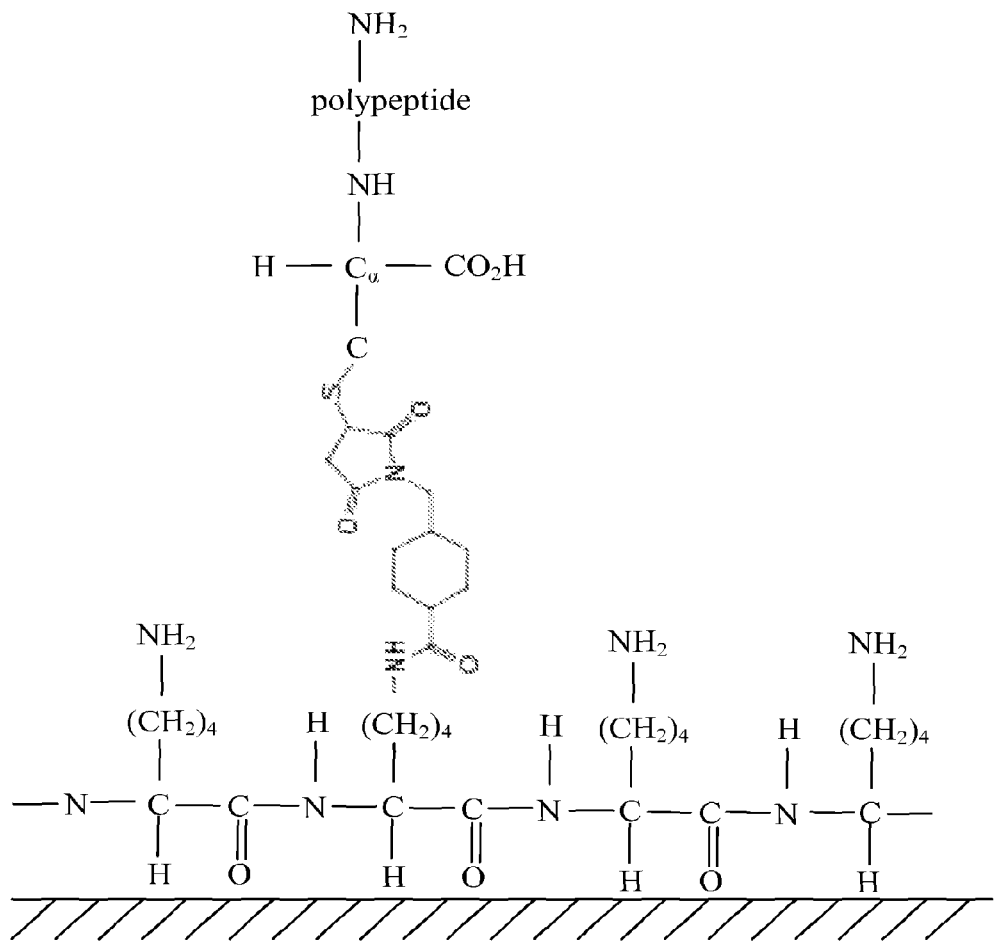

This example demonstrates the identification of affinity elements by screening a target on an array of random polypeptides. A microarray was prepared by robotically spotting about 4,000 distinct polypeptide compositions, two replicate array features per polypeptide composition, on a glass slide having a poly-lysine surface coating. Each polypeptide was 20 residues in length, with glycine-serine-cysteine as the three C-terminal residues and the remaining residues determined by a pseudorandom computational process in which each of the 20 naturally occurring amino acids except cysteine had an equal probability of being chosen at each position. Cysteine was not used except at the C-terminal position, to facilitate correct conjugation to the surface. Polypeptides were conjugated to the polylysine surface coating by thiol attachment of a C-terminal cysteine of the polypeptide to a maleimide (sulfo-SMCC, sulfosuccinimidyl 4-[N-maleimidomethyl]cyclohexane-1-carboxylate, see FIG. 10(a)), which is covalently bonded to the ε amine of a lysine monomer of the poly-lysine surface coating, as shown in FIG. 10(b). The polypeptides were synthesized by Alta Biosciences, Birmingham, UK. Each polypeptide was first dissolved in dimethyl formamide overnight and master stock plates prepared by adding an equal volume of water so that the final polypeptide concentration was about 2 mg/ml. Working spotting plates were prepared by diluting equal volumes of the polypeptides from the master plates with phosphate buffered saline for a final polypeptide concentration of about 1 mg/ml. The polypeptides were spotted in duplicate using a SpotArray 72 microarray printer (Perkin Elmer, Wellesley, Mass.) and the printed slides stored under an argon atmosphere at 4° C. until used. Any other spotting/immobilization chemistry and/or method operable for immobilizing polypeptides on an array surface in a manner compatible with the intended array assay may be employed; by way of non-limiting examples, polypeptides may be conjugated directly to a polylysine surface coating via an amide bond between the C-terminal residue of the polypeptide and the ε amine of a lysine, or may be conjugated to an aminosilane or other functionalized surface exposing free amines. Linkers other than or in addition to SMCC may also be employed; by way of non-limiting example, a PEG linker may be used to position the polypeptide away from the substrate. Surface functionalizations other than amine can be employed, coupled with conjugation chemistry appropriate for attachment of the affinity elements to the surface moieties provided. In some embodiments the surface immobilization may be non-covalent.

Several polypeptides were identified as candidate affinity elements for synbodies against an arbitrarily chosen protein target, transferrin, by incubating transferrin on the polypeptide microarray in the presence of E. coli lysate competitor. Transferrin was randomly direct-labeled at free amines with Alexa™ 555, and E. coli lysate was randomly direct-labeled at free amines with Alexa™ 647. Three replicate arrays were passivized by applying a mixture of BSA and mercaptohexanol for one hour. The arrays were blocked with unlabelled E. coli lysate for one hour, then washed three times with TBST (0.05% Tween) followed by three times with water. A mixture of labeled transferrin and labeled E. coli lysate was applied to the three replicate arrays and incubated for three hours. The arrays were again washed three times with TBST (0.05% Tween) followed by three times with water, and scanned at 555 nm and 647 nm using an array reader. Polypeptides were ranked as candidates for inclusion as affinity elements of synbodies by computing a score for each polypeptide equal to the mean raw 555 nm intensity over the six replicate features, squared, divided by the mean raw 647 nm intensity over the six replicate features. This simple scoring function tends to favor candidate polypeptides that bind at least moderate affinity, since otherwise the 555 nm intensity would be relatively lower, and that are relatively specific, since otherwise the 647 nm intensity would be relatively higher and contribute to a relatively lower score. Many variations of this ranking and identification process can be used, such as, by way of non-limiting examples, two-color comparisons against other competitors; comparisons with data taken in separate experiments with respect to other targets; and use of scoring functions taking into account other factors, employing other functional relationships, and/or involving statistical analysis and/or pre-processing of data and/or correcting for background fluorescence and/or other factors affecting the accuracy of the measured intensities. Ten polypeptides (Table 1) were identified for further evaluation for use as affinity elements in synbodies by choosing the polypeptides having the highest score (one polypeptide was rejected as difficult to synthesize, so the polypeptides chosen were ten of those having the eleven highest scores).

TABLE 1

Transferrin binding affinity elements

| | | |
|---|---|---|
| TRF19 | KEDNPGYSSEQDYNKLDGSC | (SEQ ID NO: 1) |
| TRF20 | GQTQFAMHRFQQWYKIKGSC | (SEQ ID NO: 2) |
| TRF21 | QYHHFMNLKRQGRAQAYGSC | (SEQ ID NO: 3) |
| TRF22 | HAYKGPGDMRRFNHSGMGSC | (SEQ ID NO: 4) |
| TRF23 | FRGWAHIFFGPHVIYRGGSC | (SEQ ID NO: 5) |
| TRF24 | SVKPWRPLITGNRWLNSGSC | (SEQ ID NO: 6) |
| TRF25 | APYAPQQIHYWSTLGFKGSC | (SEQ ID NO: 7) |
| TRF26 | AHKVVPQRQIRHAYNRYGSC | (SEQ ID NO: 8) |
| TRF27 | LDPLFNTSIMVNWHRWMGSC | (SEQ ID NO: 9) |
| TRF28 | RFQLTQHYAQFWGHYTWGSC | (SEQ ID NO: 10) |

Example 3

Microarray Selection of Affinity Elements for DNA Linked Synbody

This example demonstrates another embodiment of a process for identifying affinity elements for incorporation into a synbody. 15-mer polypeptide affinity elements for a DNA linked synbody specific for Gal80 were identified by obtaining and analyzing data from several polypeptide microarray experiments performed using standard 4,000 feature polypeptide microarrays each of whose features comprised a polypeptide 15 residues in length, terminating in glycine-serine-cysteine at the C-terminus, with the other 12 residues selected from 8 of the 20 naturally occurring amino acids according to a pseudorandom algorithm. Four fluorophore-labeled protein targets—gal80, gal80 complexed with gal4 binding polypeptide, transferrin, and α-antitrypsin—were supplied to LC Sciences for array analysis according to LC Sciences' proprietary protocol, and binding (fluorescence intensity) data were obtained. For screening against the random peptide array, Gal80 was labeled with Cy3 and Cy5 fluorescent dyes (GE Healthcare) according to the manufacturer's protocol. The dye-to-protein ratio was determined using the Proteins and Labels settings on a Nanodrop ND-100 spectrophotometer (Nanodrop Technologies). The dye-to-protein ratio for Cy3 and Cy5 labeled Gal80 was 3.4 and 5.0 respectively. The blocking solution used to block the peptide arrays was composed of 1% bovine serum albumin (BSA), 0.5% non-fat milk, 0.05% Tween-20 in 1× phosphate buffered saline (PBS) pH 7.4. After blocking, each array was then washed 3 times with a wash buffer composed of 0.05% Tween-20 in 1×PBS, pH 7.4. The incubation buffer was composed of 1% bovine serum albumin (BSA), 0.5% non-fat milk, in 1× phosphate buffered saline (PBS) pH 7.4. An Axon GenePix 400B Microarray Scanner (Molecular Devices, Sunnyvale, Calif.) was used to acquire images of the peptide arrays. An initial scan of the array was acquired to determine any background fluorescence from each peptide on the array. Fluorescent intensities obtained after protein incubation were subtracted from the background fluorescence and exported into Microsoft Excel for analysis.

Gal4 binding polypeptide is known to bind gal80 at a specific binding site (the gal4 binding site). 142 of the array polypeptides bound gal80 at above-threshold fluorescent intensities, 29 of the array polypeptides bound gal80 complexed to gal4 binding polypeptide at above-threshold fluorescent intensities, and 10 of the array polypeptides bound both gal80 and gal80 complexed to gal4 binding polypeptide at above-threshold fluorescent intensities. Polypeptides that bound gal80 complexed to gal4 binding polypeptide but that did not bind gal80 alone were rejected as likely to be binding to the gal4 binding polypeptide. Intensity data for polypeptides that bound gal80 alone but not gal80 complexed to gal4 binding polypeptide (implying that these polypeptides were binding to the gal4 binding site on gal80) were compared with the intensity data for the same polypeptides with respect to transferrin and α-antitrypsin; polypeptides showing significant binding to either transferrin or α-antitrypsin were excluded, and of the polypeptides remaining, the polypeptide having the highest intensity binding for gal80 was chosen as a first affinity element for incorporation in the gal80 synbody. Intensity data for polypeptides that bound both gal80 alone and gal80 complexed to gal4 binding peptide (implying that these polypeptides were binding gal80 at a site other than the gal4 binding site) were compared with intensity data for the same polypeptides with respect to transferrin and α-antitrypsin; again, polypeptides showing significant binding to either transferrin or α-antitrypsin were excluded, and of the polypeptides remaining, the polypeptide having the highest intensity binding for gal80 was chosen as the second affinity element for incorporation in the gal80 synbody. The sequences of the chosen polypeptides were as shown in Table 2.

TABLE 2

Gal80 binding affinity elements

| BP1 | $NH_2$GTEKGTSGWLKTGSC $CO_2H$ | (SEQ ID NO: 11) |
|---|---|---|
| BP2 | $NH_2$EGEWTEGKLSLRGSC $CO_2H$ | (SEQ ID NO: 12) |

Example 4

Figure 11A:
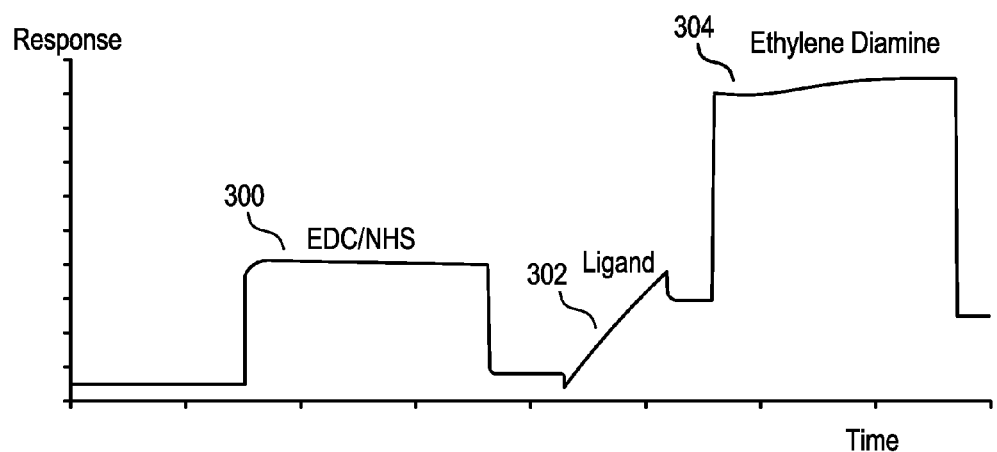
FIG. 11. (a) Signal expected during attachment of protein target to SPR chip surface. (b) Steps in attachment of protein target to SPR chip surface.
Figure 11B:
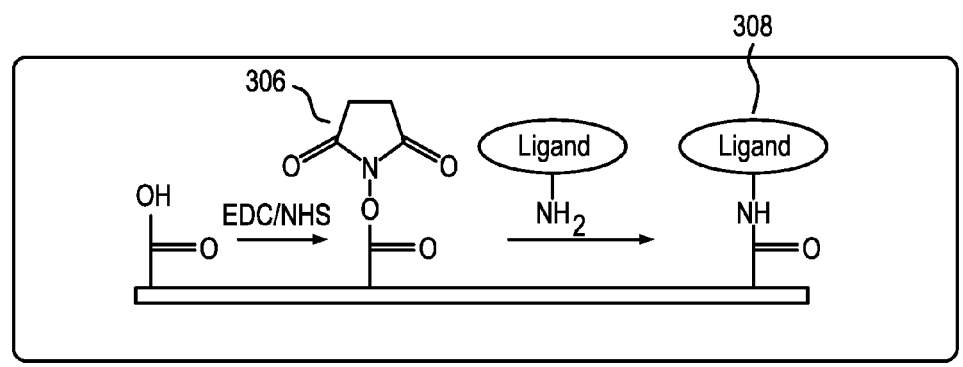

SPR Verification of Binding Characteristics of Transferrin Synbody Affinity Elements This example demonstrates SPR determination of the binding characteristics of affinity elements. Transferrin was immobilized by amine-coupling to the carboxyl-functionalized surface of a Biacore T100 CMS Dextran SPR chip as illustrated in FIG. 11. A 1:1 mixture of EDC (0.4M 1-ethyl-3-(3-dimethylaminopropyl)-carbodiimide in water) and NHS (0.1M N-hydroxysuccinimide in water) was applied 300 at a flow rate of 5 to 10 μl/min for a contact time of about 6 to 10 minutes to activate the surface by conjugating a maleimide 306 to the surface-exposed carboxyl groups. Transferrin 25 μg/ml in immobilization buffer selected for correct pH was then applied 302 at a flow rate of 5 to 10 μl/min for a contact time of about 5 to 10 minutes, allowing the amine functionality on the transferrin 308 to displace the activated NHS ester and bond to the surface via an amide bond. Finally, ethylene diamine (1 M ethylene diamine-HCl at pH 8.5) was applied at a flow rate of 5 to 10 μl/min for a contact time of about 6 to 7 minutes to deactivate any remaining reactive groups on the dextran chip surface. Flow rates and contact times are adjusted as necessary to provide the surface concentration of target desired for the intended application, and may vary by target. In general, for evaluating whether binding occurs, it is preferable to immobilize a relatively large quantity of target, and higher flow rates and/or longer contact times may be used. For determining kinetics, it is preferable to limit the amount of target immobilized so as to minimize rebinding and avidity effects, and lower flow rates and/or contact times may be used.

Candidate affinity elements for the transferrin synbody TRF 19 (SEQ ID NO: 1), TRF21 (SEQ ID NO: 3), TRF23 (SEQ ID NO: 5), TRF24 (SEQ ID NO: 6), TRF25 (SEQ ID NO: 7), and TRF26 (SEQ ID NO: 8) were individually evaluated for solution phase $K_D$ with respect to transferrin by SPR analysis. Because the off rates for these polypeptides were very high, $K_D$ values were estimated by measuring steady-state response for at least five concentrations in a two-fold dilution series, each concentration tested in duplicate. For each experiment, response data were processed using a reference surface to correct for bulk refractive index changes and any nonspecific binding. Data were also double referenced using responses from blank running buffer injections. Each experiment was conducted at 25° C. using PBST (0.01M Phosphate Buffered Saline, 0.138M NaCl, 0.0027M KCl, 0.05% surfactant Tween20, pH 7.4) as the running buffer on a Biacore T100 instrument. Analytes were injected for 60 s at a flow rate of 30 μl/min. The antigen surfaces were regenerated with 30 s consecutive pulses of NaOH/NaCl (50 mM NaOH in IM NaCl) and Glycine (10 mM glycine—HCl, pH 2.5). Estimate $K_D$ values are shown in Table 3.

TABLE 3

K$_D$ values for transferring synbody candidate affinity elements

| | Solution Phase K$_D$ |
|---|---|
| TRF19 (SEQ ID NO: 1) | ~ 150 uM |
| TRF21 (SEQ ID NO: 3) | ~ 60 uM |
| TRF23 (SEQ ID NO: 5) | ~ 50 uM |
| TRF24 (SEQ ID NO: 6) | ~ 50 uM |
| TRF25 (SEQ ID NO: 7) | ~ 60 uM |
| TRF26 (SEQ ID NO: 8) | ~ 100 uM |

Example 5

SPR Analysis of Affinity Element Binding to Distinct/Multiple Sites on Target

This example demonstrates an SPR-based method for identifying polypeptide affinity elements that bind distinct sites on a protein target. The transferrin target was immobilized on a Biacore T100 SPR chip, and candidate polypeptides were applied in 1:1 mixtures in pairs and response data obtained, in accordance with the methods described in Example 4 above. As illustrated in FIG. 12, upon flowing candidate polypeptides over the immobilized target, ideally one polypeptide applied alone would bind to a first binding site on the target and produce a first characteristic SPR response level (FIG. 12(a)), the other polypeptide would bind to a second, distinct binding site on the target, producing a second characteristic response level (FIG. 12(b)), and a mixture of the two polypeptides together (at the same concentrations as before) would produce a response level approximating the sum of the response levels produced by each polypeptide alone, as the polypeptides bind to distinct binding sites (FIG. 12(c)). However, it is also possible that the two polypeptides do not bind distinct sites on the target, but instead compete for the same binding site (FIG. 12(d)), in which case the expected SPR response would be intermediate between the response level produced by either polypeptide separately and the sum of the two. FIG. 13 shows the results of evaluation of a number of pairs of the polypeptides that were identified as described in Example 2 (see Table 1). Among other pairs, TRF23 (SEQ ID NO: 5) and TRF26 (SEQ ID NO: 8) had solution phase affinities for transferrin in a range of K$_D$ of about 50 to 100 μM (see Table 3) and were found to bind distinct sites on transferrin.

Analysis to determine ability to bind distinct binding sites can be performed by any other method operable to assess whether two affinity elements do or do not mutually interfere in binding to the target. By way of non-limiting example, this may be done by comparing, by array experiment, SPR, or any other suitable method, a polypeptide's binding characteristics with respect to a target with the target pre-bound to a target-specific antibody; it may be inferred that polypeptides that bind the target with and without the antibody present are likely binding to a site other than the site that the antibody binds, and that polypeptides that bind the target without the antibody present and do not bind with the antibody present are likely binding to the site that the antibody binds.

Example 6

Synthesis of DNA-Linker Synbody

Figure 14:
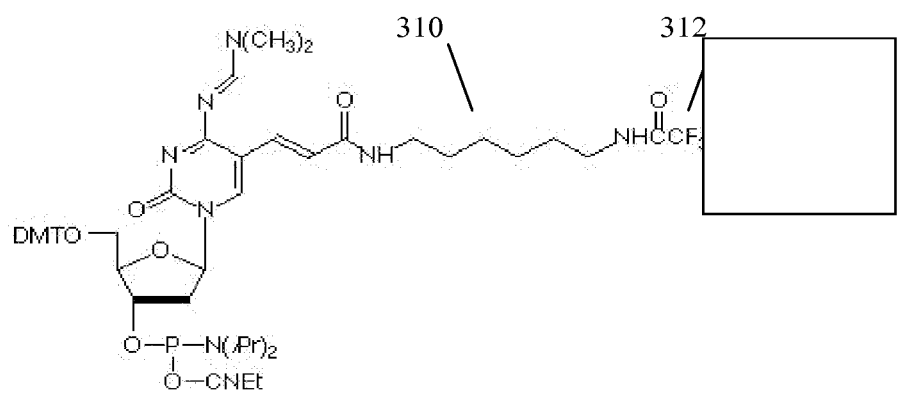
FIG. 14. 5'-Dimethoxytrityl-N-dimethylformamidine-5-[N-(trifluoroacetylaminohexyl)-3-acrylimido]-2'-deoxyCytidine, 3'-[(2-cyanoethyl)-(N,N-diisopropyl)]-phosphoramidite, used to provide amine-modified cytosines in oligonucleotides.
Figure 15:
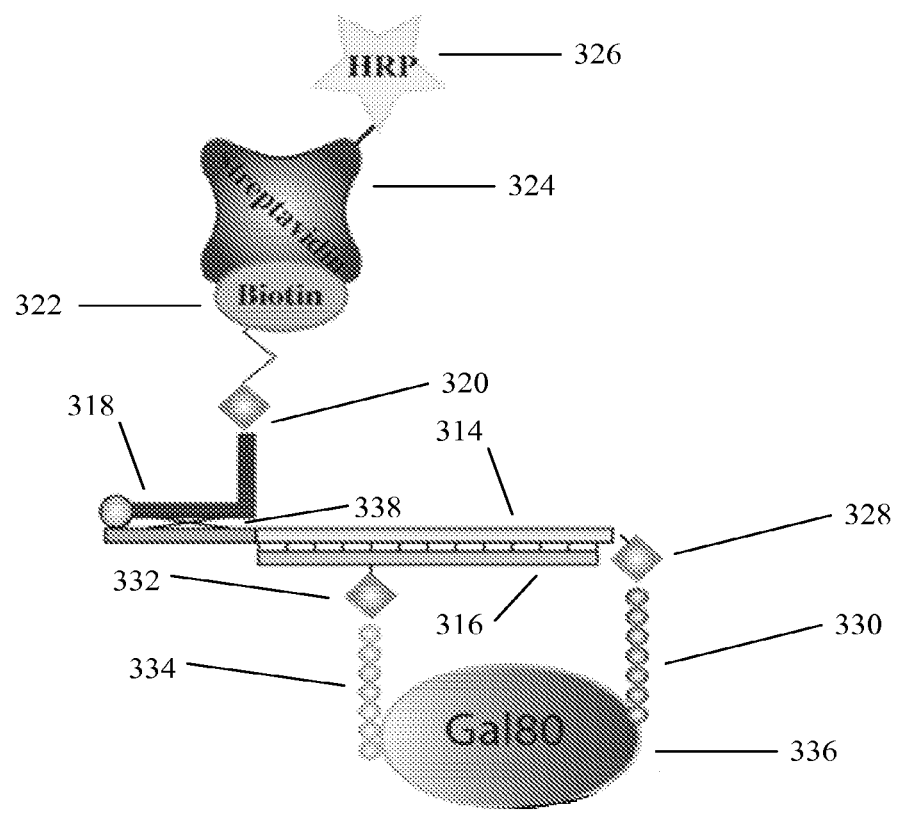
FIG. 15. Schematic representation of a synbody specific for gal80, comprising two polypeptide affinity elements identified as described in Example 3 joined by a DNA linker.

This example demonstrates the synthesis of a synbody specific for gal80, comprising two 15-mer polypeptide affinity elements identified as described in Example 3 joined by a DNA linker. The structure is illustrated schematically in FIG. 15. The DNA linker sequence was determined randomly, subject to the constraints that the sequence should not result in predicted formation of secondary structures, should not be similar or identical to any naturally occurring sequence as determined by BLAST search, and the variable strand should have cytosine residues at the locations at which attachment of the affinity elements is desired (although other attachment modalities could be used, for convenience the attachment employed involved C6 amine modification of the cytosine base). The template strand 314 was amine-modified at the 5' terminal cytosine residue to allow attachment of the polypeptide affinity element 330 via a maleimide linker 328. The variable strand 316 was reverse complementary to the template strand and was amine-modified at an internal cytosine residue to allow attachment of the other polypeptide affinity element 334, again via a maleimide linker 332. A library of variable strands were obtained, each amine-modified at a different position, to provide a range of attachment points corresponding to a range of separation distances between the affinity elements. Determination of attachment points also took into account the angular orientation of residues along the DNA helix, so as to avoid positioning the affinity elements on opposite sides of the DNA backbone. For B-DNA in solution under physiological conditions, the double helix makes a complete rotation in about 10.4 to 10.5 base pairs and has a length of about 3.4 nm per 10 base pairs. To align the attachment points of the affinity elements at approximately the same angular position around the longitudinal axis of the helix, and keeping in mind that the affinity elements are attached to opposite strands, the bases comprising the attachment points may be chosen at a separation of approximately an even multiple of about 10.5 (one full rotation) plus about 4 (to account for the difference in angular position between the strands), plus or minus about 2 or 3 (since affinity elements do not necessarily bind optimally to the target by being perfectly aligned with each other). By screening various attachment points, various separation distances and relative orientations of the affinity elements can be tested. For the example here described, variable strands having amine-modified cytosines at positions 13, 15, 17, 24, 26, and 28 (counting from the 3' end of the variable strand) were obtained. The amine-modified cytosines (hereafter dC C6) were incorporated in the oligonucleotides using 5'-Dimethoxytrityl-N-dimethylformamidine-5-[N-(trifluoroacetylaminohexyl)-3-acrylimido]-2'-deoxyCytidine, 3'-[(2-cyanoethyl)-(N,N-diisopropyl)]-phosphoramidite, see FIG. 14, and have a trifluoroacetylaminohexyl moiety 310 extending from the 5 carbon of the cytidine base.

The polypeptides were conjugated to synthetic DNA template 314 and variable 316 strands in accordance with methods described in detail in Williams BAR, Lund K, Liu Y, Yan H, Chaput J C: Self-Assembled Peptide Nanoarrays: An Approach to Studying Protein-Protein Interactions. Angew Chem Int Ed 2007, 46:3051-3054. The two DNA oligonucleotides, template strand 314 (5' (dC C6)CC GAA ACA ACC GCG AGA GGC ACG CGC GTA GCC GTC ACC GGC TAT-3' (SEQ ID NO: 13), wherein the 5' terminal dC C6 is amine-modified cytosine as described above) and variable strand 316 (5' GCT ACG CGC GTG CCT CTC G(dC C6)G GTT GTT TCG GG-3' (SEQ ID NO: 14), wherein the dC C6 appearing at the position 13 counting from the 3' terminus is amine-modified cytosine) were purchased from Keck Oligonucleotide Synthesis Facility (Yale University). These were conjugated (at the trifluoroacetyl moiety (312, FIG. 14) of the amine-modified cytosine to the bifunctional linker 4-(maleimidomethyl)-1-cyclohexane carboxylic acid Λ/-hydroxysuccinimide ester (SMCC, Sigma Aldrich) 328, 332 by combining 200 μL of SMCC (1 mg/mL) in acetonitrile with 200 μL of DNA (20 nmol) in 0.1 M $KHPO_4$ buffer (pH 7.2). Following a 3 h incubation at room temperature, a second portion (20 μL) of SMCC (10 mg/ml) was added and the reaction was allowed to continue overnight at room temperature. Excess SMCC was removed from the SMCC conjugated DNA samples by size exclusion chromatography on a Nap-5 column (Amersham Bioscience). To construct the polypeptide-oligonucleotide conjugates, the Gal 80 binding polypeptide 330 ($NH_2$-GTEKGTSGWLKTGSC-$CO_2$H, (SEQ ID NO: 11)20 nmol) was incubated with the SMCC-conjugated template strand 314 (2 nmol) in 200 μL of 0.1 M $KHPO_4$ buffer (pH 7.2) and the Gal 4 activation domain peptide 334 ($NH_2$-EGEWTEG-KLSLRGSC-$CO_2$H, (SEQ ID NO: 12)20 nmol) was incubated with the SMCC-conjugated variable strand 316(2 nmol) in 200 μL of 0.1 M $KHPO_4$ buffer (pH 7.2) for 3 h at room temperature, resulting in conjugation of the C-terminal cysteine of the polypeptides to the respective SMCC linkers 328, 332. Polypeptide-oligonucleotide conjugates were HPLC purified. The two polypeptide-oligonucleotide conjugates readily undergo hybridization by Watson-Crick base pairing.

The Gal 80-template strand conjugate 314 was cross-linked 338 to a thiol containing DNA oligonucleotide 318 (5' (psoralen)TA GCC GGT GTG AAG TTT CTG CTA GTA ATG (thiol modifier C3) 3') (SEQ ID NO: 15) which is partially reverse complementary to part of the 3'-terminal region of the template strand 314 and able to partially hybridize to the template strand (and was then crosslinked 338 to the template strand 314 for stability), with the 3' end of the thiol containing oligo 318 extending single-stranded from the synbody construct and providing, via the thiol modifier 320, a conjugation site for maleimide-modified biotin 322, which in turn provides a site to which streptavidin 324 conjugated HRP 326 can be attached, enabling use of the construct in an ELISA-type assay. Inclusion of the third DNA strand 318 is optional. If the third DNA strand 318 is used, any attachment chemistry operable to attach any desired entity to the unhybridized portion of the strand may be used; by way of non-limiting example, any maleimide may be conjugated to the thiol modifier, and if maleimide-modified biotin is used, any streptavidin-linked entity may be applied to the biotin. Hybridization occurred with 40 μL of Gal 80-template conjugate (2 nmol) and 4.8 μL of the psoralen containing strand (4 nmol) in 20 μL crosslinking buffer (100 mM KCL, 1 mM spermidine, 200 mM Hepes pH 7.8, and 1 mM EDTA pH 8) at 90° C. for 5 min. then cooled on ice for 30 min. The sample was placed in one well of a 96 well flat bottom, clear NUNC plate and radiated with ultra violet light (366 nm) for 15 min. Unreacted crosslinking DNA was purified on streptavidin magnetic beads which contained the biotinylated complementary DNA strand. The flow-through was collected as the crosslinked Gal 80-template conjugate and hybridized with equal molar ratio of the Gal 4-variable strand by incubating in the presence of 1 M NaCl at 90° C. for 5 min. and then chilled on ice for 30 min. The disulfide bond on the crosslinked DNA was reduced 30 min. before use by incubating with 10 mM TCEP (tris(2-carboxyethyl) phosphine hydrochloride) at room temperature for 30 min. The mercaptopropane was removed by using a microcon YM-10 molecular weight spin column (Millipore).

Example 7

Synthesis of Synbody

Figure 16:
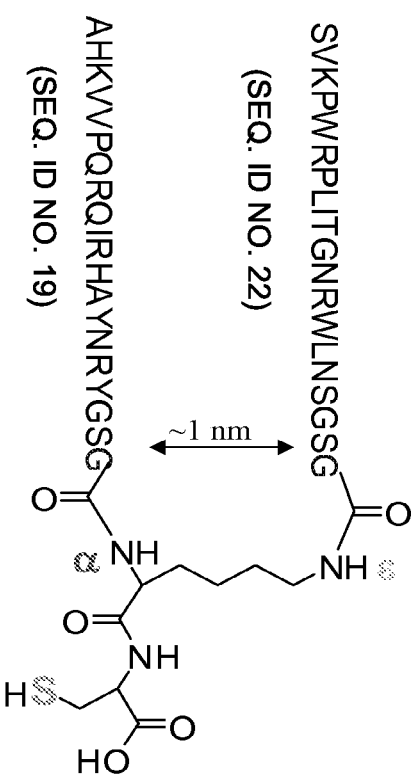
FIG. 16. (SEQ ID NOS: 19 and 22) A synbody comprising polypeptide affinity elements.
Figure 17:
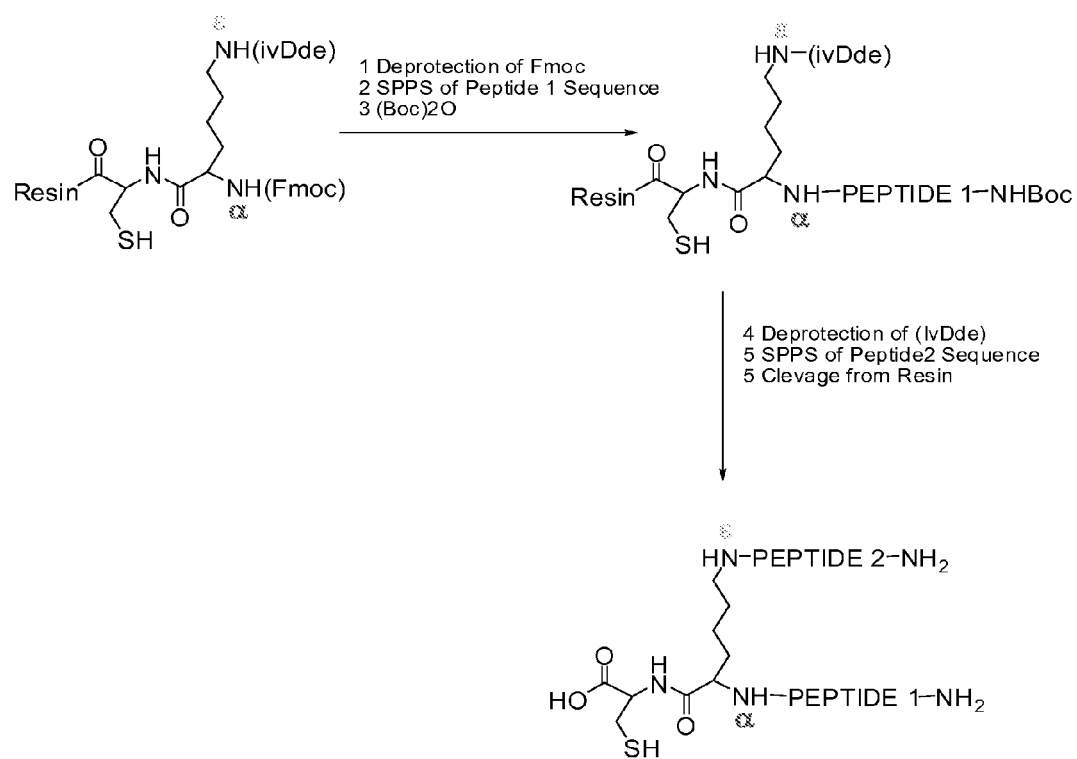
FIG. 17. Flow chart of the synthesis of a synbody comprising polypeptide affinity elements.

This example demonstrates the synthesis of the synbody shown in FIG. 16 using polypeptide affinity elements previously identified (sequences as shown in FIG. 16). As shown in FIG. 17, lysine, protected by an Fmoc protecting group at the α amine and by an ivDde protecting group at the ε amine, was conjugated to a cysteine residue which was in turn attached to the resin support via an acid labile linkage. The Fmoc protecting group was removed, the first polypeptide affinity element was synthesized by sequential addition of residues by standard solid phase peptide synthesis techniques from the α amine of the lysine, and the terminal Fmoc protecting group was converted to Boc. The ivDde protecting group was then removed from the ε amine of the lysine, and the second polypeptide affinity element was synthesized by sequential addition of residues to the exposed ε amine of the lysine. The acid labile linkage of the cysteine residue to the resin was cleaved, freeing the completed synbody. The foregoing steps were performed in accordance with standard solid phase peptide synthesis techniques. See, e.g., Atherton E, Sheppard R C: Solid Phase peptide synthesis: a practical approach. Oxford, England: IRL Press; 1989, and Stewart J M, Young J D: Solid Phase Peptide Synthesis, 2d Ed. Rockford: Pierce Chemical Company; 1984, which are incorporated herein by reference. Any other technique operable for synthesizing and/or assembling the structure may be employed; by way of non-limiting example, either or both polypeptide affinity elements may be synthesized in place by sequential addition of residues using standard solid phase synthesis techniques, or by assembly of presynthesized substructures. The lysine linker provides a spacing of about 1 nm between the attachment points of the two polypeptides as shown in FIG. 16. The cysteine may be biotinylated to enable detection using fluorescently labeled streptavidin, or used for any other desired functionalization. Other C-terminal residues or structures may also be used; synbodies were also prepared having C-terminal glycine or alanine in lieu of cysteine.

The synbodies were purified on a C-18 semi-preparative column using 0.1% TFA in water and 90% $CH_3CN$ in 0.1% TFA with gradient of 10 to 95% in 25 minutes, at flow rate of 4 ml/min and verified by MALDI-TOF.

Example 8

SPR Analysis of DNA-Linked Synbody and Linker Distance/Orientation Optimization

Figure 18:
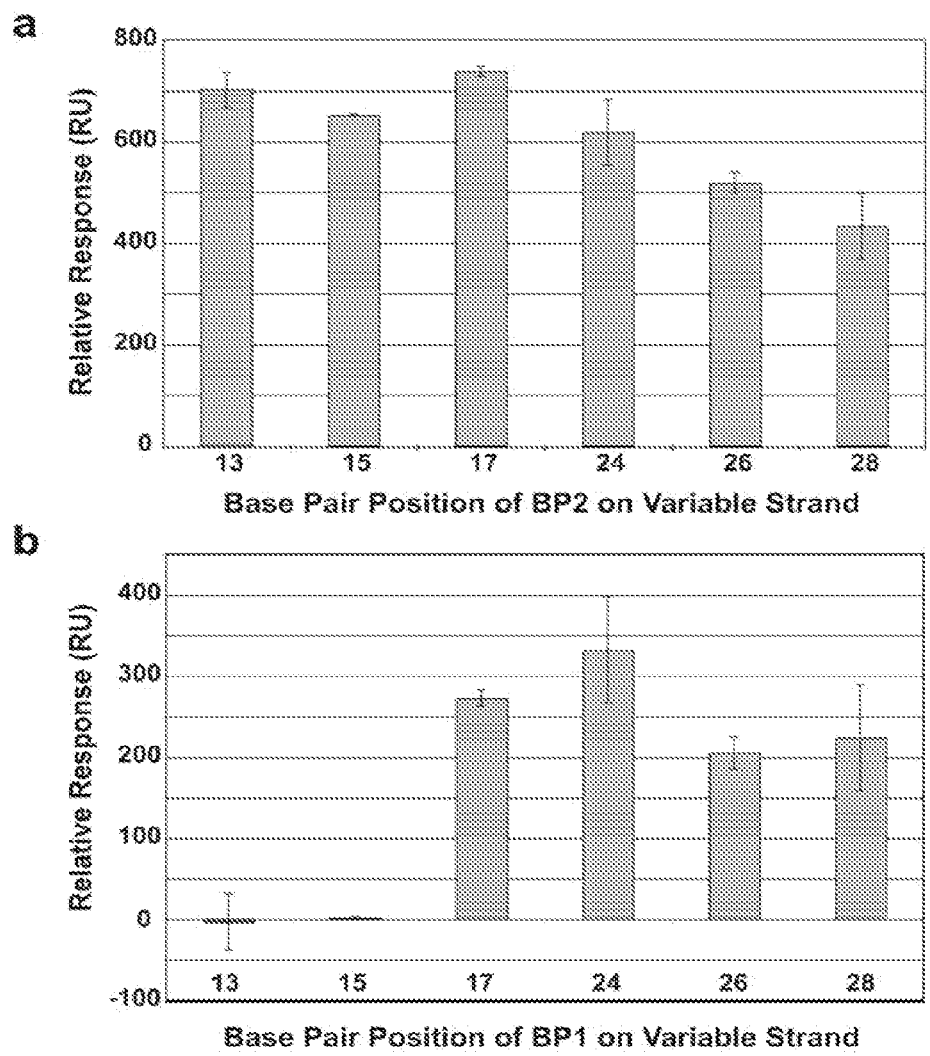
FIG. 18. Relative SPR responses of BP1 (SEQ ID NO: 11) and BP2 (SEQ ID NO: 12)-containing synbodies with respect to gal80.

This example demonstrates the optimization of linker length for a DNA synbody, and demonstrates that the joinder of two affinity elements having moderate affinity for a target by an appropriate linker produces a synbody having affinity for the same target that is substantially improved over that of the individual affinity elements. DNA-linked synbody constructs (prepared as described in Example 6) were immobilized on a Flexchip, and gal80 in solution was flowed over the chip and response data obtained. 12 distinct synbody constructs were evaluated, each having the BP1 (SEQ ID NO: 11) polypeptide as one affinity element and the BP2 (SEQ ID NO: 12) polypeptide as the other affinity element. Six of the constructs had the (SEQ ID NO: 11) polypeptide attached to the template strand and the BP2 (SEQ ID NO: 12) polypeptide attached to the variable strand at each of six different positions (positions 13, 15, 17, 24, 26, and 28, counting from the 3' end of the variable strand); the other six constructs were identical to the first six except that positions of the two polypeptides were reversed (i.e. the BP2 (SEQ ID NO: 12) polypeptide was attached to the template strand and the BP1 (SEQ ID NO: 11) polypeptide was attached to the variable strand). Relative SPR responses of these synbodies with respect to gal80 were determined and compared, with the results shown in FIG. 18. The configuration with BP1 (SEQ ID NO: 11) on the template strand and BP2 (SEQ ID NO: 12) on the variable strand produced a higher response than the reverse configuration, and affinity of the synbody for gal80 declined as the linker was elongated, indicating that a linker length corresponding to about 13 to 17 DNA bases, or about 5 nm, was optimal for this configuration. This corresponds well to the known dimensions of the gal80 homodimeric structure, which is approximately cylindrical, about 10 nm in length and about 5 nm in diameter.

Figure 19:
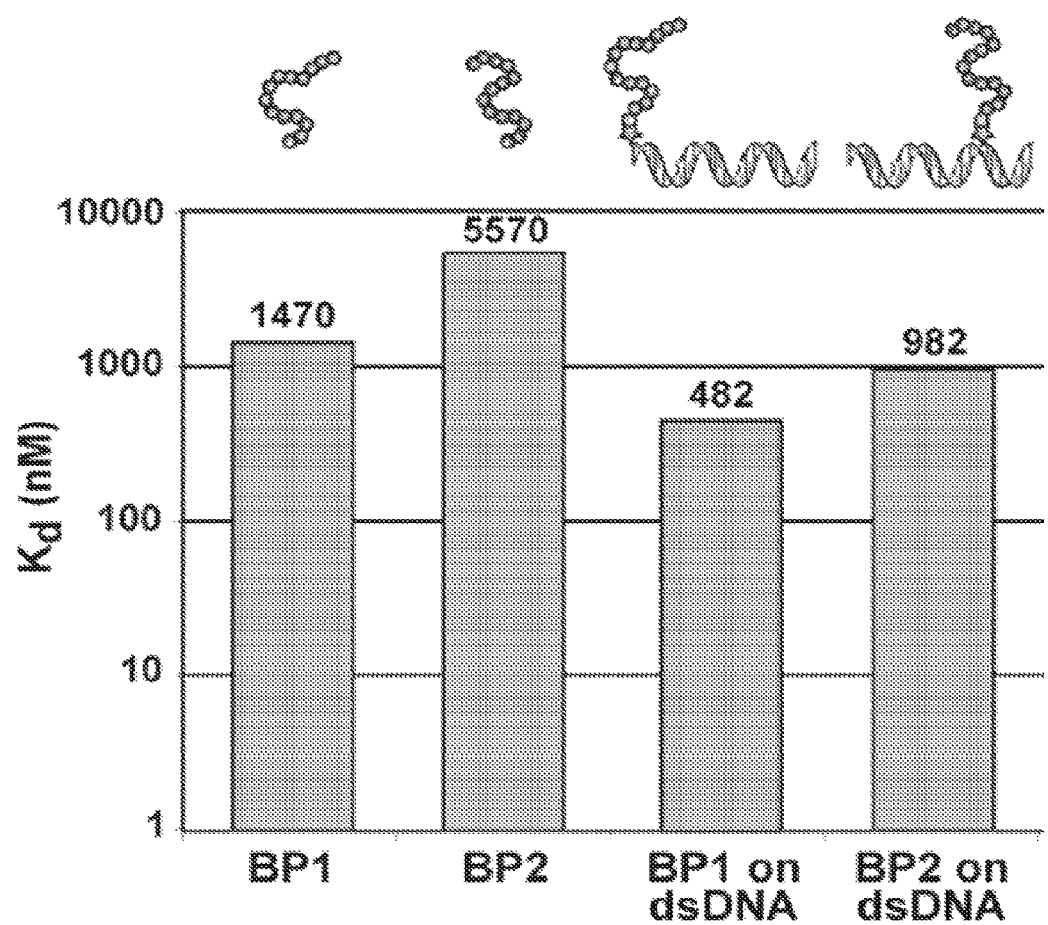
FIG. 19. Affinities (Kd) with respect to gal80 of affinity elements BP1 (SEQ ID NO: 11) and BP2 (SEQ ID NO: 12) alone, BP1-BP2 containing synbody, and BP1 and BP2 alone conjugated to DNA linker.
Figure 20:
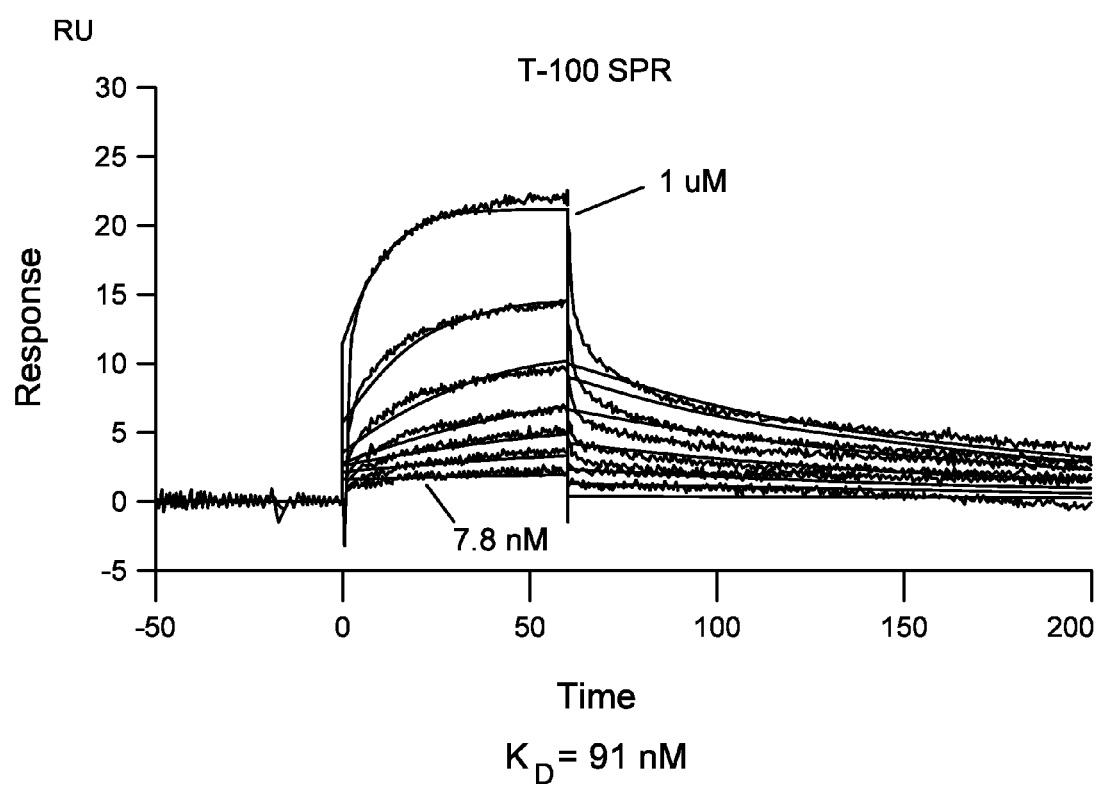
FIG. 20. Data derived from ELISA-type analyses confirming the binding affinities of BP1 and BP2 alone for gal80 compared to the BP1-BP2 containing synbody.

From on and off rates determined by SPR using the methods described in Example 4 with gal80 immobilized on the SPR chip, dissociation constants were obtained and compared for the linker-optimized synbody having the BP1 (SEQ ID NO: 11) affinity element on the template strand and the BP2 (SEQ ID NO: 12) affinity element at position 13 from the 3' end of the variable strand, for each affinity element alone, and for each affinity element complexed by itself to the double-stranded DNA linker. As shown in FIG. 19, the affinity elements alone had affinities in a IQ range on the order of a few μM ($K_d$=1.5 for BP1 (SEQ ID NO: 11) and $K_d$=5.6 for BP2 (SEQ ID NO: 12)). FIG. 20 shows the results of the SPR analysis of the binding of the BP1 (SEQ ID NO: 11)/BP2 (SEQ ID NO: 12) DNA-linked synbody in solution, in a concentration series ranging from 1 μM to 7.81 nm, to surface-bound Ga180, indicating a $K_d$ value of 91 nM. A gel shift assay was performed, again resulting in an estimated $K_d$ value of about 100 nM.

These data were confirmed by ELISA-type analysis, where gal80 was immobilized in an ELISA well using standard methods, and the linker-optimized synbody, functionalized with streptavidin-conjugated HRP as described in Example 6, was applied in a concentration series and bound synbody detected in accordance with standard ELISA techniques. As shown in FIG. 20, the synbody was again found to have low nanomolar affinity for gal80, as compared to affinities in the $K_d$ range of about 25 to 50 μM for each of the affinity elements individually with respect to gal80.

The specificity of the linker-optimized synbody was assessed by SPR determination of the affinity of the synbody for three protein targets other than gal80 (α1-antitrypsin, albumin, and transferrin). In each case the affinities were in a $K_d$ range more than 1000 times greater than the $K_d$ of the synbody for gal80.

Example 9

SPR Analysis of Synbody

This example demonstrates that synbodies comprising affinity elements identified as described in Example 2 are capable of binding the target used for their identification (here, transferrin) with affinity that is significantly better than the affinity for the same target of either affinity element alone. Various synbodies comprising various pairings of affinity elements TRF-19 (SEQ ID NO: 1) through TRF-26 (SEQ ID NO: 8) (see Table 3) were synthesized in accordance with the methods described in Example 7 above, and their affinities for transferrin were evaluated by SPR with transferrin immobilized on the SPR chip in accordance with the methods described in Example 4 above, and with $K_d$ values determined from kinetics. All of the pairings evaluated resulted in synbodies having $K_d$ values less than the $K_d$ values of their individual affinity elements alone (i.e., all were lower than about 50 μM). The synbody comprising TRF-26 (SEQ ID NO: 8) and TRF-23 (SEQ ID NO: 5) had $K_d$ with respect to transferrin of 150±50 nm.

Example 10

Figure 21:
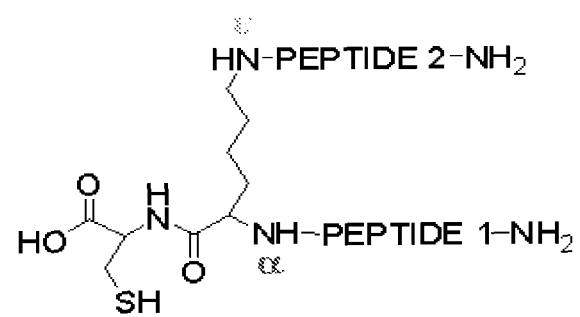
FIG. 21. Schematic of synbodies constructed by linking the C-terminal glycines of two 20-mer polypeptides to the a and c amine moieties of a lysine molecule, thereby providing a spacing of about 1 nm.

Synbodies were constructed by synthesizing two 20-mer polypeptides on the α and ε amine moieties, respectively, of a lysine molecule as described in Example 7 above, thereby providing a spacing of about 1 nm as shown in FIG. 21. The thiol group of the cysteine is biotinylated to enable detection using fluorescently labeled streptavidin.

The polypeptide sequences used as binding elements in the synbodies were determined as described in Example 2. Several polypeptides corresponding to the loci at which transferrin bound were selected, synthesized (replacing the terminal cysteine with glycine to facilitate conjugation to the lysine linker for assembly of the synbody), and analyzed by SPR as described in Example 4 to identify pairs of polypeptides capable of simultaneously and non-competitively binding distinct loci on transferrin. Several such pairs were selected for incorporation into synbodies.

Two biotinylated anti-TRF synbodies (SYN23-26 and SYN 21-22) were applied to a protein microarray having 8,000 features (Invitrogen Protoarray Human Protein Microarray v. 4.0 for immune response biomarker profiling), each feature comprising a distinct human protein (GST fusion) adsorbed to a nitrocellulose coated slide. Application of the synbodies to the microarray was performed in accordance with manufacturer instructions: (see ProtoArray Human Protein Microarray, Invitrogen, Catalog no. PAH052401, Version B, 15 Dec. 2006, 25-0970, Users Manual.) After blocking the array with 1% BSA/PBS/0.1% Tween for 1 hour at 4 C with gentle shaking, 120 μl of probing buffer (1×PBS, 5 mM mgCl2, 0.5 mM DTT, 0.05% Triton X-100, 5% glycerol, 1% BSA) with synbody was applied to the array. The prescribed cover slip was placed over the array and adjusted to remove air bubbles. The array was incubated in a 50 ml conical tube, printed side up, for 1.5 hours at 4 C without shaking The array was then removed from the conical tube inserted diagonally into the array chamber, kept on ice. 8 ml probing buffer was added to the chamber wall. The cover slip was removed and the array was incubated in probing buffer for 1 minute on ice. The probing buffer was decanted and drained. Two further washings were performed adding 8 ml probing buffer, incubating on ice for 1 minute, and decanting and draining 5 nM fluorescently labeled streptavidin diluted in 6 ml probing buffer was incubated on the array for 30 minutes on ice in the dark, after which the solution was decanted and drained. Three wash steps were performed, each by adding 8 ml probing buffer, incubating for 1 minute on ice, decanting, and draining The array was removed from the chamber, centrifuged at 800×g for 5 minutes at room temperature. The array was dried in the dark for 60 minutes at room temperature, after which it was scanned using a fluorescent microarray scanner and data was taken and analyzed.

The binding pattern data for SYN23-26 were compared with data obtained for a high quality anti-TRF monoclonal antibody, ICIO ($K_d$=1.5 μm), on the same array. The sequences of the polypeptide binding elements of SYN21-22 were QYHHFMNLKRQGRAQAYGSG (SEQ ID NO: 16) and HAYKGPGDMRRFNHSGMGSG (SEQ ID NO: 17) and the sequences of SYN23-26 were FRGWAHIFFG-PHVIYRGGSG (SEQ ID NO: 18) and AHKVVPQRQ-IRHAYNRYGSG (SEQ ID NO: 19).

Figure 22:
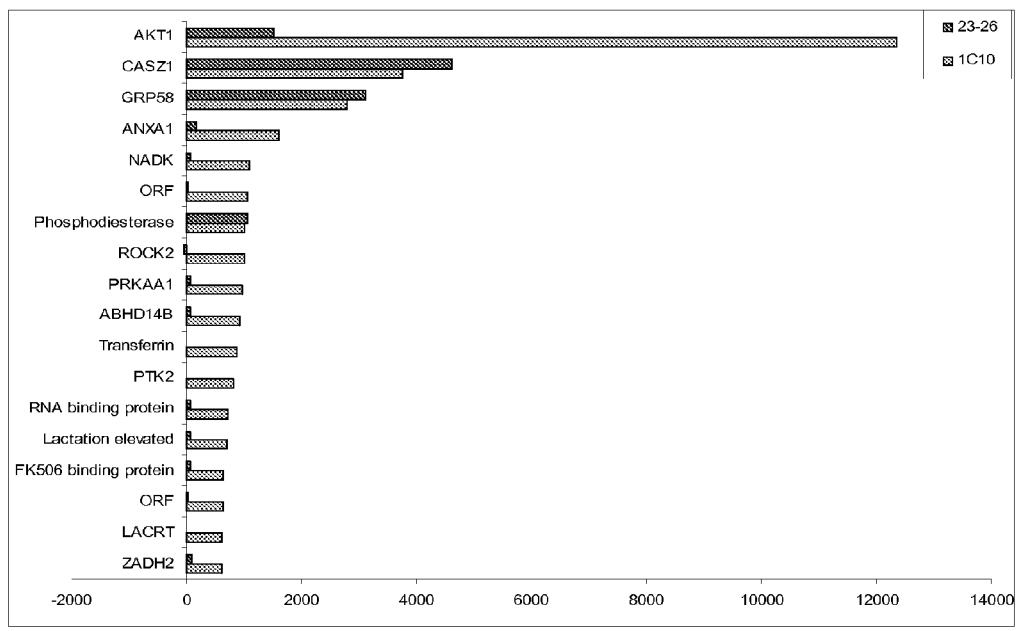
FIG. 22. Graph showing the 18 proteins to which 1C10 bound with highest intensity, and relative intensities observed.
Figure 23:
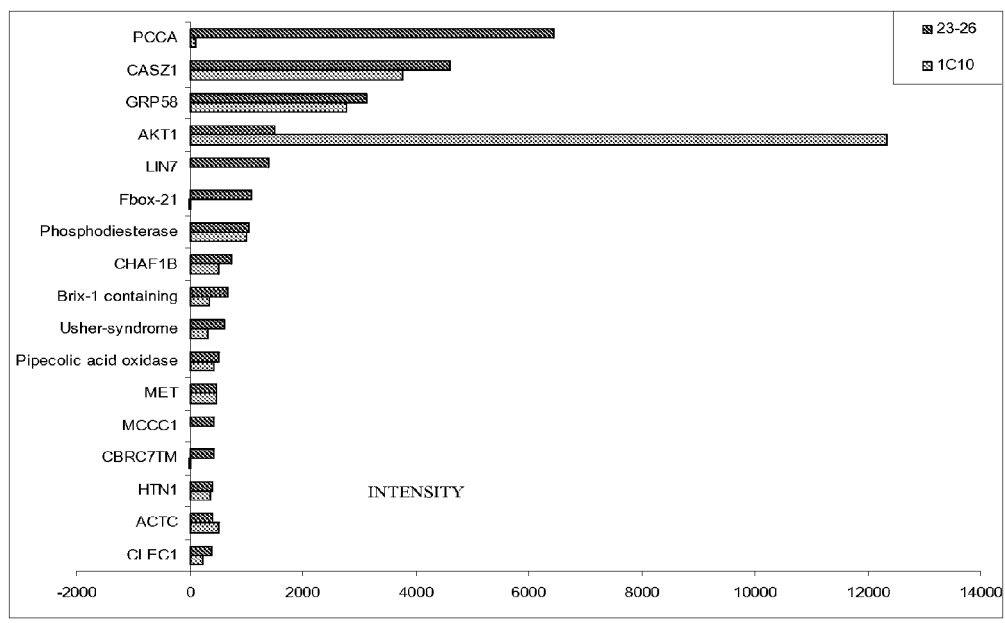
FIG. 23. Graph showing the 18 proteins to which SYN23-26 bound with highest intensity, and relative intensities observed.
Figure 24:
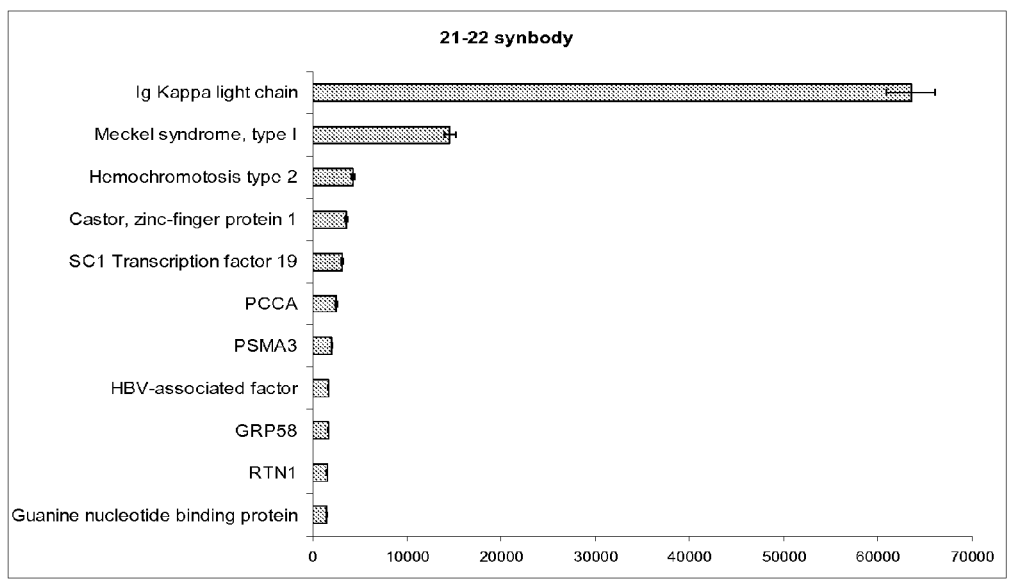
FIG. 24. Graph showing the 18 proteins to which SYN21-22 bound with highest intensity, and relative intensities observed.

Comparisons of the measured fluorescence intensity values exceeding background (which are a measure of occupancy and, by extension, binding affinity) for SYN23-26 with those for the 1C10 antibody are shown in FIG. 22 for the 18 proteins to which 1C10 bound with highest intensity and in FIG. 23 for the 18 proteins to which SYN23-26 bound with highest intensity. Data for SYN21-22 are shown in FIG. 24. Binding of SYN23-26 to transferrin and AKT1 was evaluated by SPR, indicating estimated Kd values of about 1 nM with respect to AKT1 and about 141 nM with respect to transferrin.

As can be seen from the intensity plot for the highest affinity targets for the 1C10 anti-TRF antibody (FIG. 22, light bars), 1C10 bound ten other targets with intensity equal to or greater than that for TRF, and bound one target, AKT1, with more than ten-fold higher intensity. Similar results were obtained for SYN21-22 (FIG. 24).

The monoclonal antibody 1C10 and both synbody constructs exhibited high specificity, as indicated by high affinities for only a few targets, with the plot of affinities for all targets, ranked in descending order by affinity, appearing to decline rapidly and approximately exponentially. The highest affinities observed for the antibody and for both synbodies corresponded to targets other than transferrin. This data illustrates that bivalent synbodies (SYN23-26 and SYN21-22), each having binding elements chosen on the basis of their affinity for distinct sites on an arbitrarily chosen protein target (transferrin), each have, with respect to one target from a library of 8,000 (PCCA for SYN23-26 and Ig kappa light chain for SYN21-22), affinity and specificity characteristics essentially equivalent to those exhibited by the monoclonal antibody 1C10 for its highest affinity target (AKT1).

It is noteworthy that SYN23-26 bound to seven targets (FIG. 4, PCCA, CASZ1, GRP58, AKT1, LINT, Fbox-21, and Phosphodiesterase) with intensities higher than that exhibited by 1C10 for its nominal target (TRF), suggesting that SYN23-26 could be used as a synthetic antibody against any of these seven protein targets with quality equivalent to that of a high quality commercial monoclonal antibody.

Example 11

A bivalent synbody having binding elements selected for affinity for Ga180 was assembled and linked via a nucleic acid linker, providing spacing between binding elements of approximately 5 nm, as described in Example 6 above. Binding elements BP1 (SEQ ID NO: 11) and BP2 (SEQ ID NO: 12) were identified as described in Example 3 above.

Figure 25:
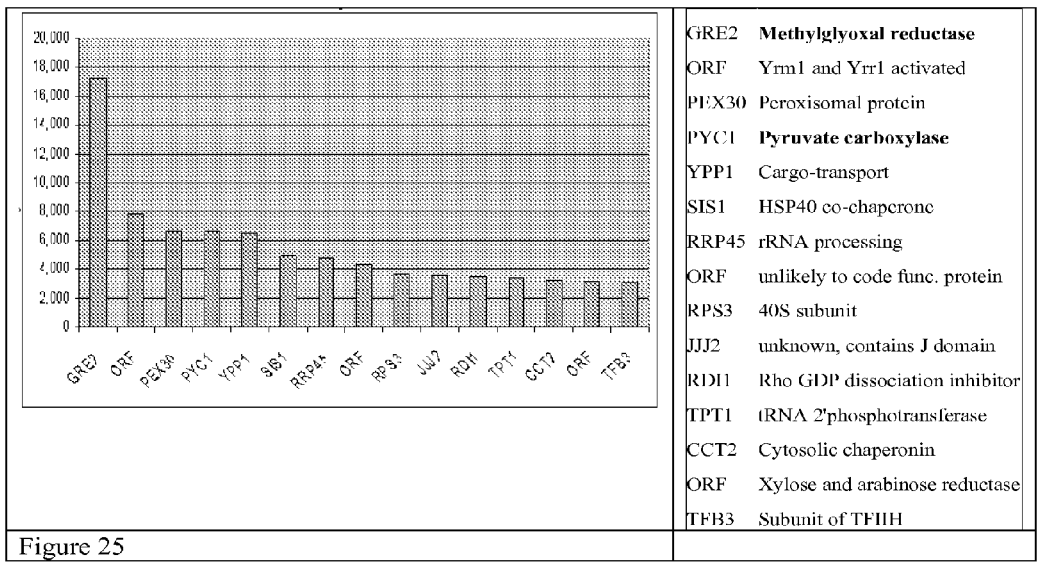
FIG. 25. Graph showing the 15 proteins to which the gal80 synbody bound with highest intensity, and relative intensities observed.

The (biotinylated) synbody was screened on an array of 4,000 yeast proteins (Invitrogen Protoarray Yeast Protein Microarray for immune response biomarker profiling), and detected using Alexa™ 555-labeled streptavidin. Fluorescence intensity data was obtained as shown in FIG. 25 (adjusted for background fluorescence). The distribution of affinities over the highest-binding protein targets was again comparable to that characteristic of a high quality monoclonal antibody, and, again, the protein targets for which the synbody exhibited the highest affinity did not include the target (Ga180) for which the binding elements were originally screened.

Example 12

DNA Tile Synbody

Figure 26:
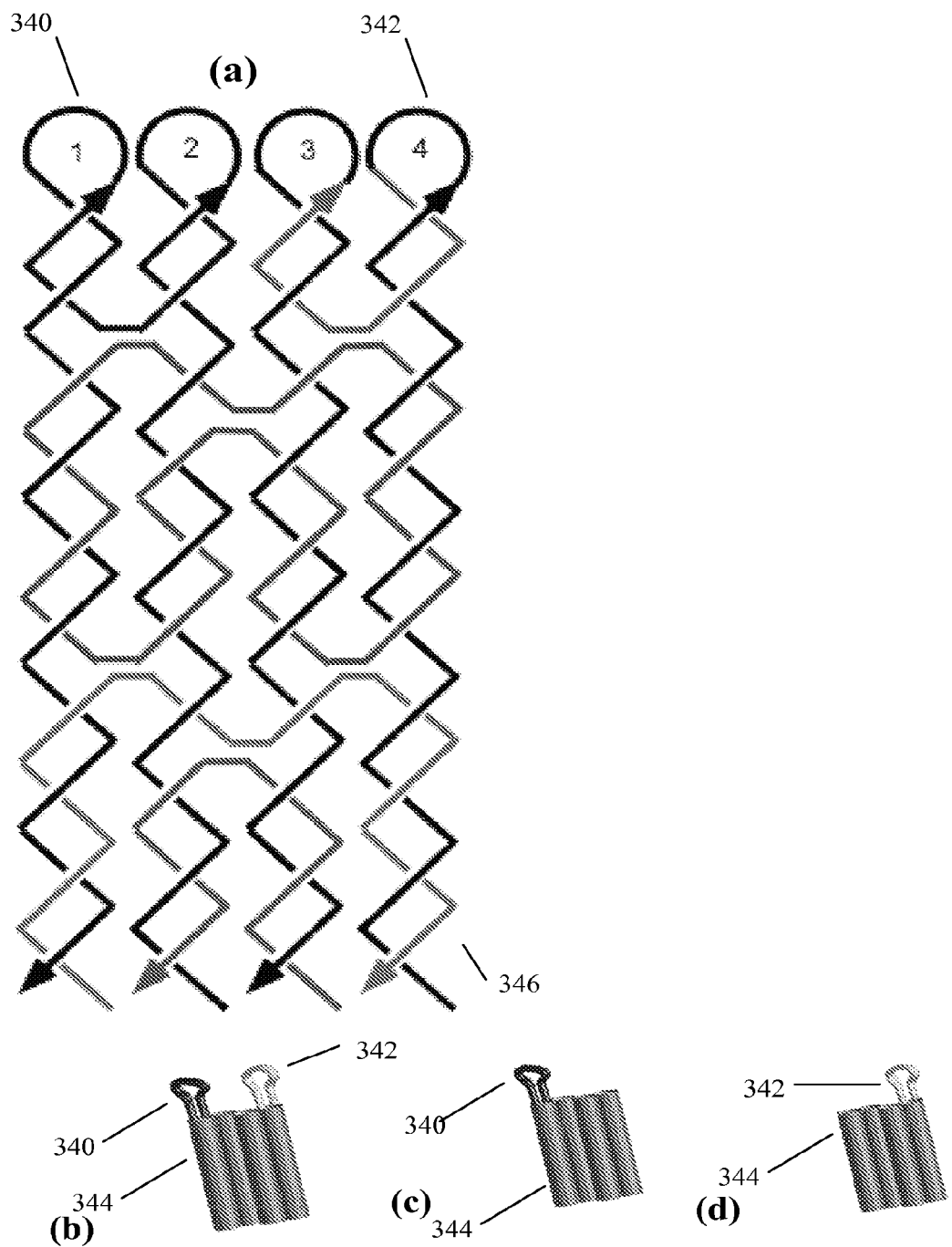
FIG. 26. (a) Schematic of the 4-helix DNA tile linker constructed from DNA oligonucleotides. (b) Location of aptamers specific for thrombin incorporated into the single-stranded DNA loops, providing a structure in which the aptamers extend from the tile as shown schematically. (c) Structure having only a single aptamer containing loop. (d) Another structure having only a single aptamer containing loop.

This example demonstrates the assembly of a synbody having DNA aptamer affinity elements linked by a DNA tile linker, and demonstrates that the synbody so constructed has, with respect to the target used to identify the aptamer affinity elements, an affinity significantly greater than that of either of the aptamer affinity elements with respect to the same target. The 4-helix DNA tile linker was constructed from DNA oligonucleotides as shown schematically in FIG. 26 and described in detail in Ke Y G, Liu Y, Zhang J P, Yan H: A study of DNA tube formation mechanisms using 4-, 8-, and 12-helix DNA nanostructures. Journal of the American Chemical Society 2006, 128(13):4414-4421, which is incorporated by reference herein. The spacing between affinity elements is determined in part by the number of helices and the choice of loops in which to incorporate the aptamer affinity elements; the number of helices and choice of loops may be varied to achieve a desired spacing. The sequences of aptamers specific for thrombin shown in Table 4 were incorporated into the first 340 and fourth 342 single-stranded DNA loops, providing a structure in which the aptamers extend from the tile as shown schematically in FIG. 26(b), with a spacing between aptamers (for the 4-helix tile) of about 2 nm. For comparison and evaluation of binding properties of this two-aptamer synbody structure with similar structures having only a single affinity element, structures were also synthesized having only Apt1 (SEQ ID NO: 20) in the first loop 340 without the presence of Apt2 (SEQ ID NO: 21) (see FIG. 26(c)) and having only Apt2 (SEQ ID NO: 21) in the fourth loop 342 without the presence of Apt1 (SEQ ID NO: 20) (see FIG. 26(d)).

TABLE 4

Aptamer sequences used in DNA tile synbody

| | Sequence | Source |
|---|---|---|
| Apt1 | 5'-AGTCCGTGGTAGGGCAGGTTGGGGTGACT-3' (SEQ ID NO: 20) | Tasset DM, Kubik MF, Steiner W: Oligonucleotide inhibitors of human thrombin that bind distinct epitopes. *Journal of Molecular Biology* 1997, 272(5): 688-698 |
| Apt2 | 5'-GGTTGGTGTGGTTGG-3' (SEQ ID NO: 21) | Bock LC, Griffin LC, Latham JA, Vermaas EH, Toole JJ: Selection of single-stranded-DNA Molecules that bind and inhibit human thrombin. |

TABLE 4-continued

Aptamer sequences used in DNA tile synbody

| Sequence | Source |
|---|---|
| | Nature 1992, 355(6360):564-566) |

By gel shift assay, binding of the DNA tile synbody (FIG. 26(b)) to thrombin was evaluated and compared with the binding to thrombin of each aptamer incorporated into its loop of the DNA tile without the other aptamer present (FIGS. 26(c) and (d)). Non-denaturing (8% polyacrylamide) gel electrophoresis was performed at 25° C. with constant 200V for 5 hours with 1nM of pre-annealed Sybr-Gold stained tile/aptamer pre-incubated for 1 hr at room temperature with concentrations of human α-thrombin ranging from 0 to 100 nM. In the gel shift assay, the synbody was found to have a IQ with respect to thrombin of about 5 nM, the tile incorporating apt1 (SEQ ID NO: 20) only or apt2 (SEQ ID NO: 21) only had $K_d$ values above 100 nM.

Figure 27:
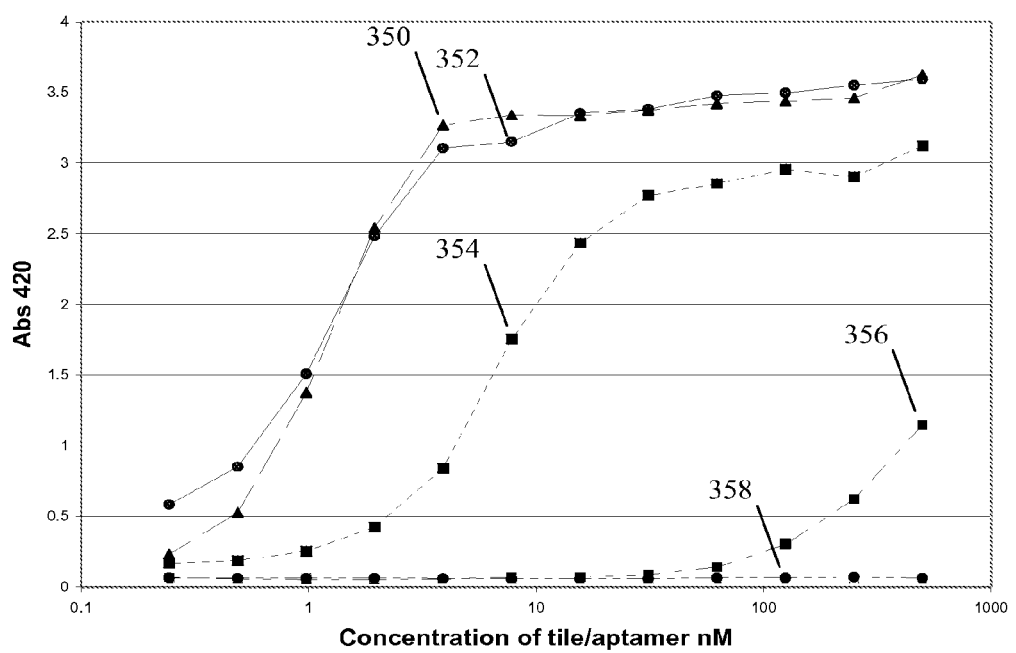
FIG. 27. Graph showing results of thrombin-binding assays on the DNA tile synbodies.
Figure 28:
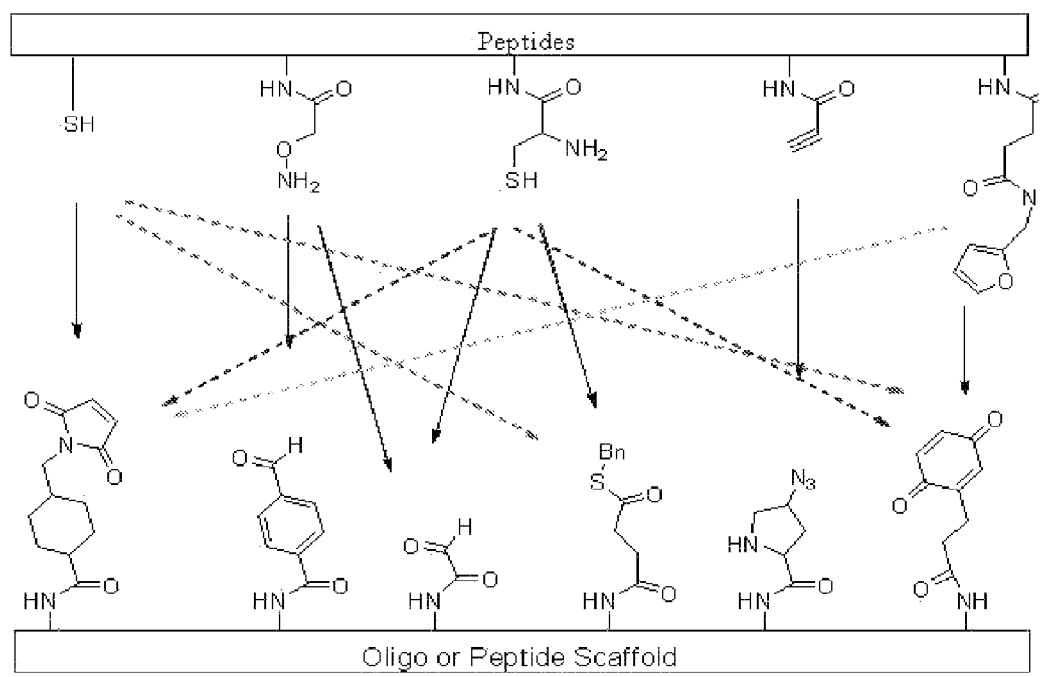
FIG. 28. Pairs of chemical moieties suitable for conjugation by click-type chemistry.
Figure 29:
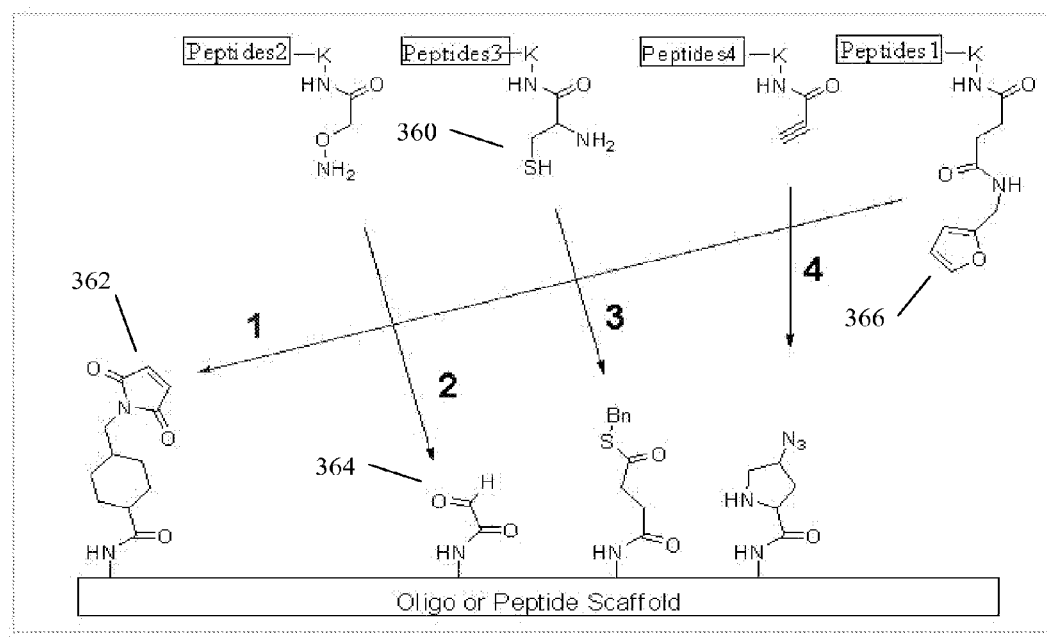
FIG. 29. Four pairs of chemical moieties suitable for conjugation by click-type chemistry that, when conjugations are performed in the order indicated, provide four orthogonal conjugations.

Binding to thrombin was evaluated in an ELISA-type assay. Wells of a 96 well plate were coated with 100 μL of 30 μg/mL human α-thrombin and incubated at 4 C overnight. The plate was washed twice with DDI H2O and passivated with 3% BSA in IX PBS buffer for 1 hour. The plate was shaken out and 50 μL of varying concentrations of analyte (DNA tile synbody, DNA tile with each aptamer with the other not present, and each aptamer alone, respectively) were incubated at RT for 1 hour. DNA tiles were biotin-modified at the 5' end of one of the distal DNA strands 346 (see FIG. 26(a)). The plate was rinsed 10 times in IXPBS and 50 μL of 1:1000 dilution of streptavidin-HRP in 0.1% BSA in IX PBS was pipetted and incubated for 1 hour at RT. The plate was again rinsed and 50 μL of TMB was added and incubated at RT for 15 minutes. 50 μL of 0.5M HCl was added and the plate was read immediately. Results are shown in FIG. 27 for the DNA tile synbody 350; the DNA tile with Apt1 (SEQ ID NO: 20) but not Apt2 (SEQ ID NO: 21) present 352; the DNA tile with Apt2 but not Apt1 (SEQ ID NO: 20) present 356; Apt1 (SEQ ID NO: 20) alone 354; and Apt2 (SEQ ID NO: 21) alone 358. Dissociation constant values estimated from this assay were about 1 nM for the DNA tile synbody, about 10 nM for Apt1 (SEQ ID NO: 20) alone, and more than 1 μM for Apt2 (SEQ ID NO: 21) alone.

DNA tiles of other widths were also constructed and aptamer attachments at separation distances of about 2, 4, 6, and 8 nm were evaluated by non-denaturing gel shift assay (6% polyacrylamide). The 6 nm separation produced an approximately two-fold improvement of estimated $K_d$ in comparison to the 2, 4, or 8 nm separation ($K_d$ estimated about 2 nM for the 2 nm separation vs. about 1 nM for the 6 nm separation.

Example 13

Linkers

The linker employed in the compositions and methods disclosed herein may be any structure, comprising one or more molecules, operable for associating two or more affinity elements together in a manner such that the resulting synbody has, with respect to a target of interest, affinity and/or specificity superior to that of the affinity elements when not so associated. In various embodiments, the linker may be a separate structure to which each of the two or more affinity elements is joined, and in other embodiments, the linker may be integral with one or both affinity elements. In some embodiments, it is desirable to choose linker structures that are stable and reasonably soluble in an aqueous environment, and amenable to efficient and specific chemistries for attaching affinity elements in a desired position and/or conformation.

Without limiting the generality of the foregoing, this prospective example demonstrates several linker compositions and chemistries for attaching affinity elements thereto, in addition to the DNA linkers and lysine linkers described in other examples.

Polyproline and variants thereof may be used as a linker in some embodiments. Polyproline forms a relatively rigid and stable helical structure with a three-fold symmetry, so that attachment sites spaced at three residue intervals are approximately aligned with respect to their angular relationship to the axial dimension. The distance between such attachment sites (three residues apart) is about 9.4 A for polyproline II, in which the peptide bonds are in trans conformation, and about 5.6 A for polyproline I, in which the peptide bonds are in cis conformation. Hydroxyproline may be substituted for proline in these constructs, to provide a more hydrophilic structure and improve solubility. See Schumacher M, Mizuno K, Chinger H P B: The Crystal Structure of the Collagen-like Polypeptide (Glycyl-4(R)-hydroxyprolyl-4(R)-hydroxyprolyl)9 at 1.55.ANG. Resolution Shows Up-puckering of the Proline Ring in the Xaa Position. Journal of Biological Chemistry 2005, 280(21): 20397-20403, which is incorporated herein by reference.

Figure 38:
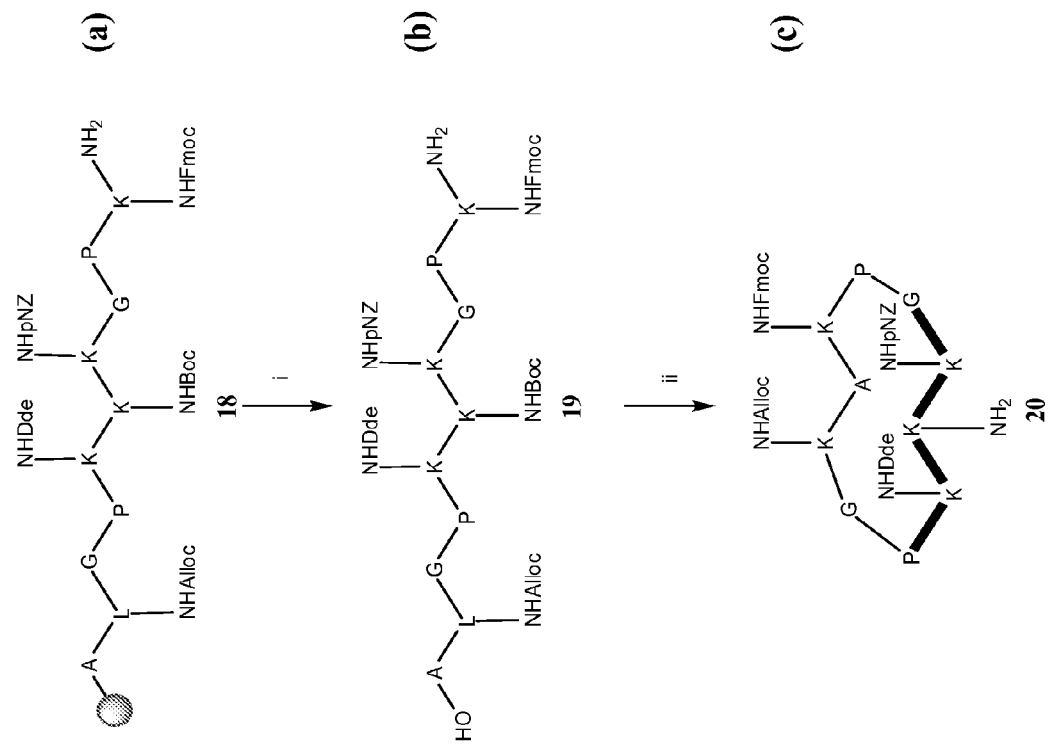
FIG. 38. Diagram showing synthesis of decapeptide scaffold suitable for use as a synbody linker.
Figure 39:
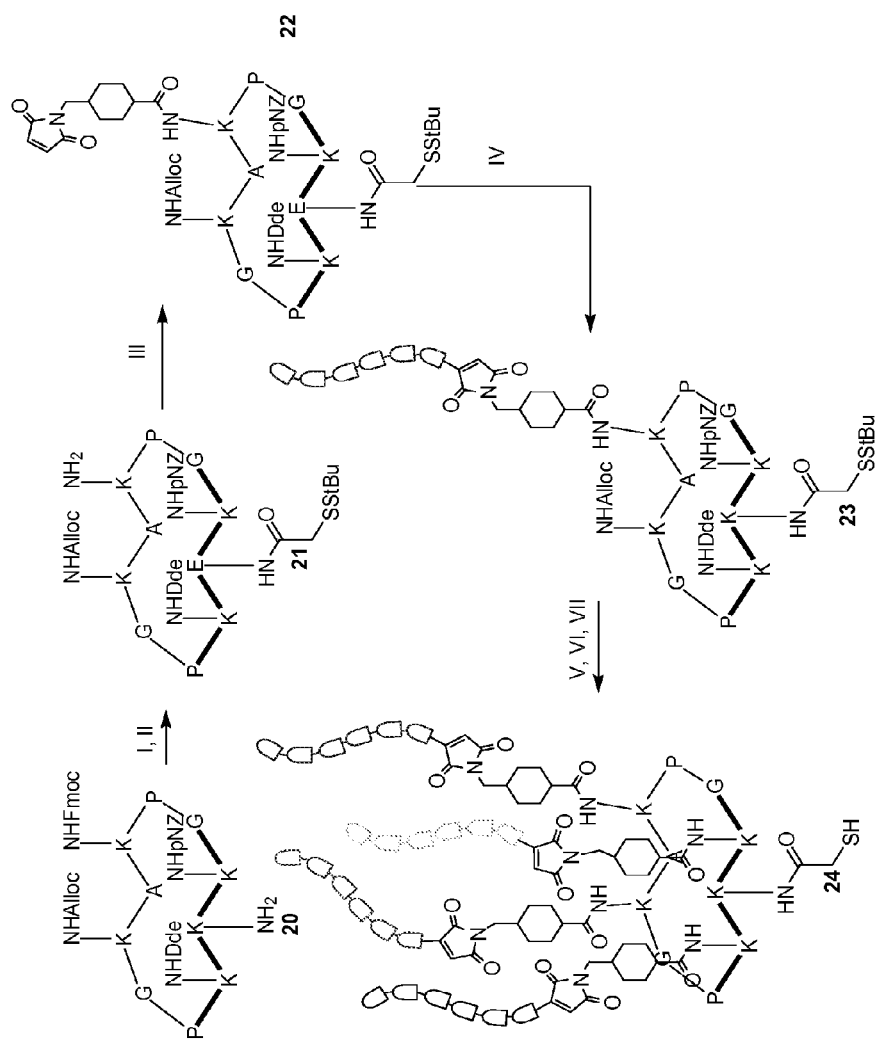
FIG. 39. Diagram illustrating orthogonal conjugation of affinity elements to decapeptide scaffold linker.

In general, synbodies comprising affinity elements and linkers that can be synthesized by standard solid phase synthesis techniques can be synthesized either by addition of amino acids or other monomers in a stepwise fashion, or by joining preassembled affinity elements and linkers or other presynthesized subunits. Techniques for stepwise synthesis of peptides and other heteropolymers are well known to persons of skill in the art. See, e.g., Atherton E, Sheppard R C: Solid Phase peptide synthesis: a practical approach. Oxford, England: IRL Press; 1989, and Stewart J M, Young J D: Solid Phase Peptide Synthesis, 2d Ed. Rockford: Pierce Chemical Company; 1984, which are incorporated herein by reference.

Where synbodies are constructed by joining presynthesized entities, it may be desirable to employ conjugation chemistries and methods that are orthogonal, so that conjugation points can be deprotected and added to without risking inadvertent deprotection or modification of other addition points, and that are rapid and high yield, so that adequate product is produced. FIG. 38 enumerates a number of conjugation pairs (pairs are denoted by the arrows in FIG. 38) each comprising a chemical moiety to be present on a peptide or other affinity element and another chemical moiety to be present on the oligonucleotide, peptide scaffold, or other linker, where the two members of the pair will react to form a covalent linkage under conditions that will be readily determinable by persons of ordinary skill in the art guided by the disclosures hereof. It will be seen that certain of the "click" moieties shown in FIG. 38 are capable of conjugating with more than one other moiety; where such moieties are employed, it may be necessary to perform the desired conjugations in an appropriate order so that the desired conjugation takes place at any moieties that are susceptible to reaction with more than one other moiety before such other moieties are applied. FIG. 39 shows an illustrative example in which four orthogonal conjugations are achieved performing four "click" reactions, which should preferably be performed in the order shown (for example, the thiol moiety 360 is intended to react with the aldehyde moiety 364, but can also react with the maleimide moiety 362; this is prevented by reacting the maleimide 362 with its intended click pair 366 first, so that when the thiol 360 is applied no maleimide 362 remains to react with it. The use of "click" chemistry to perform conjugations between biopolymers and other heteropolymers is well within the capability of persons of ordinary skill in the art guided by the disclosures hereof, and is described in detail in various references such as Kolb H C, Finn M G, Sharpless K B: Click chemistry: Diverse chemical function from a few good reactions. Angewandte Chemie-International Edition 2001, 40(11):2004 and Evans R A: The rise of azide-alkyne 1,3-dipolar 'click' cycloaddition and its application to polymer science and surface modification. Australian Journal of Chemistry 2007, 60(6):384-395, which are incorporated herein by reference.

Figure 30:
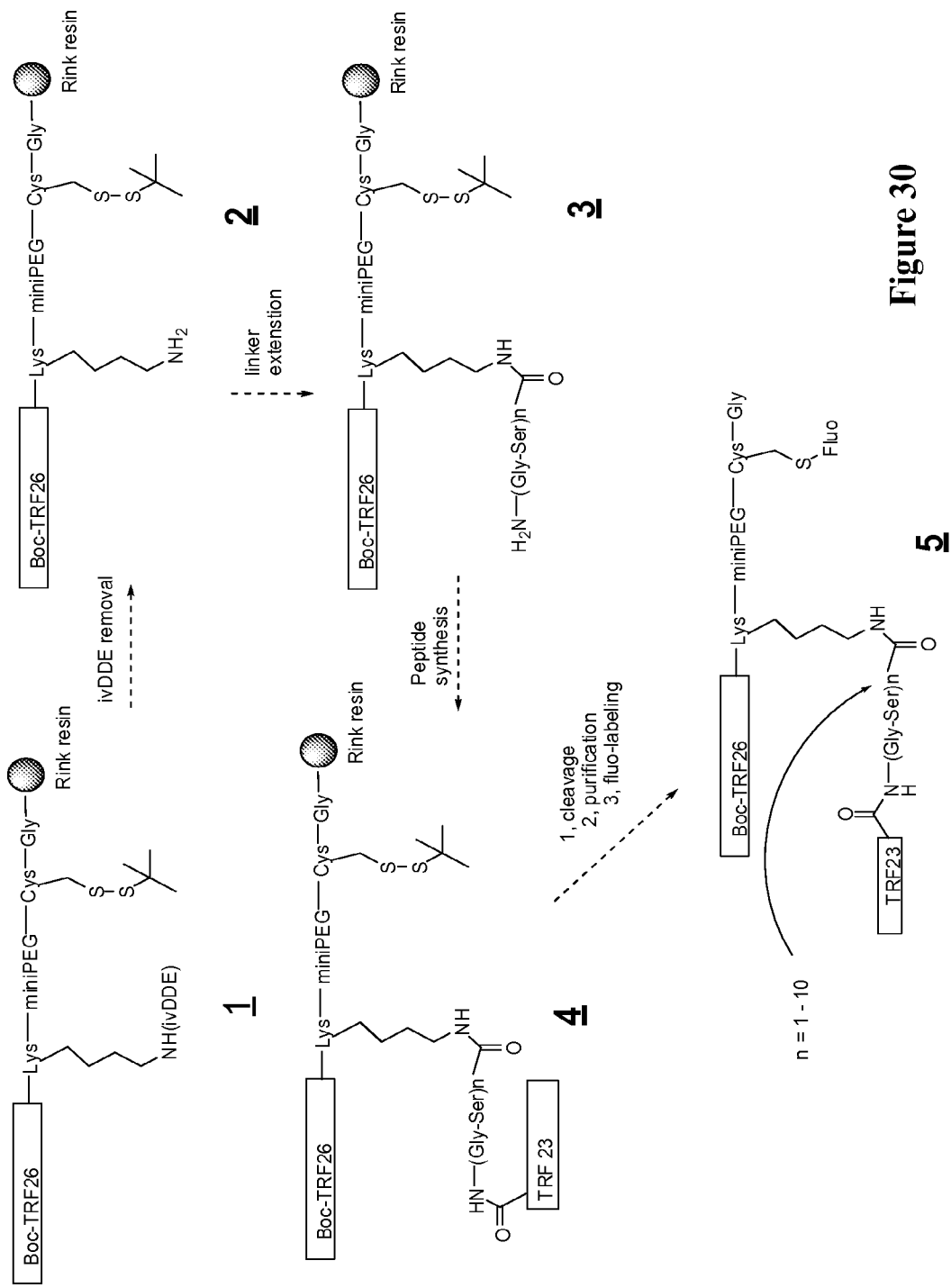
FIG. 30. Diagram of synthesis of a synbody comprising a poly-(Gly-Ser) linker.

FIG. 30 shows the synthesis of a synbody comprising two peptide affinity elements (TRF26 (SEQ ID NO: 8) and TRF23 (SEQ ID NO: 5)) joined by a poly Gly-Ser linker and further comprising a cysteine, attached via a miniPEG, for labeling with a suitable fluorescent label. The entity shown in FIG. 30(1) is first synthesized in large quantity (i.e. 0.5 to 1.0 mmole) in a microwave synthesizer by standard methods. The ivDDE protecting group is then removed and the deprotected product is split into ten aliquots. Again by microwave synthesis, to each aliquot is added a predetermined number of Gly-Ser, ranging from 1 to 10, so that each aliquot now has a linker comprising $(Gly-Ser)_n$ where n is 1 for the first aliquot, 2 for the second, and so on up to 10 (FIG. 30(3)). For each aliquot, the second peptide affinity element, TRF23 (SEQ ID NO: 5), is then synthesized by stepwise addition of amino acids (FIG. 30(4)). The synbody is then cleaved from the resin. The t-butyl thiol protecting group intact on the miniPEG-linked cysteine may be removed and a fluorescent label added if desired (FIG. 30(5)).

Figure 31:
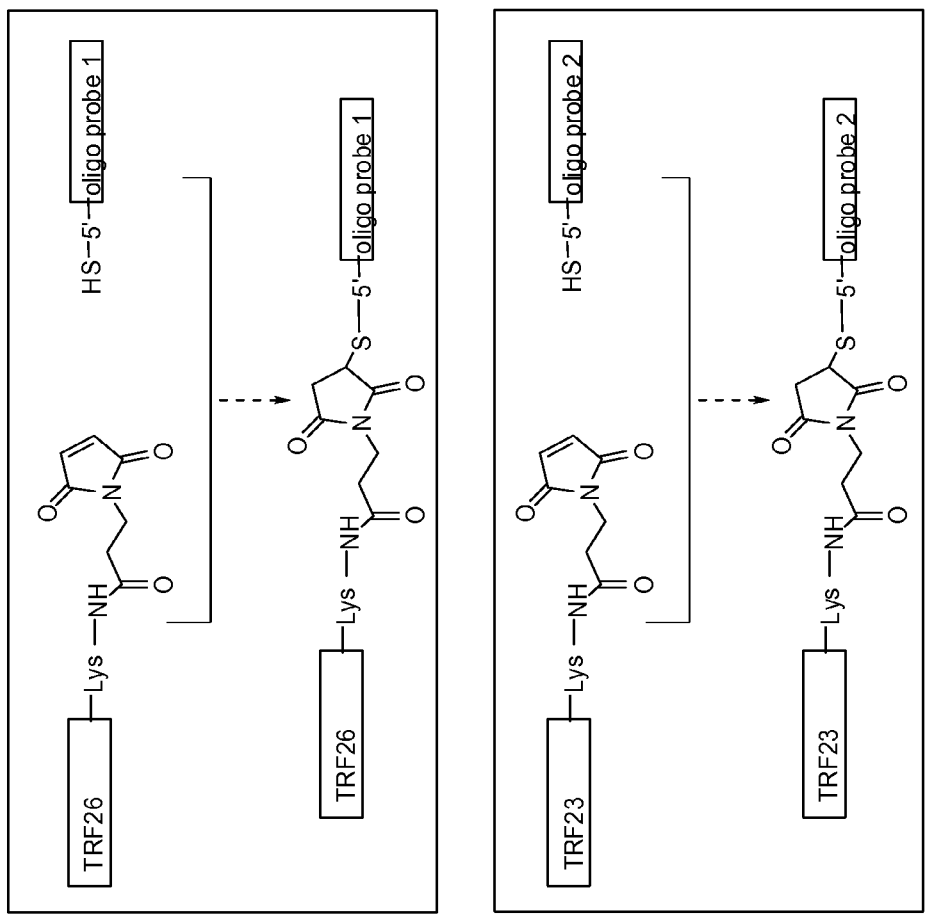
FIG. 31. Diagram showing conjugation of a maleimide functionalized polypeptide with a thiol functionalized oligonucleotide.

FIG. 31 shows the conjugation of a maleimide-functionalized peptide to a thiol-modified oligonucleotide, producing a peptide-oligonucleotide conjugate that may be used to enable the use of peptide affinity elements with the DNA tile linkers of Example 9 above. The oligonucleotide conjugated to the peptide is reverse complementary to an exposed DNA strand of the DNA tile and stably hybridizes thereto.

Figure 32:
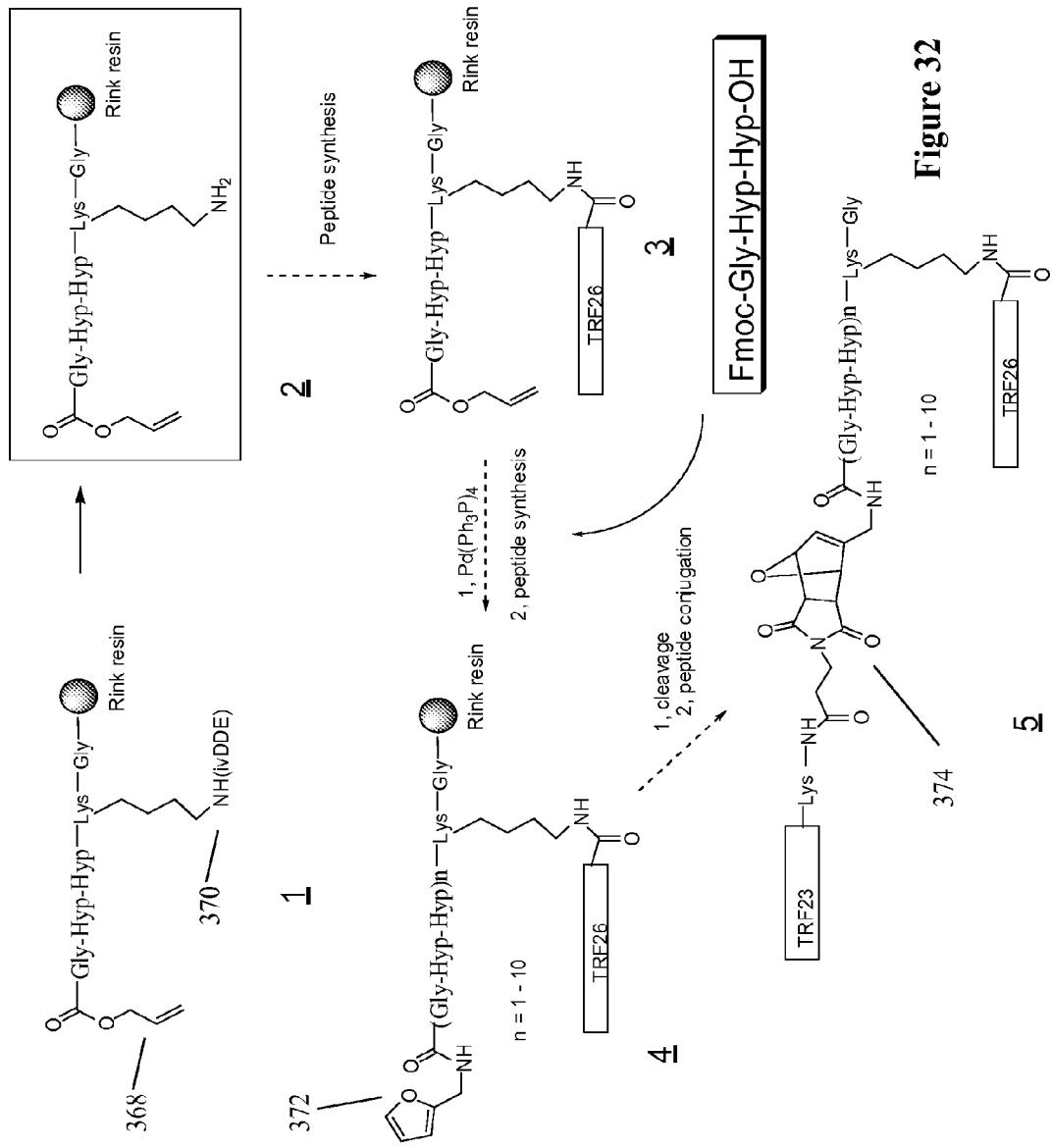
FIG. 32. Diagram of synthesis of a synbody comprising a poly-(Gly-Hyp-Hyp) linker.

FIG. 32 shows the synthesis of a poly-(Gly-Hyp-Hyp)-linked synbody and illustrates a method for improving the ivDDE deprotection (ivDDE deprotection in the presence of a long peptide may be suboptimal due to interference by the peptides with access to an ivDDE that is close to the resin surface). The structure shown in FIG. 32(1) is first synthesized using standard solid phase synthesis techniques. The ivDDE 370 protected lysine is deprotected (FIG. 32(2)) and the first peptide affinity element TFR26 is synthesized by stepwise addition of amino acids (FIG. 32(3)). The alloc protecting group 368 is removed and Fmoc-Gly-Hyp-Hyp-OH subunits are added to the linker to the length desired (FIG. 32(4)). The structure is then cleaved from the resin, and TRF23 (SEQ ID NO: 5), which has been presynthesized with a maleimide functionalization 374 of the terminal lysine, is conjugated to the furanyl moiety 372 of the poly-(Gly-Hyp-Hyp) linker (FIG. 32(5)).

Figure 33:
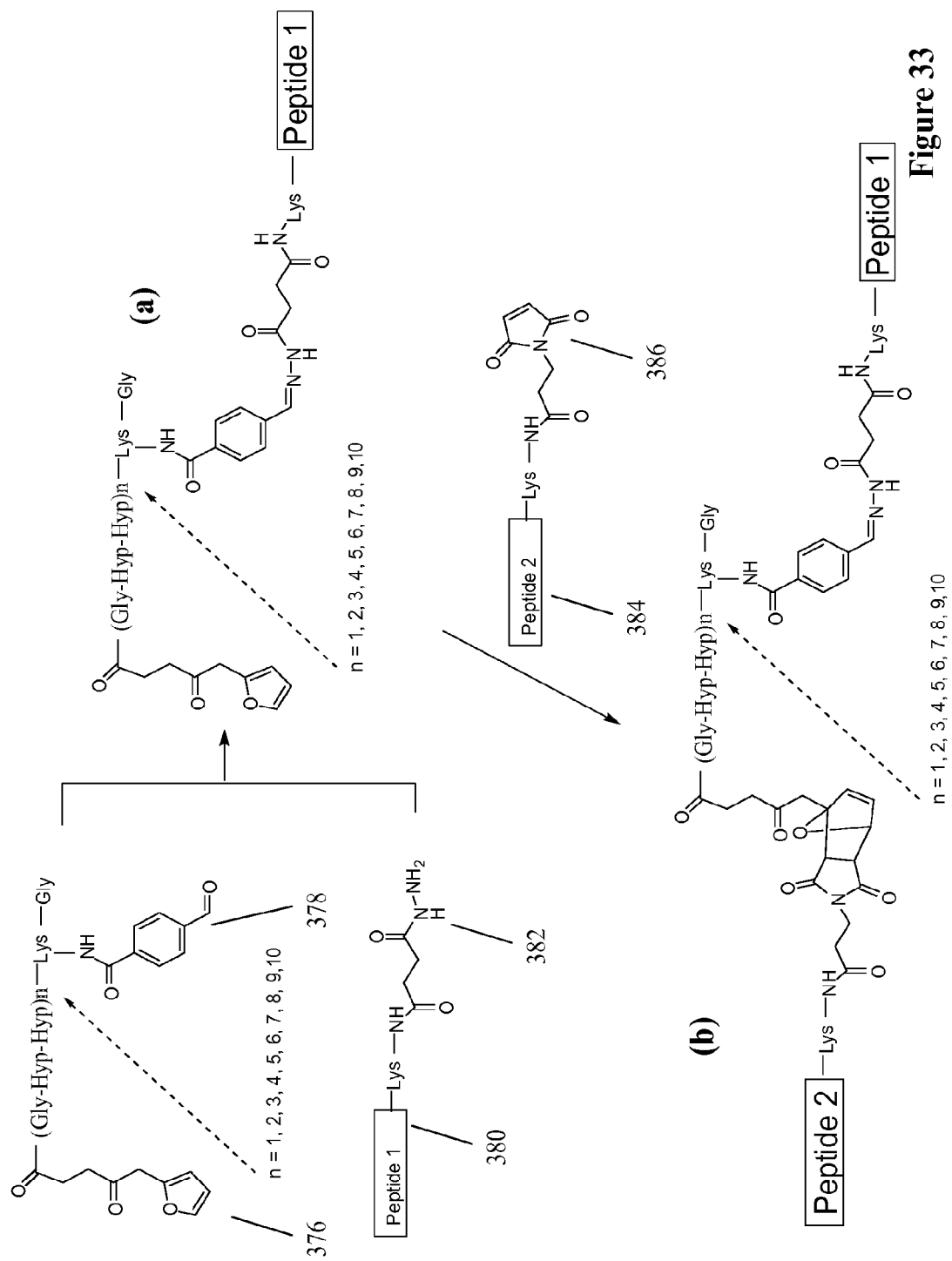
FIG. 33. Diagram of synthesis of a synbody comprising a poly-(Gly-Hyp-Hyp) linker wherein both affinity elements are attached by click-type chemistry conjugation.

FIG. 33 shows the synthesis of synbodies using poly-(Gly-Hyp-Hyp) linkers of varying lengths by attaching both affinity elements using mutually orthogonal conjugations. $(Gly-Hyp-Hyp)n$ linkers of varying lengths from n=1 to n=10 are presynthesized with a furanyl moiety 376 for conjugation of a first affinity element and a benzaldehyde moiety 378 for conjugation of a second affinity element. The first affinity element 380, functionalized with a hydrazide moiety, is conjugated to the benzaldehyde moiety of the poly-(Gly-Hyp-Hyp) linker (FIG. 33(a)). The second affinity element 384, functionalized with a maleimide moiety 386, is conjugated to the furanyl moiety of the linker (FIG. 33(b)). These conjugations can be performed in a reaction mixture containing multiple different linker lengths and/or multiple peptide sequences, enabling production of a combinatorial library representing multiple linker lengths and affinity element combinations, from which constructs that optimally bind the target of interest are identified using an affinity column or other suitable screening method.

Figure 34:
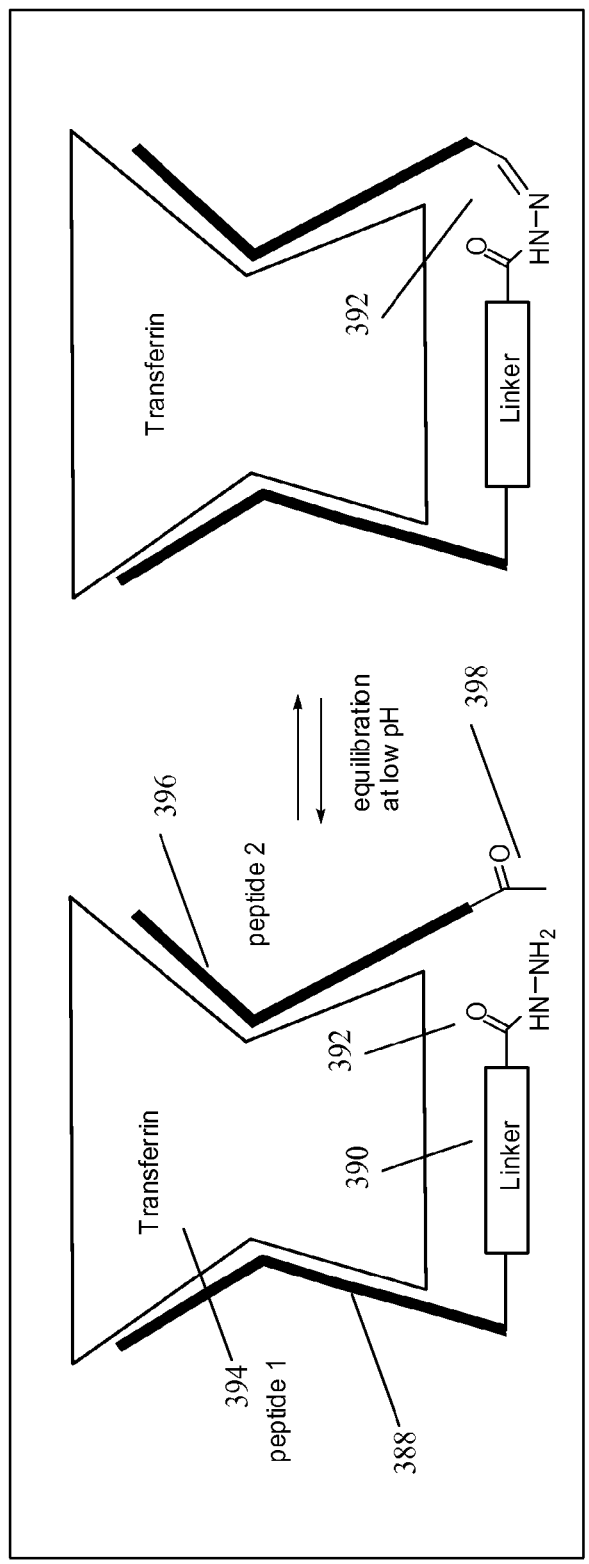
FIG. 34. Schematic illustration of a concept underlying a method for identification of optimized affinity elements and/or linkers by allowing a synbody to self-assemble in association with a target.
Figure 35:
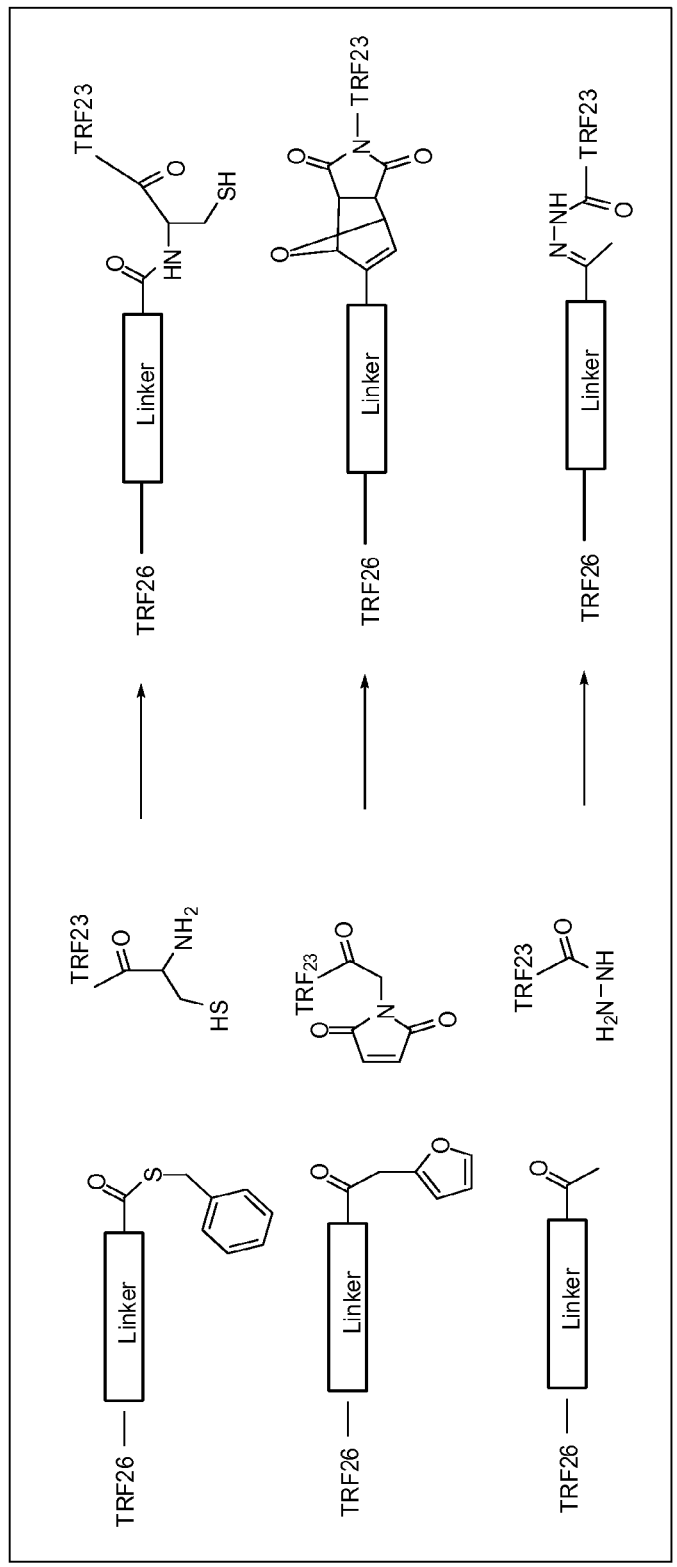
FIG. 35. Diagram showing three potentially reversible conjugation chemistries.

FIG. 34 illustrates schematically a method for determining suitable linker lengths and affinity element sequences by allowing the desired synbody structures to self-assemble in the presence of the target of interest 394 such as transferrin. To a solution containing transferrin 394 are added a first library combining a variety of distinct affinity elements 388 (shown as peptide 1 in FIG. 34) with linkers 390 of a variety of lengths to which the affinity elements are conjugated, each linker 390 being functionalized (at its terminus opposite the attachment point of the affinity element, or other attachment point providing a desired separation and/or orientation) with a moiety 392 suitable for conjugation of a second affinity element 396. A second library comprising a variety of distinct affinity elements 396 (peptide 2 in FIG. 34), each functionalized with a moiety 398 suitable for conjugation with the linker, is added. Affinity elements 388, 396 having affinity for loci on the target 394 will tend to associate with the target in their preferred positions and/or orientations. Where a pair comprising an affinity element 388 plus linker 390 and an affinity element 396 plus conjugation moiety 398 associate with a target molecule in such a way that the conjugation moiety 398 of the affinity element 396 and the conjugation moiety 392 of the linker are in close proximity and appropriately oriented, reaction will occur and a bond 392 will form, linking the two affinity elements into a synbody, whose position and orientation with respect to the target has been determined by the target itself Synbodies bound to the target are then identified and characterized. The concentrations of affinity elements used should preferably be low enough to prevent significant conjugation between affinity elements and linkers that are not associated with a target molecule, but should be high enough so that affinity elements will associate with target for sufficient time to allow the desired pairs to conjugate. Also, the conjugation chemistry should be reversible so as to allow the conjugation process reach an equilibrium that favors the most suitable combinations; several conjugation chemistries that are potentially reversible under appropriate conditions are shown in FIG. 35. (Many other reversible conjugation chemistries are possible; in any, obtaining the desired reversibility will depend upon suitable reaction conditions.)

Example 14

Cyclic Tetrapeptide Linker Synbody

This example demonstrates the synthesis of a cyclic tetrapeptide having three orthogonally protected conjugation sites for attachment of peptide or other affinity elements.

Figure 36:
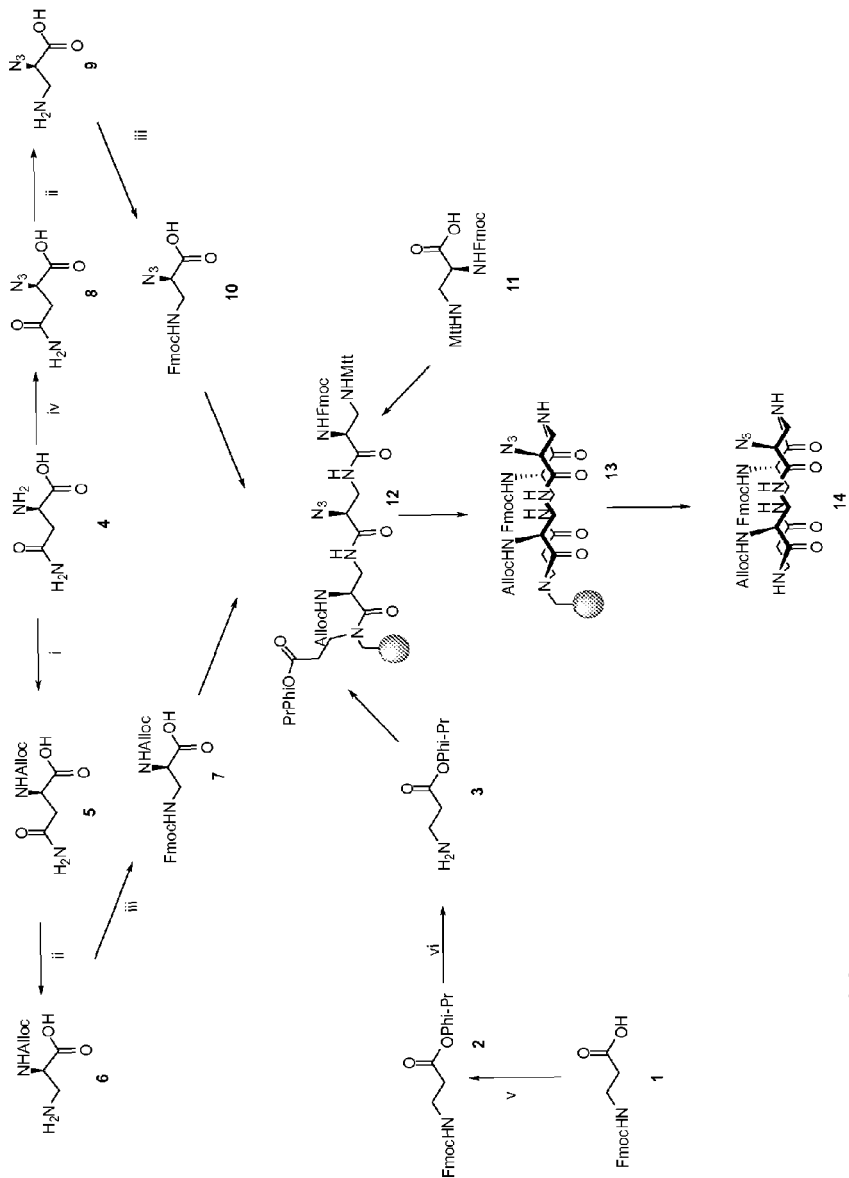
FIG. 36. Diagram showing synthesis of a tetrapeptide scaffold suitable for use as a synbody linker.

The structure shown in FIG. 36 is synthesized from three modified amino acids, and a fourth one that is commercially available, as shown. The three amino acids are first synthesized, and the resin modified; the synthesis of the tetrapeptide is then carried out, and peptides or other affinity elements are added; thus, the tetrapeptide serves as a linker for construction of a synbody.

Synthesis of the modified amino acids. 1-Methyl-1-phenylethyl 3-aminopropanoate (FIG. 36(3)) was synthesized as follows: Over a suspension of NaH (50 mg, 2.1 mmol) in diethyl ether (2 mL), a solution of 2-phenyl-2-propanol (2.5 g, 18.36 mmol) in 2 mL of diethyl ether was added dropwise. The mixture was stirred at room temperature for 20 min and then cooled at 0° C. Trichloroacetonitrile (1.9 mL) was slowly added (for 15 min) and the mixture was allowed to reach room temperature. After 1 hour of stirring, the mixture was concentrated to dryness and the resultant oil was dissolved in pentane (2 mL) and the solution was filtered. The filtrate was evaporated to dryness, to get a very dark oil, that we use immediately in the next reaction. The freshly prepared 1-methyl-1,1-phenylethyl trichloroacetimidate (2.7 g, 6.424 mmol) was added over a solution of Fmoc-β-alanine, (FIG. 36(1)), (1 g, 3.212 mmol) in DCM (8 mL). After overnight stirring, the precipitated trichloroacetamide was removed by filtration, and the filtrate mixture was evaporated to dryness and purified by flash chromatography $CH_2Cl_2$/MeOH (0% to 1%) to yield 1.158 g (84%) of compound 2 as a colorless oil.

In a flask, (FIG. 36(2)) (1.158 g, 2.698 mmol) was dissolved in DCM (4 mL), and diethylamine (12 mL) was added. Immediately, the mixture becomes clear. The mixture was stirred for 2 hours. After adding 20 mL of toluene, the mixture was concentrated to dryness and the separation carried out by flash chromatography, using 10% of $CH_2Cl_2$/MeOH and 2% of $Et_3N$ to yield 526 mg (94%) of (FIG. 36(3)) as a colorless oil.

$N^2$-(allyloxycarbonyl)-$N^3$-(9-fluorenylmethoxycarbonyl)-2,3-diaminopropanoic acid (7) was synthesized as follows: Over a solution of 2 g of asparagine (FIG. 36(4), 15.138 mmol) in 3.78 mL of 4M NaOH solution cooled in an ice-bath, 1.615 mL of allyl chloroformate (15.138 mmol) and 3.78 mL of 4M NaOH solution in portions were added. The reaction was kept alkaline and stirred for 15 minutes at room temperature. The mixture was extracted with ether and acidified with concentrated HCl, so the product was crystallized, filtrated, and lyophilized to afford (FIG. 36(5)) (2.816 g, 86%) as a white solid. [Bis(trifluoroacetoxy)iodo]benzene (8.402 g, 19.539 mmol) was added to a mixture of (FIG. 36(5)) (2.816 g, 13.026 mmol) and aqueous DMF (140 mL, 1:1, v/v). The mixture was stirred for 15 min, and DIEA (4.54 mL, 26.052 mmol) was added. After 8 hours the reaction, only half of the reaction went. So, the same quantities of [Bis(trifluoroacetoxy)iodo]benzene and DIEA were added, and the reaction was stirred overnight. The next day, the solution was concentrated to dryness, the residue solved in 100 mL of water and the organic side products were removed by repeated washings with diethyl ether (4×100 mL). The water phase was evaporated to dryness to yield product (FIG. 36(6)) that was used in the next reaction without further purification.

The oil previously obtained ((FIG. 36(6)) was redissolved in water (20 mL), and DIEA (2.24 mL, 13.026 mmol) and FmocOSu (4.393 g, 13.026 mmol) in acetonitrile (15 mL) were added, and the reaction was allowed to stir for 1.5 h. The mixture was acidified (to pH 2.0) by addition of HCl, and the product was extracted in DCM (5×40 mL). The organic phases were combined, dried with $Na_2SO_4$, and evaporated to dryness. The crude product mixture was purified by flash chromatography (10% MeOH in DCM). Hexane was added to the combined product fractions, and the precipitate formed was filtered and washed with hexane, and dried to yield a white solid (FIG. 36(7)).

2-azido-3-[(9-fluorenylmethyloxycarbonyl)amino]-propanoic acid (10) was synthesized as follows: A solution of $NaN_3$ (9.841 g, 151.38 mmol) in 25 mL of $H_2O$ was cooled in an ice bath and treated with 50 mL of $CH_2Cl_2$. The biphasic mixture was stirred vigorously and treated with $Tf_2O$ (8.542 g, 282.14 mmol) for over a period of 30 min. The reaction mixture was stirred at ice bath temperature for 2 h. After quenching with aqueous $NaHCO_3$, the layers were separated, and the aqueous layer was extracted twice with $CH_2Cl_2$ (2×50 mL). The organic layers were combined to afford 100 mL of $TfN_3$ solution that was washed once with $Na_2CO_3$ and used in the next reaction without further purification.

To a solution of L-asparagine (FIG. 36(4)) (2 g, 15.138 mmol) in 50 mL of $H_2O$ and 100 mL of MeOH were added: $K_2CO_3$ (3.138 g, 22.707 mmol), $CuSO_4$ (38 mg, 0.151 mmol), and the solution of $TfN_3$ in $CH_2Cl_2$ previously prepared. The reaction was stirred at room temperature overnight. Then, solid $NaHCO_3$ (10 g) was added carefully, and the organic solvents evaporated. Concentrated HCl was added to the aqueous solution to obtain pH=6, and 100 mL of 0.25 M PBS was added. Then, ethyl acetate (3.times.150 mL) was used to do extractions. Next, more concentrated HCl was used to reach pH=2 and new extractions were carried out with ethyl acetate (5.times.150 mL) and the extract concentrated to dryness to afford a yellow oil (FIG. 36(8)), that was used in the next reaction without further purification.

The oil previously obtained (FIG. 36(9)) was redissolved in water (20 mL), and DIEA (2.6 mL, 15.138 mmol) and FmocOSu (5.106 g, 15.138 mmol) in acetonitrile (15 mL) were added, and the reaction was allowed to stir for 1.5 h. The mixture was acidified (to pH 2.0) by addition of HCl, and the product was extracted in DCM (5×40 mL). The organic phases were combined, dried with $Na_2SO_4$, and evaporated to dryness. The crude product mixture was purified by flash chromatography (10% MeOH in DCM). Hexane was added to the combined product fractions, and the precipitate formed was filtered and washed with hexane, and dried to yield a white solid (FIG. 36(10)).

Derivatization of the resin. mixture of Boc- and Fmoc-β-alanine (2.0 eq of both, 4.0 equiv of TBTU, 8 equiv of DIEA in DMG, 1 h at 25° C.) was coupled to aminomethyl polystyrene resin (1.0 g, 0.5 mmol/g). 50% TFA in DCM was used to remove the Boc groups, and the exposed amino groups were capped with acetanhydride treatment. Thus, the loading of the resin was reduced to 0.16 mmol/g. A treatment of 20% piperidine in DMF was used to remove the Fmoc groups, and 4-(4-formyl-3,5-dimethoxyphenoxy)butyric acid was attached by HATU-promoted coupling to obtain the derivatized resin.

Synthesis of the scaffold on the resin. Previously derivatized resin (1.0 g, a loading of 0.16 mmol/g) was treated for 1 h at room temperature with a mixture of 1-methyl-1-phenylethyl 3-aminopropanoate (FIG. 36(3), 160 mg, 4 equiv) and NaCNBH₃ (48 mg, 4 equiv) in DMF, containing 1% (v/v) AcOH (16 mL). The resin was washed with DMF, DCM, and MeOH and dried on a filter.

The secondary amine was acylated with Aloc-Dpr(Fmoc)-OH 7 (5.0 equiv), using 5 equiv of PyAOP and 10 equiv of DIEA in DMF-DCM, 1:9, v/v for 2 h at 25° C. The Fmoc group was removed by treatment of piperidine-DMF, 1:4, v/v, for 20 min at 25° C. Couplings of 2-azido-3-[(9-fluorenylmethyloxycarbonyl)amino]propanoic acid (FIG. 46(10)) and Fmoc-Dpr-(Mtt)-OH (11) were carried out in each case, by treatment with 5 equiv of the amino acid, 5 equiv of HATU and 10 equiv of collidine in DMF for 1 h at 25° C. to afford product (FIG. 36(12))). The removal of Mtt and PhiPr protections was carried out by treatment with a solution of TFA in DCM (1:99, v/v, for 6 min at 25° C.), followed by immediate neutralization by washings with a mixture of Py in DCM (1:5, v/v). Cyclization of the peptide (FIG. 36(13)) was then performed using PyAOP as an activator (5 equiv of PyAOP, 5 equiv of DIEA in DMF for 2 h at 25° C.). After each coupling (including the cyclization step), potentially remaining free amino groups were capped by an acetic anhydride treatment.

Then, the resin was treated with TFA in DCM (1:1, v/v, 30 min at 25° C.) to release the final product (FIG. 36(14)).

Figure 37:
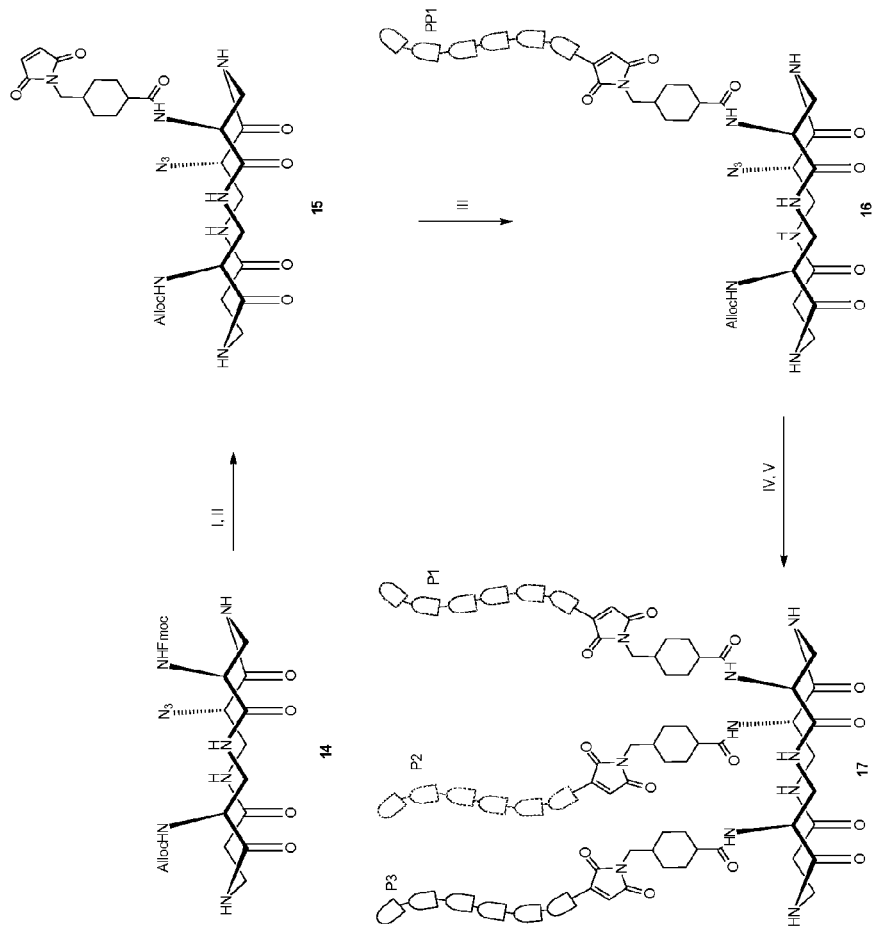
FIG. 37. Diagram illustrating orthogonal conjugation of up to three affinity elements to tetrapeptide scaffold linker.

Sequential addition of peptides to the scaffold. The three amino acid residues can be sequentially deprotected, reacted with sulfosuccinimidyl-4-(N-maleimidomethyl)cyclohexane-1-carboxylate (Sulfo-SMCC) or other heterobifunctional linker, and the corresponding peptide added. Thus, this scaffold allows incorporation of up to three same or different peptides as shown in FIG. 37. Peptides are chosen based on screening of target on a random peptide microarray as described in preceding examples.

Example 15

Cyclic Decapeptide Linker Synbody

This example demonstrates the synthesis of a cyclic decapeptide scaffold from commercial Fmoc amino acids by solid phase synthesis, using Trt-Lys(Fmoc)OH as the N-terminal amino acid, and SASRIN resin as shown in FIG. 38. The cyclization of the decapeptide is carried out in high dilution. This decapeptide structure provides orthogonally protected conjugation sites enabling attachment of up to four distinct peptides or other affinity elements, and thus serves as a linker for the synbody.

Synthesis of the decapeptide H₂NLys(Fmoc)ProGlyLys (pNz)Lys(Boc)ProGly-Lys(Aloc)AlaOH (SEQ ID NO: 24) (FIG. 38(b)). Assembly of the protected peptide was carried out manually. Fmoc-Ala-SASRIN (0.5 g, 0.75 equiv/g) was washed and swollen with CH2Cl2 (2×10 mL×15 min) and DMF (2×50 mL×15 min). Coupling reactions were performed using, relative to the resin loading, 4 equiv of N-α-Fmoc-protected amino acid activated in situ with 4 equiv of PyBOP and 8 equiv of DIEA in 8 mL of DMF for 30 min. The completeness of each coupling was confirmed by Kaiser tests. N-α-Fmoc protecting groups were removed by treatment with piperidine:DMF 1:4 (10 mL.times.4.times.10 min), the completeness of each deprotection being verified by the UV absorption of the piperidine washings at 299 nm.

Peptide resin was treated repeatedly with TFA:CH₂Cl₂ 1:99 until the resin beads became dark purple (10×10 mL×3 min). Each washing solution was neutralized with pyridine:MeOH 1:4 (5 mL). The combined washings were concentrated under reduced pressure, and white solid was obtained by precipitation from EtOAc/petroleum ether. This solid was dissolved in EtOAc, and pyridinium salts were extracted with water. The organic layer was dried over Na₂SO₄, filtered, and concentrated to dryness. Precipitation from CH₂Cl₂/Et₂O afford white solid which was further desalted by solid-phase extraction and lyophilized to afford the linear peptide. This material was used in the next step without further purification.

Cyclization in solution (FIG. 38(c)). The above linear peptide was dissolved in DMF (100 mL), and the pH was adjusted to 8-9 by addition of DIEA. HATU (1.1 equiv) was added, and the solution was stirred at room temperature for 3 h. Solvent was removed in vacuo; the residue was dissolved in TFA:CH₂Cl₂ 1:1 (15 mL) and allowed to stand for 45 min at room temperature. The solution was then concentrated under reduced pressure and the residue was triturated with Et₂O and filtered to yield the crude product shown in FIG. 38(c). The scaffold can be functionalized in order to attach it to different surfaces, or to add a dye that will help in the studies.

Addition of linker. The scaffold can be functionalized in order to attach it to different surfaces, or to add a dye that will help in the studies. Thus, the linker in can be engineered to have a thiol (SH) group at a terminal position. This thiol can be oxidized to yield a dimer of the scaffold with attached affinity elements. Also, the thiol can be used to attach the structure to various other scaffolds and surfaces. The functionalization takes place at the free NH₂ group as shown in FIG. 39. As an example, this amino group can be acylated using tert-butylthio protected thioglycolic acid. At this point, the scaffold is ready for sequential addition of peptides of interest.

Sequential addition of peptides to the scaffold. The four lysine residues can be orthogonally (without affecting each other) deprotected, reacted with sulfosuccinimidyl-4-(N-maleimidomethyl)cyclohexane-1-carboxylate (Sulfo-SMCC) or other similar heterobifunctional linker, and the corresponding NH₂-protected peptide added. Thus, this scaffold allows incorporation of up to four different peptides as shown in FIG. 39.

The linker shown in FIG. 39 can be engineered to have a thiol (SH) group at a terminal position. This thiol can be oxidized to yield a dimer of the scaffold with attached affinity elements. Also, the thiol can be used to attach the structure to various other scaffolds and surfaces.

Example 16

PGP Linker Synbody

Figure 40:
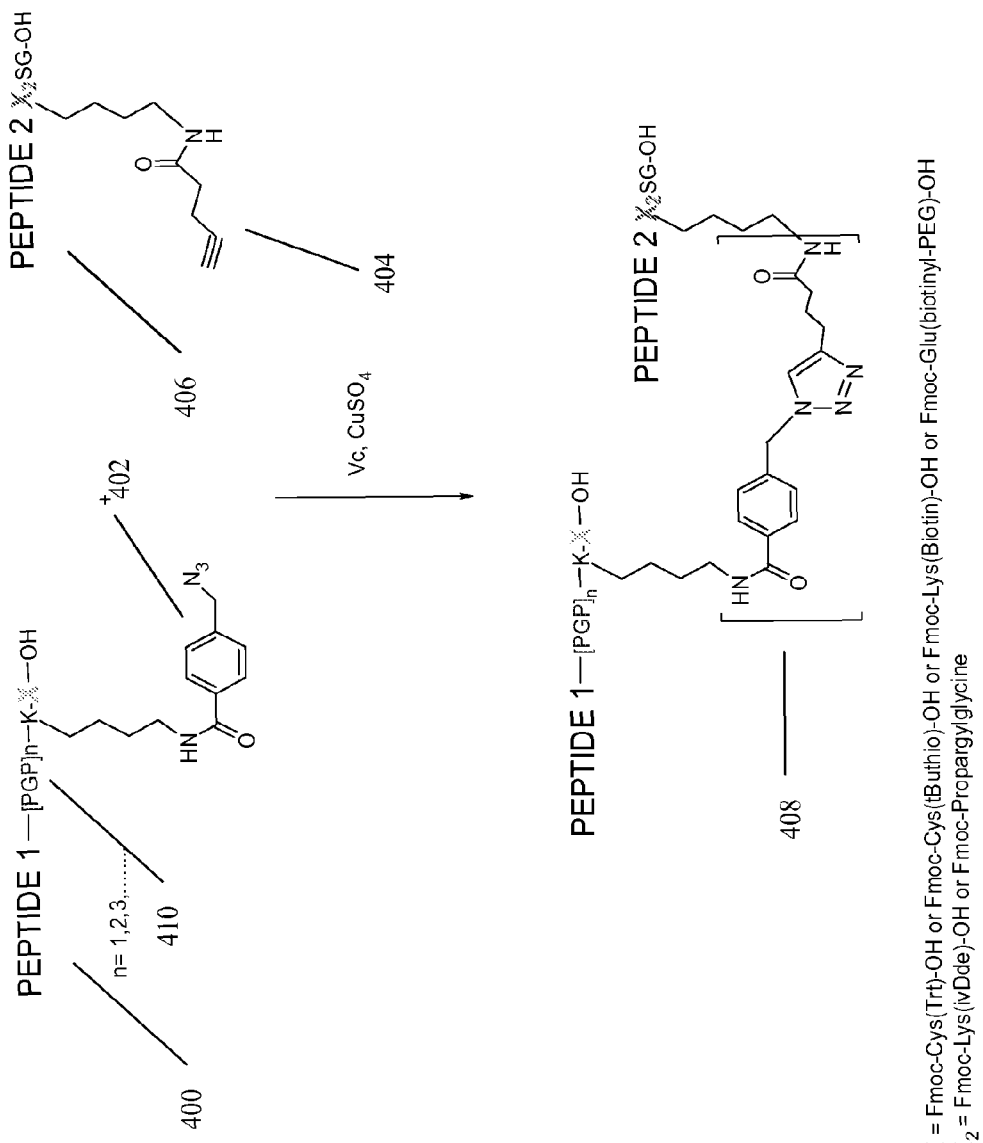
FIG. 40. A structure is shown comprising a polypeptide affinity element, a poly- (Pro-Gly-Pro) linker, and an azide moiety attached to lysine.

This example demonstrates the synthesis of a synbody having polypeptide affinity elements joined by a poly-(Pro-Gly-Pro) linker, whose length can be determined by inserting the desired number of (Pro-Gly-Pro) subunits, and its assembly by click conjugation. As shown in FIG. 40, standard solid phase peptide synthesis methods were used to synthesize, on a Symphony peptide synthesizer, the structure shown in FIG. 40, comprising a polypeptide affinity element 400, a poly-(Pro-Gly-Pro) linker 410, and an azide moiety attached to lysine 402 as shown. A second structure, comprising a second polypeptide affinity element 406, and having an alkyne moiety 404 as shown, was separately synthesized. The two structures were reacted in solution in the presence of vitamin C and CuSO₄ to produce the linked synbody structure 408. Synthesis of the correct synbody structure was verified by MALDI.

In this method, any linker can be used that can be incorporated in the affinity element/linker/azide structure during solid phase synthesis; thus, this method provides a way of testing a variety of linker compositions.

Figure 41:
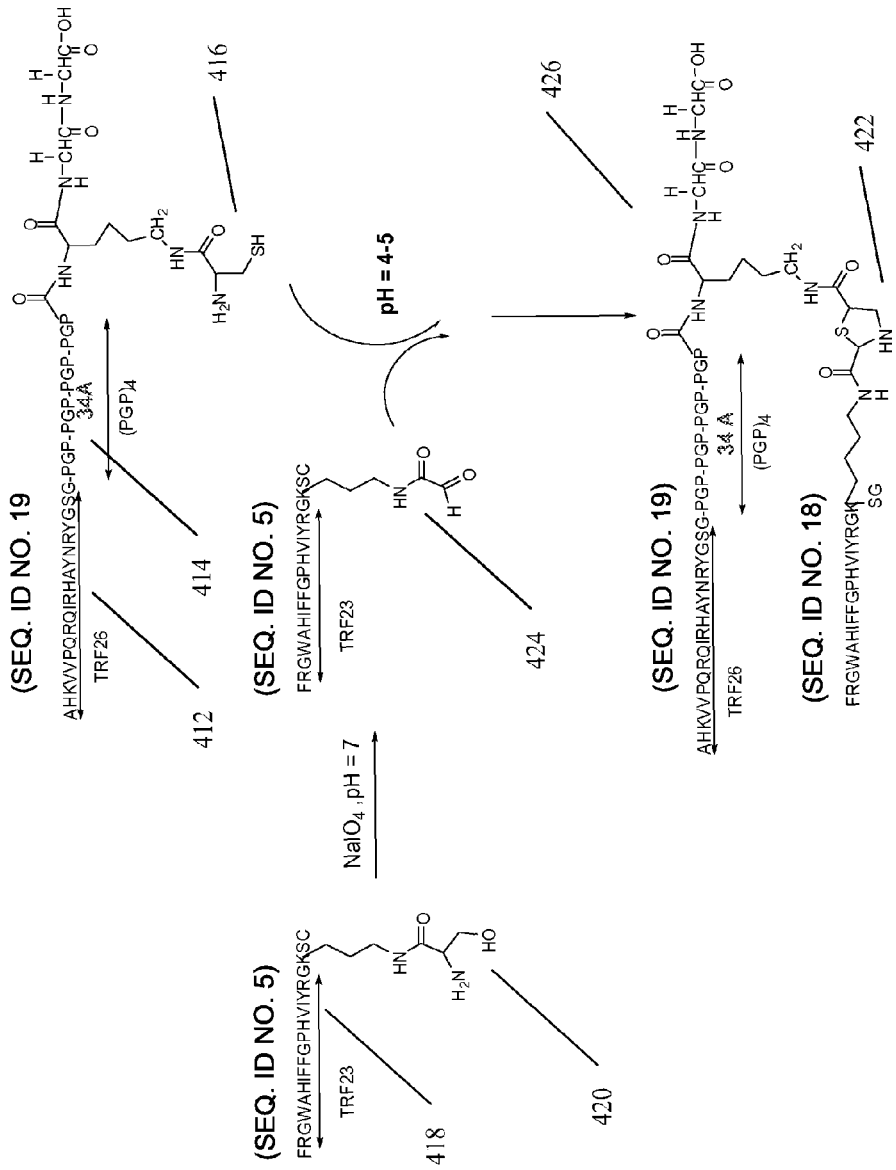
FIG. 41. A poly-(Pro-Gly-Pro) linked synbody is shown as constructed by the thiazolidine formation process.

A poly-(Pro-Gly-Pro) linked synbody was also constructed by the thiazolidine formation process shown in FIG. 41. In this synthesis, a polypeptide affinity element TRF 26 (SEQ ID NO. 8) 412 was synthesized together with its poly-(Pro-Gly-Pro) linker 414 by standard solid phase peptide synthesis methods, having a cysteine residue 416 at or near the opposite end of the linker from the polypeptide affinity element 412 as shown. A second polypeptide affinity element TRF 23 (SEQ ID NO. 5) 418 was synthesized having a serine residue 420 near its C terminus, which was modified as shown 424. The two entities were reacted in solution at pH 4.5 to produce the thiazolidine ring linkage 422 shown. Synthesis of the correct synbody structure 426 was verified by MALDI.

REFERENCES

1. Tang, D. C., DeVit, M. & Johnston, S. A. Genetic immunization is a simple method for eliciting an immune response. Nature 356, 152-4 (1992).
2. Chambers, R. S. & Johnston, S. A. High-level generation of polyclonal antibodies by genetic immunization. Nat Biotechnol 21, 1088-92 (2003).
3. Barry, M. A., Barry, M. E. & Johnston, S. A. Production of monoclonal antibodies by genetic immunization. Biotechniques 16, 616-8, 620 (1994).
4. Hust, M. & Dubel, S. Phage display vectors for the in vitro generation of human antibody fragments. Methods Mol Biol 295, 71-96 (2005).
5. Ellington, A. D. & Szostak, J. W. In vitro selection of RNA molecules that bind specific affinity elements. Nature 346, 818-22 (1990).
6. Binz, H. K., Amstutz, P. & Pluckthun, A. Engineering novel binding proteins from nonimmunoglobulin domains. Nat Biotechnol 23, 1257-68 (2005).
7. Peng, L. et al. Combinatorial chemistry identifies high-affinity peptidomimetics against alpha(4)beta(1) integrin for in vivo tumor imaging. Nat Chem Biol 2, 381-9 (2006).
8. Masip, I., Perez-Paya, E. & Messeguer, A. Peptoids as source of compounds eliciting antibacterial activity. Comb Chem High Throughput Screen 8, 235-9 (2005).
Roque, A. C. A., Lowe, C. R., & Taipa, M. A. "Antibodies and Genetically Engineered Related Molecules: Production and Purification." Biotechnol. Prog. 20, 639-654 (2004).
Silverman, J., et. al. "Multivalent avimer proteins evolved by exon shuffling of a family of human receptor domains" Nat. Biotechnol. 23, 1556-1561 (2005).
Bes, C., et. al. "PIN-bodies: A new class of antibody-like proteins with CD4 specificity derived from the protein inhibitor of neuronal nitric oxide synthase" Biochem. Biophys. Res. Comm. 343, 334-344 (2006)

What is claimed is:

1. A composition, comprising:
   (a) a first affinity element bound to a template nucleic acid strand;
   (b) a second affinity element bound to a complementary nucleic acid strand,
   wherein the first affinity element and the second affinity element non-competitively bind to a common target comprising polypeptides;
   wherein the template nucleic acid strand and the complementary nucleic acid strand are annealed via base pairing to form an assembly;
   wherein the first affinity element and the second affinity element are separated in the assembly; and
   wherein either the template nucleic acid strand, the complementary nucleic acid strand, or both, are bound to a surface of a substrate.

2. An array, comprising a plurality of the compositions of claim 1 bound to a substrate surface, wherein the plurality of compositions comprises one or both of:
   (a) a plurality of compositions wherein the first affinity element and the second affinity element are the same for each composition, but wherein the separation of the first affinity element from the second affinity element in the assembly differs; and
   (b) a plurality of compositions wherein the first affinity element and/or the second affinity element are different for each composition.

3. A composition, comprising:
   (a) a first affinity element bound to a template nucleic acid strand;
   (b) a second affinity element bound to a complementary nucleic acid strand, wherein the first affinity element and the second affinity element non-competitively bind to a common target comprising polypeptides;
   wherein the template nucleic acid strand and the complementary nucleic acid strand are annealed via base pairing to form an assembly;
   wherein the first affinity element and the second affinity element are separated in the assembly; and
   wherein the template nucleic acid strand is bound to a surface of a substrate.

4. An array, comprising a plurality of the compositions of claim 3 bound to a substrate surface, wherein the plurality of compositions comprises a plurality of compositions wherein the first affinity element and the second affinity element are different for each composition.

5. A composition, comprising:
   (a) a first affinity element bound to a template nucleic acid strand;
   (b) a second affinity element bound to a complementary nucleic acid strand,
   wherein the first affinity element and the second affinity element non-competitively bind to a common target comprising polypeptides;
   wherein the template nucleic acid strand and the complementary nucleic acid strand are annealed via base pairing to form an assembly;
   wherein the first affinity element and the second affinity element are separated in the assembly;
   wherein the first affinity element and the second affinity element are different peptides with sequences that are different from each other; and
   wherein either the template nucleic acid strand, the complementary nucleic acid strand, or both, are bound to a surface of a substrate.

* * * * *

UNITED STATES PATENT AND TRADEMARK OFFICE
CERTIFICATE OF CORRECTION

PATENT NO. : 9,863,938 B2
APPLICATION NO. : 14/198316
DATED : January 9, 2018
INVENTOR(S) : Stephen A Johnston et al.

Page 1 of 1

It is certified that error appears in the above-identified patent and that said Letters Patent is hereby corrected as shown below:

In the Specification

In Column 1, Line 13:
Delete the following paragraph:
"STATEMENT OF GOVERNMENT INTEREST
This application was supported in part by U.S. government funding under NIAID grant number 5 U54 AI057156 and NCI grant number 5 U54 CA112952, and thus the U.S. government has certain rights in the invention."

Insert the following paragraph:
-- GOVERNMENT SUPPORT CLAUSE
This invention was made with government support under U54 AI057156 and U54 CA112952 awarded by the National Institutes of Health. The government has certain rights in the invention. --

Signed and Sealed this
Twenty-sixth Day of November, 2019

Andrei Iancu
*Director of the United States Patent and Trademark Office*